US006468537B1

(12) United States Patent
Datta et al.

(10) Patent No.: US 6,468,537 B1
(45) Date of Patent: Oct. 22, 2002

(54) LOCALIZATION OF MAJOR PEPTIDE AUTOEPITOPES FOR NUCLEOSOME SPECIFIC T CELLS OF SYSTEMIC LUPUS ERYTHEMATOSUS

(75) Inventors: Syamal K. Datta, Winnetka; Arunan Kaliyaperumal, Skokie, both of IL (US)

(73) Assignee: The Board of Trustees of Northwestern University, Evanston, IL (US)

( * ) Notice: Subject to any disclaimer, the term of this patent is extended or adjusted under 35 U.S.C. 154(b) by 0 days.

(21) Appl. No.: 09/561,490

(22) Filed: Apr. 28, 2000

Related U.S. Application Data

(60) Provisional application No. 60/131,448, filed on Apr. 28, 1999.

(51) Int. Cl.[7] .................. A61K 38/04; A61K 38/10; A61K 38/16; C07K 7/08; C07K 14/00

(52) U.S. Cl. .................. 424/185.1; 424/184.1; 530/300; 530/325; 530/326; 530/327; 514/2; 514/13; 514/14; 514/866; 514/885

(58) Field of Search .................. 424/184.1, 185.1; 514/1, 2, 885, 866, 12, 13, 14, 15; 530/300, 325, 326, 327

(56) References Cited

U.S. PATENT DOCUMENTS

| | | | |
|---|---|---|---|
| 4,777,049 A | | 10/1988 | Magruder et al. |
| 5,645,820 A | | 7/1997 | Hafler et al. |
| 5,780,432 A | * | 7/1998 | Zeppezauer et al. |
| 6,022,544 A | * | 2/2000 | Dintzis et al. |

OTHER PUBLICATIONS

Smilek et al. Proc. Natl. Acad. Sci USA 1991 88:9633–9637.*
Kumar et al. Proc. Natl. Acad. Sci. USA 1990 87:1337–1341.*
Voll et al., 1997, Arthr. Rheum. 40:2162–2171.
Ravirajan et al., 1995, Autoimmunity 21:117–122.
Adams, et al., 1991, Proc. Natl. Acad. Sci. USA 88:11271–11275.
Anderton et al. 1999, Immunological Rev. 169:123–127.
Baggi et al. 1999, J. Clin. Invest. 104:1287.
Benson et al. 1999, J. Immunol. 162:6247.
Briner et al. 1993, Proc. Natl. Acad. Sci. USA. 90:7608.
Buhlmann et al. 1995, Immunity 2:645.
Burlingame, et al., 1993, J. Clin. Invest. 91:1687–1696.
Chan and Shlomchik 1998, J. Immunol. 160:51.
Chase. 1946, Proc. Soc. Exp. Biol. Med. 61:257.
Chicz et al., 1992, Nature 358:764–768.
Chicz et al., 1993, J. Exp. Med. 178:27–47.
Craft and Fatenejad, 1997, Arthritis Rheum. 40:1374–1382.
Crawford et al. 1998, Immunity 8:675.
Datta and Kaliyaperumal, 1997, Annals. New. York Acad. Sci. 815:155.
Datta and Schwartz, 1976, Nature 263:412.
Datta et al. 1978, J. Exp. Med. 147:854.
Datta et al. 1987, J. Exp. Med. 165:1252–1268.
Datta et al., 1982, J. Immunol. 129:1539.
DeMagistris et al. 1992, Cell. 68:625.
DePalma et al.,1999, J. Immunol. 162:1982.
Desai–Mehta et al., 1995, J. Clin. Invest. 95:531–541.
Desai–Mehta et al., 1996, J. Clin. Invest. 97:2063–2073.
Eastcott et al., 1983, J. Immunol. 131:2232.
Estcourt et al., 1997, Clin. Immunol. Immunopathol. 83:60–67.
Evabold et al. 1993, Immunol. Today. 14:602.
Eynon and Parker 1992, J. Exp. Med. 175:131.
Folsom et al., 1984, Proc. Natl. Acad. Sci. USA 81:2045–2049.
Gavalchin et al. 1985, J. Immunol. 134:885.
Gaynor et al., 1997, Proc. Natl. Acad. Sci. USA 94:1955.
Ishida et al., 1994, J. Exp. Med 179:305–310.
Javed et al. 1995, J. Immunol. 155:1599.
Jenkins and Schwartz. 1987, J. Exp. Med. 165:302.
Jongstra–Bilen, 1997, J. Immunol. 159:5810.
Kaliyaperumal et al., 1996, J. Exp. Med 183:2459–2469.
Kalled et al., 1998, J. Immunol. 160:2158.
Karin et al. 1994, J. Exp. Med. 180:2227.
Klinman and Steinberg, 1987, J. Exp. Med. 165:1755.
Kono and Theofilopoulos, 1996, J. Autoimmunity 9:437.
Korb et al., 1999, J. Immunol. 162:6401.
Koshy et al., 1996, J. Clin. Invest. 98:826.
Kotzin et al. 2000 Proc. Natl. Acad. Sci. USA. 97:291.
Kretz–Rommel, et al., 1997, J. Clin. Invest. 99:1888.
Kuchroo et al. 1994, J. Immunol. 153:3326.
Lebowitz et al. 1999, Cell. Immunol. 192:175.

(List continued on next page.)

*Primary Examiner*—Phillip Gambel
*Assistant Examiner*—Jessica H. Roark
(74) *Attorney, Agent, or Firm*—Morgan, Lewis & Bockius, LLP

(57) ABSTRACT

The present invention includes peptides derived from nucleosomal histone proteins which are useful for delaying the onset and progression of systemic lupus erythematosus (i.e. lupus or SLE). The peptides of the invention span the histone proteins (i.e. H1, H2A, H2B, H3, and H4). The invention additionally encompasses isolated nucleic acids which encode these histone peptides as well as pharmaceutical compositions which comprise one or more of a histone peptide. Further, the invention provides kits which comprise one or more histone peptides or isolated nucleic acids encoding histone peptides and an instructional material. The invention also provides methods of using these compositions and analogs of histone peptides to inhibit an immune response and associated inflammation in an animal and to treat disorders in an animal which are related to the production of autoantibodies and complications thereof, such as inflammatory diseases, autoimmune disorders, and nephritis.

8 Claims, 73 Drawing Sheets

OTHER PUBLICATIONS

Lehman et al., 1992, Nature 358:155.
Liang et al., 1989, Arthritis. Rheum. 32:1107–1118.
Liblau et al. 1997, Immunol. Today 18:599.
Liossis et al., 1996, J. Clin. Invest. 98:2549.
Llorente et al., 1995, J. Exp. Med 18 1:839–844.
Losman, et al., 1992, J. Immunol., 148:1561–1569.
Madrenas et al. 1997, J. Exp. Med. 185:219.
Mamula et al. 1994, J. Immunol. 152:1453.
McMichael and Kelleher. 1999, J. Clin. Invest. 104: 1669.
Mohan et al., 1993, J. Exp. Med. 177:1367–1381.
Mohan et al., 1995, J. Immunol. 154:1470–1480.
Monestier and Kotzin, 1992, Rheum. Dis. Clin. N. Am. 18:415–436.
Morel and Wakeland, 1998, Current Opin. Immunol. 10:718–725.
Mouritsen, et al., 1994, Immunology 82:529–534.
Nakajima et al., 1997, J. Immunol. 158:1466.
Openshaw et al., 1995, J. Exp. Med 182:1357–1367.
Rabinowitz et al. 1996, Immunity 5:125.
Rajagopalan et al. 1990, Proc. Natl. Acad. Sci. USA. 87:7020–7024.
Ray et al., 1996, Proc. Nati. Acad Sci. USA. 93:2019–2024.
Sainis and Datta, 1988, J. Immunol. 140:2215–2224.
Shi et al., 1998, J. Exp. Med. 187:367–378.
Shivakumar et al., 1989, J Immunol.143:103–112.
Shokat and Goodnow 1995, *Nature.* 375:334.
Sloan–Lancaster et al. 1994, J. Exp. Med. 180:1195.
Southwood et al., 1998, J. Immunol. 160:3363–3373.
Stemmer et al., 1996,.J. Biol. Chem. 271:21257–21261.
Stemmer et al., 1997, J. Mol. Biol. 273:52–60.
Tung et al. 1997, Current Opin. Immunol. 9:839.
Voll et al., 1997, Arthritis Rheum. 40:2162.
Wakeland et al., 1997, J. Clin. Immunol. 17:272.
Waldrop et al., 1997, J. Clin. Invest. 99:1739–1750.
Warren et al. 1995, Proc. Natl. Acad. Sci. USA. 92:11061.
Weiner et al., 1993, Science. 259:1321.
Weiner. 1994, Proc. Natl. Acad. Sci USA. 91:10762.
Wells. 1911, J. Infect. Dis. 8:147.
Wortis et al., 1995, Proc. Natl. Acad. Sci. USA 92:3348.
Wucherpfennig and Strominger, 1995, Cell. 80:695–705.
Wucherpfennig et al. 1997, J. Clin. Invest. 100:1114.
Yager, et al., 1989, Biochem. 28:2271–2281.
Yu et al. 1996, J. Exp. Med. 183:1771.
Zhong et al. 1997, J. Exp. Med. 186:673.

* cited by examiner

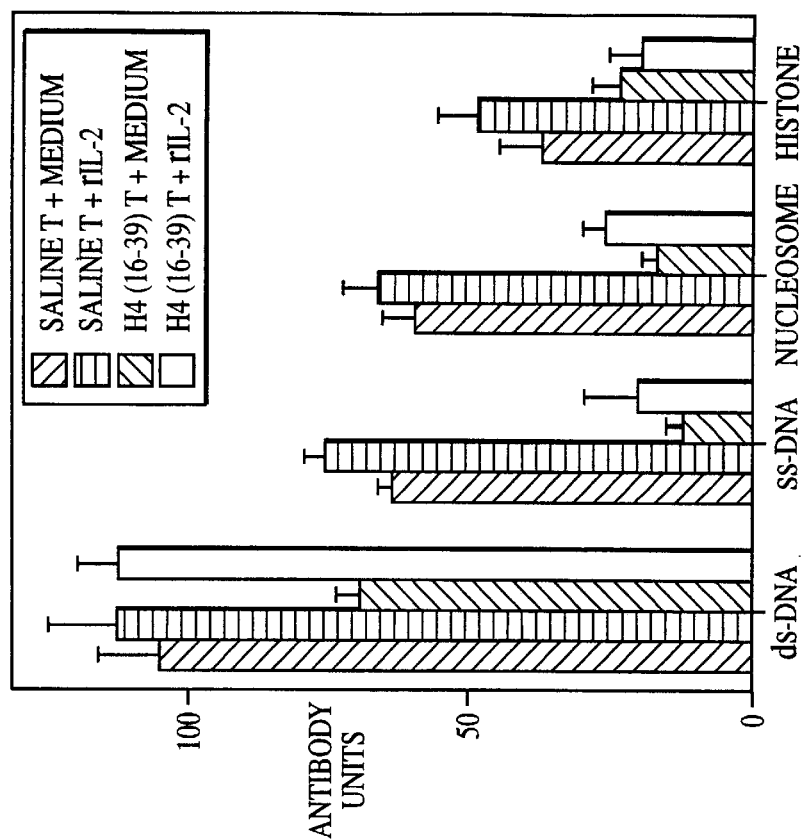
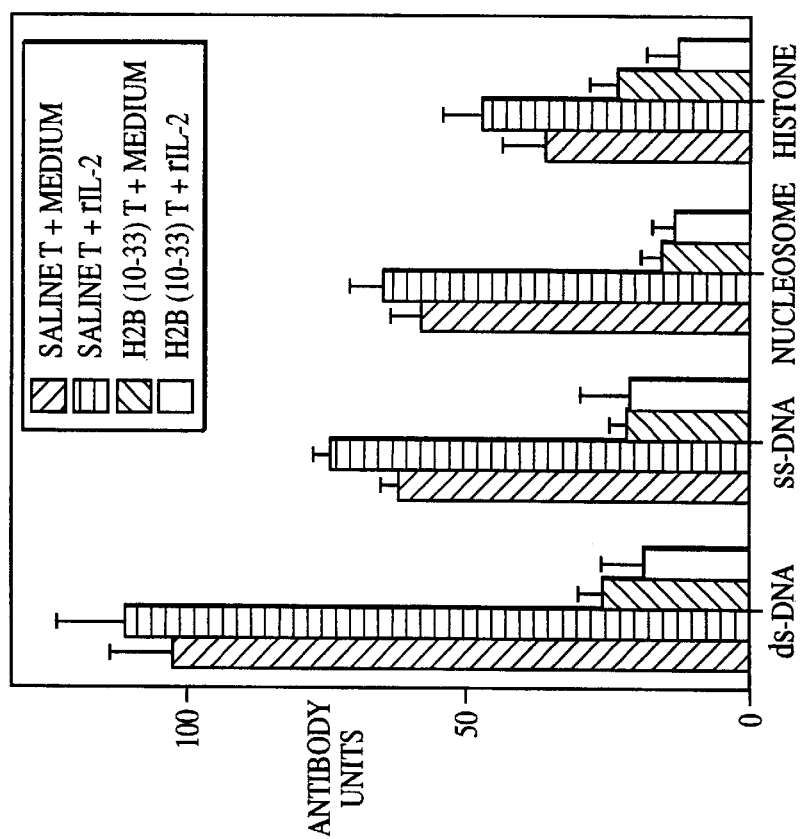
Fig. 4A
Fig. 4B

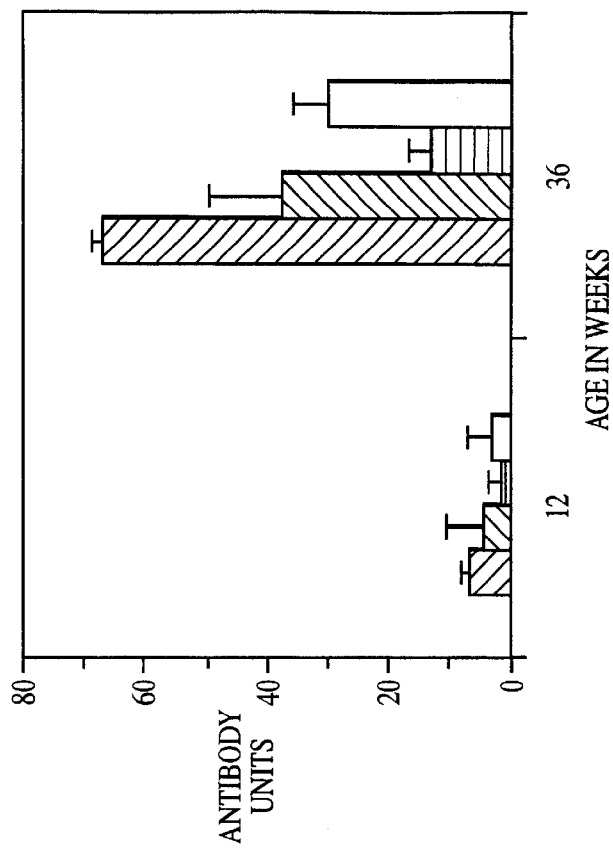
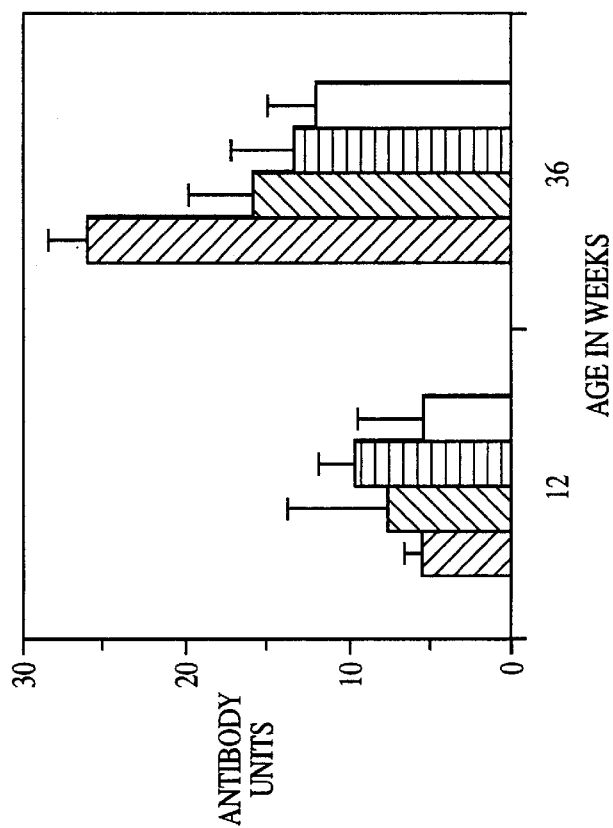
Fig. 9A
Fig. 9B

| STIMULATORY REGION | SYNTHETIC PEPTIDES | SEQUENCE ID NO. | AMINO ACID SEQUENCE |
|---|---|---|---|
| H2A 34-38 | H2A 34-48 | 9 | LRKGNYAERVGAGAP |
| H2A 72-86 | H2A 72-86 | 10 | DNKKTRIIPRHLQLA |
| H2A 97-126 | H2A 97-111 | 16 | LGKVTIAQGGVLPNI |
|  | H2A 106-120 | 17 | GVLPNIQAVLLPKKT |
|  | H2A 112-126 | 18 | QAVLLPKKTESHHKA |
| H2B 10-33 | H2B 10-33 | 7 | PKKGSKKAVTKAQKKDGKKRKRSR |
| H2B 13-27 | H2B 13-27 | 19 | GSKKAVTKAQKKDGK |
| H2B 46-60 | H2B 46-60 | 20 | KQVHPDTGISSKAMG |
| H2B 68-82 | H2B 68-82 | 8 | DIFERIAGEASRLAH |
| H3 55-69 | H3 55-69 | 11 | QKSTELLIRKLPFQR |
| H3 83-97 | H3 83-97 | 12 | RFQSSAVMALQEASE |
| H3 85-102 | H3 85-102 | 13 | QSSAVMALQEASEAYLVG |
|  | H3 91-105 | 14 | ALQEASEAYLVGLFE |
| H3 100-114 | H3 100-114 | 5 | LVGLFEDTNLCAIHA |

FIG. 17A

| STIMULATORY REGION | SYNTHETIC PEPTIDES | SEQUENCE ID NO. | AMINO ACID SEQUENCE |
|---|---|---|---|
| H4 4-30 | H4 5-19 | 22 | KGGKGLGKGGAKRHR |
| | H4 14-28 | 4 | GAKRHRKVLRDNIQG |
| H4 16-39 | H4 16-39 | 3 | KRHRKVLRDNIQGITKPAIRRIAR |
| H4 49-63 | H4 49-63 | 2 | LIYEETRGVLKVFLE |
| H4 67-93 | H4 67-81 | 21 | RDAVTYTEHAKRKTV |
| | H4 71-94 | 1 | TYTEHAKRKTVTAMDVVYALKRQG |
| | H4 73-87 | 15 | TEHAKRKTVTAMDVV |
| | H4 79-93 | 6 | KTVTAMDVVYALKRQ |
| ELUTED PEPTIDES | EP-1 | 23 | SQKEEEGAQREKE |
| | EP-2 | 24 | DWMEEEGAQREKE |
| H5 22-42 | H5 22-42 | 25 | SASHPTYSEMIAAAIRAEKSR |
| H1 22-42 | H1 22-42 | 26 | STDHPKYSDMIVAAIQAEKNR |

FIG. 17B

| FIG. 19A-1 | FIG. 19A-4 | FIG. 19A-7 |
|---|---|---|
| FIG. 19A-2 | FIG. 19A-5 | FIG. 19A-8 |
| FIG. 19A-3 | FIG. 19A-6 | FIG. 19A-9 |

| PATIENT SYMBOL | R-WG | | | | R-DS | | | |
|---|---|---|---|---|---|---|---|---|
| CYTOKINES | IFN-γ | IL-10 | IL-2 | IL-4 | IFN-γ | IL-10 | IL-2 | IL-4 |
| 15MER PEPTIDE | | | | | | | | |
| H2A 34-48 | 0.25 | 0.45 | 0 | 0.01 | 0.26 | 0.19 | 0.08 | 0.23 |
| H2A 72-86 | 0.24 | 2.32 | 0.19 | 0.19 | 0.16 | 0.09 | 0.16 | 0.16 |
| H2A 97-111 | 0.14 | 0.10 | 0.18 | 0.04 | 0.40 | 0.22 | 0.07 | 0.23 |
| H2A 106-120 | 0.17 | 0.07 | 0.05 | 0.01 | 0.29 | 0.13 | 0.06 | 0.04 |
| H2A 112-126 | 0.10 | 0.15 | 0.18 | 0.04 | 0.23 | 0.12 | 0.05 | 0.08 |
| H2B 13-27 | 0.06 | 1.23 | 0.10 | 0.10 | 0.03 | 0.11 | 0.04 | 0.07 |
| H2B 46-60 | 0.24 | 0.08 | 0.08 | 0.01 | 0.12 | 0.27 | 0.01 | 0.13 |
| H2B 68-82 | 0.20 | 2.20 | 0.07 | 0 | 0.16 | 0.10 | 0.04 | 0.15 |
| H3 91-105 | 0.87 | 0.33 | 0.09 | 0.36 | 0.48 | 0.10 | 0.09 | 0.31 |

FIG. 19A-2

| | | | | | | | | | |
|---|---|---|---|---|---|---|---|---|---|
| H3 100-114 | 0.50 | 0.36 | 0.15 | 0.08 | 0.27 | 0.51 | 0.25 | 0.22 | |
| H4 5-19 | 0.19 | 0.23 | 0.08 | 0.06 | 0.24 | 0.11 | 0.01 | 0 | |
| H4 14-28 | 0.27 | 0.74 | 0.09 | 0.04 | 0.24 | 0.08 | 0.27 | 0.17 | |
| H4 49-63 | 0.13 | 0.25 | 0.07 | 0.07 | 0.31 | 0.07 | 0.09 | 0.17 | |
| H4 67-81 | 0.10 | 0.09 | 0.08 | 0.08 | 0.16 | 0.06 | 0.01 | 0 | |
| H4 73-87 | 0.17 | 0.10 | 0.06 | 0.02 | 0.20 | 0.04 | 0.13 | 0.31 | |
| H4 79-93 | 0.21 | 1.51 | 0.10 | 0.01 | 0.32 | 0.27 | 0.14 | 0.17 | |

24MER PEPTIDE

| | | | | | | | | | |
|---|---|---|---|---|---|---|---|---|---|
| H2B 10-33 | 0.74 | 0.04 | 0.12 | 0.05 | 0.38 | 0.27 | 0.03 | 0.03 | |
| H4 16-39 | 0.34 | 0.16 | 0.15 | 0.01 | 0.38 | 0.14 | 0.02 | 0.04 | |
| H4 71-94 | 0.54 | 0.15 | 0.11 | 0.02 | 0.26 | 0.16 | 0.07 | 0 | |

FIG. 19A-3

| | | | | | | | | | |
|---|---|---|---|---|---|---|---|---|---|
| NUCLEOSOME | 0.87 | 0.39 | 0.03 | 0.06 | 1.31 | 0.17 | 0.18 | 0.09 | |
| CONTROL PEPTIDE H3 83-97 | 0.23 | 0.18 | 0.14 | 0.04 | 0.20 | 0.18 | 0.01 | 0 | |
| MEDIUM | 0.13 | 0.11 | 0.05 | 0.03 | 0.11 | 0.11 | 0.04 | 0.06 | |
| ANTI-CD3 | 12.72 | 0.50 | 2.13 | 0.14 | 7.90 | 0.79 | 7.73 | 0.37 | |

FIG. 19A-4

| | R-SC | | | | R-FN | | | | R-JE | | |
|---|---|---|---|---|---|---|---|---|---|---|---|
| IFN-γ | IL-10 | IL-2 | IL-4 | IFN-γ | IL-10 | IL-2 | IL-4 | IFN-γ | IL-10 | IL-2 | IL-4 |
| 0.34 | 0.40 | 0.14 | 0.10 | 0.07 | 0.04 | 0.13 | 0.13 | 0.49 | 0.76 | 0.44 | 0.40 |
| 0.24 | 0.38 | 0.10 | 0.17 | 0.07 | 0.07 | 0.08 | 0.05 | 0.21 | 0.90 | 0.03 | 0.19 |
| 0.22 | 0.24 | 0.22 | 0.14 | 0.17 | 0.06 | 0 | 0 | 0.12 | 0.23 | 0.08 | 0.19 |
| 0.30 | 0.29 | 0.16 | 0.29 | 0.11 | 0.07 | 0 | 0 | 0.19 | 0.12 | 0.09 | 0.24 |
| 0.31 | 0.31 | 0.17 | 0.11 | 0.06 | 0.02 | 0.07 | 0.05 | 0.18 | 0.36 | 0.02 | 0.16 |
| 0.28 | 0.35 | 0.21 | 0.12 | 0.04 | 0.02 | 0.12 | 0 | 0.17 | 0.69 | 0.12 | 0.20 |
| 0.25 | 0.26 | 0.18 | 0.07 | 0.09 | 0.02 | 0.08 | 0.08 | 0.06 | 0.10 | 0.07 | 0.11 |
| 0.23 | 0.18 | 0.24 | 0.14 | 0.05 | 0.02 | 0.19 | 0.08 | 0.24 | 0.32 | 0.1 | 0.13 |
| 0.37 | 0.25 | 0.28 | 0.20 | 0.10 | 0.10 | 0.12 | 0.08 | 0.15 | 0.26 | 0.06 | 0.20 |

FIG. 19A-5

| | | | | | | | | | | | | |
|---|---|---|---|---|---|---|---|---|---|---|---|---|
| 0.44 | 0.44 | 0.22 | 0.17 | 0.12 | | | 0.14 | | | | | |
| 0.33 | 0.51 | 0.15 | 0.07 | 0.10 | 0.11 | 0.03 | | 0.29 | 0.13 | 0.26 | | |
| 0.12 | 0.20 | 0.12 | 0.07 | 0.10 | 0.18 | 0.12 | 0.27 | 0.40 | 0.06 | 0.26 | | |
| 0.34 | 0.43 | 0.17 | 0.07 | 0.21 | 0.04 | 0.03 | 0.19 | 0.25 | 0.03 | 0.13 | | |
| 0.24 | 0.18 | 0.11 | 0.12 | 0.04 | 0.10 | 0.16 | 0.04 | 0.37 | 0.16 | 0.16 | 0.23 | |
| 0.19 | 0.28 | 0.14 | 0.11 | 0.06 | 0.09 | 0.16 | 0.04 | 0.12 | 0.35 | 0.08 | 0.11 | |
| 0.19 | 0.18 | 0.14 | 0.05 | 0.08 | 0.06 | 0.07 | 0.10 | 0.15 | 0.47 | 0.08 | 0.17 | |
| | | | | | 0.02 | 0.15 | 0.03 | 0.24 | 0.47 | 0.06 | 0.13 | |
| ND | ND | ND | ND | ND | ND | 0 | 0.01 | 0.14 | 0.26 | 0.11 | | 0.40 |
| ND | ND | ND | ND | ND | ND | 0 | 0 | 0.11 | 0.33 | 0.11 | | 0.12 |
| ND | ND | ND | ND | ND | ND | 0 | 0.01 | 0.31 | 0.41 | 0.1 | | 0.21 |

FIG. 19A-6

| |0.32| 0.18 | 0.16 | 0.12 | 0.10 | |0.31| | 0 | 0.15 | |0.54| |0.36| 0.21 | |0.26| |
|---|---|---|---|---|---|---|---|---|---|---|---|---|---|

| R-HH | | | |
|---|---|---|---|
| IFN-γ | IL-10 | IL-2 | IL-4 |
| 0.02 | 0.18 | 0.13 | 0.12 |
| 0.11 | 0.39 | 0.07 | 0.05 |
| 0.26 | 0.03 | 0.04 | 0.07 |
| 0.08 | 0.07 | 0.03 | 0.07 |
| 0.10 | 0.03 | 0.03 | 0.12 |
| 0.17 | 0.12 | 0 | 0.01 |
| 0.04 | 0.05 | 0.04 | 0.05 |
| 0.03 | 0.05 | 0.05 | 0.02 |
| 0.06 | 0.23 | 0.15 | 0.44 |

FIG. 19A-8

| 0.11 | 0.17 | 0.13 | 0.05 |
| --- | --- | --- | --- |
| 0.12 | 0.05 | 0.13 | 0.46 |
| 0.02 | 0.03 | 0.06 | 0.05 |
| 0.10 | 0.04 | 0.10 | 0.02 |
| 0.07 | 0.06 | 0.12 | 0.12 |
| 0.02 | 0.31 | 0.05 | 0.07 |
| 0.01 | 0.04 | 0.06 | 0.28 |
| 0.26 | 0.54 | 0.07 | 0.09 |
| 0.03 | 0.03 | 0.07 | 0.15 |
| 0.22 | 0.11 | 0.03 | 0.04 |

FIG. 19A-9

| 0.07 | 0.09 | 0.10 | 0.12 |
|------|------|------|------|
| 0.04 | 0.07 | 0.1  | 0.06 |
| 0.04 | 0.03 | 0.06 | 0.07 |
| 4.27 | 0.08 | 3.16 | 0.66 |

| FIG. 19B-1 | FIG. 19B-4 | FIG. 19B-7 |
| --- | --- | --- |
| FIG. 19B-2 | FIG. 19B-5 | FIG. 19B-8 |
| FIG. 19B-3 | FIG. 19B-6 | FIG. 19B-9 |

| PATIENT SYMBOL | | R-DW | | | | R-SS | | |
|---|---|---|---|---|---|---|---|---|
| CYTOKINES | IFN-γ | IL-10 | IL-2 | IL-4 | IFN-γ | IL-10 | IL-2 | IL-4 |
| 15MER PEPTIDE | | | | | | | | |
| H2A 34-48 | 0.25 | 0.30 | ND | ND | 0.11 | 0.13 | ND | ND |
| H2A 72-86 | 0.04 | 0.03 | ND | ND | 0.08 | 0.17 | ND | ND |
| H2A 97-111 | 0.12 | 0.12 | ND | ND | 0.10 | 0.17 | ND | ND |
| H2A 106-120 | 0.14 | 0.20 | ND | ND | 0.13 | 0.10 | ND | ND |
| H2A 112-126 | 0.21 | 0.08 | ND | ND | 0.14 | 0.15 | ND | ND |
| H2B 13-27 | 0.19 | 0.07 | ND | ND | 0.25 | 0.06 | ND | ND |
| H2B 46-60 | 0.18 | 0.03 | ND | ND | 0.13 | 0.21 | ND | ND |
| H2B 68-82 | 0.18 | 0.05 | ND | ND | 0.14 | 0.14 | ND | ND |
| H3 91-105 | 0.22 | 0.04 | ND | ND | 0.97 | 0.18 | ND | ND |

FIG. 19B-2

| Peptide | | | | | | |
|---|---|---|---|---|---|---|
| H3 100-114 | 0.22 | 0.10 | ND | 0.35 | 0.28 | ND |
| H4 5-19 | 0.04 | 0.05 | ND | 0.12 | 0.14 | ND |
| H4 14-28 | 0.35 | 0.07 | ND | 0 | 0.46 | ND |
| H4 49-63 | 0.13 | 0.01 | ND | 1.21 | 0.05 | ND |
| H4 67-81 | 0.06 | 0.07 | ND | 0.08 | 0.13 | ND |
| H4 73-87 | 0.09 | 0.10 | ND | 0.07 | 0.05 | ND |
| H4 79-93 | 0.05 | 0.03 | ND | 0.16 | 0.32 | ND |

24MER PEPTIDE

| Peptide | | | | | | |
|---|---|---|---|---|---|---|
| H2B 10-33 | 0.21 | 0.06 | ND | 0.34 | 0.09 | ND |
| H4 16-39 | 0.28 | 0.08 | ND | 0.94 | 0.04 | ND |
| H4 71-94 | 0.26 | 0.04 | ND | 0.74 | 0.11 | ND |

FIG. 19B-3

| | | | | | | | |
|---|---|---|---|---|---|---|---|
| NUCLEOSOME | 0.65 | 0.09 | ND | ND | 0.69 | 0.17 | ND | ND |
| CONTROL PEPTIDE H3 83-97 | 0.10 | 0.08 | ND | ND | 0 | 0.20 | ND | ND |
| MEDIUM | 0.13 | 0.04 | ND | ND | 0.27 | 0.17 | ND | ND |
| ANTI-CD3 | 6.13 | 0.05 | ND | ND | 20.8 | 0.29 | ND | ND |

FIG. 19B-4

| | A-MC | | | | A-VS | | | | A-KJ | | | |
|---|---|---|---|---|---|---|---|---|---|---|---|---|
| | IFN-γ | IL-10 | IL-2 | IL-4 | IFN-γ | IL-10 | IL-2 | IL-4 | IFN-γ | IL-10 | IL-2 | IL-4 |
| | 0.95 | 1.55 | 0.16 | | 0.02 | 0.38 | 0 | 0 | 0.04 | 0.02 | 0.12 | 0.04 |
| | 0.46 | 0.16 | 0.12 | 0.49 | 0.13 | 0.30 | 0.17 | 0.93 | 0.06 | 0.04 | 0.13 | 0.10 |
| | 0.09 | 1.95 | 0.49 | 1.17 | 0.01 | 0.14 | 0.17 | 0.31 | 0.06 | 0.02 | 0.15 | 0.03 |
| | 0.39 | 1.23 | 0.33 | 0.37 | 0.1 | 0.08 | 0 | 0.08 | 0.05 | 0.05 | 0.2 | 0.02 |
| | 0.44 | 0.80 | 0.27 | 0.77 | 0.11 | 0.37 | 0.09 | 0.12 | 0.03 | 0.09 | 0.13 | 0.04 |
| | 0.59 | 0.62 | 0.22 | 0.41 | 0.12 | 0.21 | 0.11 | 0.28 | 0.08 | 0.03 | 0.18 | 0.04 |
| | 0.50 | 0.40 | 0 | 0.94 | 0.12 | 0.32 | 0.07 | 0.36 | 0.04 | 0.01 | 0.13 | 0.04 |
| | 0.11 | 0.55 | 0.11 | 0.39 | 0.07 | 0.13 | 0.03 | 0.20 | 0.13 | 0.08 | 0.09 | 0.10 |
| | | 0.70 | 0.79 | 0.91 | | 0.2 | | | 0.03 | 0.01 | | |
| | 0.81 | | | 0.71 | 0.20 | 0.12 | 0.12 | 0.43 | 0.03 | 0.01 | 0.20 | 0.04 |

FIG. 19B-5

| | | | | | | | | | | | |
|---|---|---|---|---|---|---|---|---|---|---|---|
| 0.64 | 0.48 | 0.53 | 0.53 | 0.16 | 0.18 | 0.09 | 0.19 | 0.03 | 0.02 | 0.05 | 0.31 |
| 0.49 | 0.42 | 0.72 | 0.84 | 0.08 | 0.22 | 0.02 | 0.30 | 0.04 | 0.02 | 0.26 | 0 |
| 0.69 | 0.19 | 2.06 | 0.46 | 0.15 | 0.36 | 0.04 | 0.18 | 0.04 | 0.03 | 0.13 | 0.04 |
| 0.11 | 0.57 | 0.68 | 0.95 | 0.16 | 0.47 | 0.06 | 0.12 | 0.05 | 0.05 | 0.13 | 0.06 |
| 0.65 | 0.22 | 0.52 | 0.94 | 0.09 | 0.17 | 0.09 | 0.19 | 0.10 | 0.04 | 0.11 | 0.06 |
| 0.55 | 0.17 | 1.16 | 1.09 | 0.02 | 0.11 | 0.11 | 0.39 | 0.02 | 0.05 | 0.13 | 0.01 |
| 0.24 | 0.11 | 0.55 | 0.62 | 0.08 | 0.19 | 0 | 0.06 | 0.04 | 0.04 | 0.12 | 0.03 |
| ND | ND | ND | ND | 0.19 | 0.36 | 0.07 | 0.63 | 0.10 | 0.04 | 0.04 | 0.05 |
| ND | ND | ND | ND | 0.30 | 0.12 | 0 | 0.08 | 0.05 | 0.01 | 0.07 | 0.06 |
| ND | ND | ND | ND | 0.20 | 0.32 | 0.15 | 0.29 | 0.06 | 0.05 | 0.09 | 0.09 |
| ND | ND | ND | ND | | | | | | | 0.11 | |

FIG. 19B-6

| 1.36 | 1.76 | 0.36 | 0.62 | 0.27 | 0.11 | 0 | | | | |
|------|------|------|------|------|------|---|---|---|---|---|
| 0.46 | 2.14 | 0.32 | 0.21 | 0.08 | 0.23 | 0.03 | 0.29 | 0.05 | 0.04 | 0.10 | 0.05 |
| 0.26 | 0.43 | 0.19 | 0.18 | 0.08 | 0.16 | 0.08 | 0.24 | 0.09 | 0.11 | 0.17 | 0.04 |
| 17.21 | 0.59 | 11.15 | 3.03 | 3.84 | 0.19 | 1.05 | 0.10 | 0.03 | 0.03 | 0.09 | 0.03 |
| | | | | | | | 0.82 | 0.48 | 0.05 | 0.81 | 0.24 |

FIG. 19B-7

| A-WB | | | |
|---|---|---|---|
| IFN-γ | IL-10 | IL-2 | IL-4 |
| 0.03 | 0.09 | 0.02 | 0.10 |
| 0.09 | 0.12 | 0.04 | 0.09 |
| 0.03 | 0.09 | 0.03 | 0.10 |
| 0.06 | 0.15 | 0.03 | 0.11 |
| 0.12 | 0.21 | 0.02 | 0.12 |
| 0.07 | 0.12 | 0.06 | 0.20 |
| 0.10 | 0.27 | 0.04 | 0.07 |
| 0.06 | 0.13 | 0.12 | 0.15 |
| 0.08 | 0.15 | 0.04 | 0.20 |

FIG. 19B-8

| 0.07 | 0.22 | 0.08 | 0.02 |
| 0.13 | 0.16 | 0.02 | 0.15 |
| 0.11 | 0.21 | 0.02 | 0.12 |
| 0.05 | 0.14 | 0.09 | 0.04 |
| 0.08 | 0.24 | 0.02 | 0.11 |
| 0.06 | 0.13 | 0 | 0.11 |
| 0.04 | 0.17 | 0.02 | 0.10 |
| 0.09 | 0.14 | 0.05 | 0.13 |
| 0.07 | 0.21 | 0 | 0.12 |
| 0.03 | 0.09 | 0.09 | 0.09 |

FIG. 19B-9

| 0.13 | 0.38 | 0.02 | 0.17 |
|------|------|------|------|
| 0.08 | 0.14 | 0.16 | 0.08 |
| 0.08 | 0.10 | 0.03 | 0.09 |
| 0.69 | 0.28 | 0.67 | 0.18 |

FIG. 20A

| Cytokine | IFN-γ | | | | | | | | |
|---|---|---|---|---|---|---|---|---|---|
| Donor Symbol | N-CM | N-MM | N-ST | N-JB | N-LL | N-MV | N-WG | | |

| 15mer Peptide | N-CM | N-MM | N-ST | N-JB | N-LL | N-MV | N-WG |
|---|---|---|---|---|---|---|---|
| H2A 34-48 | 0.05 | 0.15 | 0.05 | 0.07 | 0.16 | 0.09 | 0.04 |
| H2A 72-86 | 0.02 | 0.09 | 0.02 | 0.08 | 0.07 | 0.27 | 0.01 |
| H2A 97-111 | 0.02 | 0.05 | 0 | 0.01 | 0.12 | 0.06 | 0.01 |
| H2A 106-120 | 0.05 | 0.03 | 0.01 | 0.05 | 0.13 | 0.08 | 0.02 |
| H2A 112-126 | 0.05 | 0.16 | 0.08 | 0.01 | 0.12 | 0.15 | 0.08 |
| H2B 13-27 | 0.03 | 0.09 | 0.06 | 0.14 | 0.08 | 0.06 | 0.05 |
| H2B 46-60 | 0.02 | 0.01 | 0.05 | 0.05 | 0.05 | 0.05 | 0.01 |
| H2B 68-82 | 0.07 | 0.06 | 0.03 | 0.04 | 0.02 | 0.05 | 0.07 |
| H3 91-105 | 0.10 | 0.05 | 0.06 | 0 | 0.07 | 0.08 | 0.06 |
| H3 100-114 | 0.07 | 0.03 | 0.06 | 0.01 | 0.04 | 0.18 | 0.04 |

FIG. 20B

| | | | | | | | |
|---|---|---|---|---|---|---|---|
| H4 5-19 | 0.02 | 0.05 | 0.02 | 0.06 | 0.08 | 0.17 | 0 |
| H4 14-28 | 0.01 | 0.02 | 0 | 0.17 | 0.05 | 0.06 | 0.05 |
| H4 49-63 | 0.03 | 0.04 | 0.02 | 0.04 | 0.05 | 0.16 | 0.03 |
| H4 67-81 | 0.05 | 0.04 | 0.07 | 0.05 | 0.03 | 0.03 | 0.04 |
| H4 73-87 | 0.03 | 0.01 | 0.02 | 0.05 | 0.07 | 0.06 | 0.03 |
| H4 79-93 | 0 | 0.05 | 0.06 | 0.05 | 0.05 | 0.07 | 0.01 |
| Nucleosome | 0.06 | 0.04 | 0.07 | 0.14 | 0.10 | 0.05 | 0.15 |
| Control Peptide H3 83-97 | 0.06 | 0.03 | 0.03 | 0.02 | 0.04 | 0.04 | 0.06 |
| Medium | 0.09 | 0.04 | 0.05 | 0.02 | 0.09 | 0.06 | 0.03 |
| anti-CD3 | 7.77 | 2.34 | 5.62 | 3.24 | 6.04 | 2.09 | 6.34 |

FIG. 20C

| IL-10 | | | | | | | IL-2 | | | | | | |
|---|---|---|---|---|---|---|---|---|---|---|---|---|---|
| N-CM | N-MM | N-ST | N-JB | N-LL | N-MV | N-WG | N-CM | N-MM | N-ST | N-JB | N-LL | N-MV | N-WG |
| 0.05 | 0.17 | 0.05 | 0.08 | 0.16 | 0.04 | 0.06 | 0.07 | 0.02 | 0.02 | 0.08 | 0.12 | 0.17 | 0.02 |
| 0.01 | 0.24 | 0.05 | 0.07 | 0.30 | 0.97 | 0.01 | 0.01 | 0.04 | 0.08 | 0.03 | 0.04 | 0.09 | 0.07 |
| 0.02 | 0.05 | 0.04 | 0.03 | 0.29 | 0.12 | 0 | 0.06 | 0.02 | 0.04 | 0 | 0 | 0.09 | 0.26 |
| 0.03 | 0.08 | 0.04 | 0.05 | 0.30 | 0.26 | 0.02 | 0.04 | 0.01 | 0.01 | 0.02 | 0.14 | 0.1 | 0.02 |
| 0.01 | 0.25 | 0.15 | 0.05 | 0.30 | 0.39 | 0.04 | 0.01 | 0.03 | 0.01 | 0.06 | 0.08 | 0.17 | 0.16 |
| 0.04 | 0.21 | 0.13 | 0.17 | 0.05 | 0.10 | 0.04 | 0.02 | 0.04 | 0.03 | 0 | 0 | 0.02 | 0.15 |
| 0.04 | 0.07 | 0.09 | 0.05 | 0.11 | 0.17 | 0.03 | 0.02 | 0.02 | 0.04 | 0.04 | 0.18 | 0.11 | 0.24 |
| 0.10 | 0.21 | 0.11 | 0.05 | 0.11 | 0 | 0.01 | 0.04 | 0.02 | 0.04 | 0 | 0.07 | 0.1 | 0.08 |
| 0 | 0.1 | 0.07 | 0.08 | 0.21 | 0.12 | 0.01 | 0.11 | 0.14 | 0.11 | 0.15 | 0.05 | 0.26 | 0.14 |
| 0.02 | 0.04 | 0.09 | 0.06 | 0.08 | 0.10 | 0.06 | 0.07 | 0.01 | 0.06 | 0.11 | 0.31 | 0.4 | 0.08 |

FIG. 20D

| | | | | | | | | | | | | | |
|---|---|---|---|---|---|---|---|---|---|---|---|---|---|
| 0.02 | 0.05 | 0.09 | 0.03 | 0.17 | 0.40 | 0.03 | 0.03 | 0.03 | 0.04 | 0.05 | 0 | 0 | 0.18 |
| 0.02 | 0.08 | 0.07 | 0.17 | 0.1 | 0.01 | 0.01 | 0.06 | 0.05 | 0.03 | 0.01 | 0.01 | 0.07 | 0.06 |
| 0.09 | 0.05 | 0.07 | 0.20 | 0.11 | 0.09 | 0 | 0.07 | 0.02 | 0.17 | 0.04 | 0.29 | 0.16 | 0.32 |
| 0.06 | 0.06 | 0.13 | 0.05 | 0.05 | 0.03 | 0.03 | 0.02 | 0.04 | 0.03 | 0.01 | 0.14 | 0.14 | 0.08 |
| 0.06 | 0.05 | 0.04 | 0.04 | 0.26 | 0.03 | 0 | 0.02 | 0.03 | 0.01 | 0.01 | 0.12 | 0.1 | 0 |
| 0.09 | 0.08 | 0.07 | 0.05 | 0.15 | 0.10 | 0.03 | 0.01 | 0.03 | 0.03 | 0.01 | 0.05 | 0.08 | 0.06 |
| 0.05 | 0.09 | 0.23 | 0.15 | 0.17 | 0.01 | 0.20 | 0.11 | 0.02 | 0 | 0.04 | 0.02 | 0.13 | 0.33 |
| 0.01 | 0.13 | 0.05 | 0.04 | 0.08 | 0.14 | 0.02 | 0.04 | 0.02 | 0.03 | 0.03 | 0.09 | 0.03 | 0.11 |
| 0.10 | 0.14 | 0.08 | 0.05 | 0.13 | 0.11 | 0.07 | 0.06 | 0.04 | 0.04 | 0.02 | 0.04 | 0.08 | 0.09 |
| 0.20 | 0.62 | 2.09 | 0.87 | 0.45 | 0.26 | 0.65 | 1.29 | 1.93 | 5.09 | 1.52 | 3.55 | 1.03 | 3.92 |

| N-CM | N-MM | N-ST | N-JB | N-LL | N-MV | N-WG |
|---|---|---|---|---|---|---|
| 0.17 | 0.04 | 0.06 | 0.1 | 0.09 | 0.02 | 0.05 |
| 0.01 | 0.2 | 0.06 | 0.06 | 0.11 | 0 | 0.14 |
| 0.01 | 0.06 | 0.06 | 0 | 0.26 | 0.01 | 0.30 |
| 0.06 | 0.07 | 0.04 | 0.02 | 0.34 | 0 | 0.04 |
| 0.01 | 0.04 | 0.06 | 0 | 0.16 | 0.03 | 0.21 |
| 0.01 | 0.08 | 0.03 | 0 | 0.05 | 0.07 | 0.12 |
| 0.01 | 0.02 | 0.04 | 0.12 | 0.22 | 0.06 | 0.28 |
| 0.02 | 0.08 | 0.04 | 0.02 | 0.20 | 0 | 0.17 |
| 0 | 0.19 | 0.14 | 0.22 | 0.10 | 0.04 | 0.09 |
| 0.01 | 0.03 | 0.05 | 0.23 | 0.20 | 0.16 | 0.02 |

FIG. 20F

| | | | | | | | |
|---|---|---|---|---|---|---|---|
| 0.01 | 0.08 | 0.04 | 0.03 | 0.07 | 0.04 | | |
| 0.01 | 0.11 | 0.05 | 0.03 | 0.07 | 0.03 | | |
| 0.04 | 0.10 | 0.16 | 0.04 | 0.13 | 0 | | |
| 0 | 0.11 | 0.06 | 0.01 | 0.28 | 0.02 | | |
| 0.02 | 0.03 | 0 | 0.02 | 0.17 | 0 | | |
| 0.01 | 0.08 | 0.03 | 0.03 | 0 | 0 | | |
| 0 | 0.14 | 0.02 | 0.02 | 0.04 | 0.13 | | |
| 0.03 | 0.05 | 0.06 | 0.06 | 0.09 | 0.03 | 0.18 | |
| 0.06 | 0.1 | 0.04 | 0.02 | 0.11 | 0 | 0.14 | |
| 0.03 | 0.31 | 0.04 | 0.14 | 1.69 | 0.92 | 0.17 | |

(Boxed values: 0.29 in top row, 0.28 in middle)

Reconstructed as displayed:

| | | | | | |
|---|---|---|---|---|---|
| 0.01 | 0.08 | 0.04 | 0.03 | 0.07 | 0.04 | 0.29 |
| 0.01 | 0.11 | 0.05 | 0.03 | 0.07 | 0.03 | 0.06 |
| 0.04 | 0.10 | 0.16 | 0.04 | 0.13 | 0 | 0.2 |
| 0 | 0.11 | 0.06 | 0.01 | 0.28 | 0.02 | 0.09 |
| 0.02 | 0.03 | 0 | 0.02 | 0.17 | 0 | 0 |
| 0.01 | 0.08 | 0.03 | 0.03 | 0 | 0 | 0.06 |
| 0 | 0.14 | 0.02 | 0.02 | 0.04 | 0.13 | 0.07 |
| 0.03 | 0.05 | 0.06 | 0.06 | 0.09 | 0.03 | 0.18 |
| 0.06 | 0.1 | 0.04 | 0.02 | 0.11 | 0 | 0.14 |
| 0.03 | 0.31 | 0.04 | 0.14 | 1.69 | 0.92 | 0.17 |

FIG. 21

| | | POSITIVE RESPONDERS/TOTAL TESTED* | | | |
|---|---|---|---|---|---|
| Cytokines → | | IFN-g | IL-10 | IL-2 | IL-4 |
| 15mer | H2A $_{34-48}$ | *4/10* | 5/10 | 1/7 | 3/10 |
| Peptides | H2A $_{72-86}$ | 1/10 | *4/10* | 0 | 2/10 |
| | H2A $_{97-111}$ | 2/10 | 3/10 | 2/7 | 3/10 |
| | H2A $_{106-120}$ | 2/10 | 1/10 | 0 | 3/10 |
| | H2A $_{112-126}$ | 2/10 | 4/10 | 0 | 1/10 |
| | H2B $_{13-27}$ | 1/10 | 2/10 | 1/7 | *4/10* |
| | H2B $_{46-60}$ | 0 | 3/10 | 0 | 2/10 |
| | H2B $_{68-82}$ | 1/10 | 2/10 | 1/7 | 2/10 |
| | H3 $_{91-105}$ | 5/10 | *4/10* | 2/7 | 7/10 |
| | H3 $_{100-114}$ | *4/10* | 5/10 | *3/7* | *4/10* |
| | H4 $_{5-19}$ | 3/10 | 3/10 | 1/7 | *4/10* |
| | H4 $_{14-28}$ | *4/10* | 5/10 | 2/7 | 1/10 |
| | H4 $_{49-63}$ | 5/10 | 3/10 | 1/7 | 2/10 |
| | H4 $_{67-81}$ | 1/10 | 2/10 | 1/7 | 1/10 |
| | H4 $_{73-87}$ | 1/10 | 2/10 | 1/7 | 3/10 |
| | H4 $_{79-93}$ | 2/10 | 3/10 | 1/7 | 2/10 |
| 24mer | H2B $_{10-33}$ | *3/7* | 4/7 | 0 | 2/7 |
| Peptides | H4 $_{16-39}$ | 5/7 | 2/7 | 0 | 0 |
| | H4 $_{71-94}$ | 7/7 | 2/7 | 0 | 2/7 |
| Nucleosome | | 8/10 | 5/10 | 0 | 3/10 |
| Control Peptide | H3 $_{83-97}$ | 0 | 1/10 | 1/7 | 1/10 |

| HISTONE AUTO-EPITOPES | HLR-DR BINDING MOTIFS | |
|---|---|---|
| | HLA-DR1, 4, 7 | HLA-DR3 |
| H2A$_{34-48}$ | LRKGNYAERVGAGAP | |
| H2B$_{13-27}$ | GSKKAVTKAQKKDGK | |
| H3$_{91-105}$ | QSSAVMALQEASEAY | |
| H3$_{100-114}$ | EASEAYLVGLFEDTN | EASEAYLVGLFEDTN |
| H4$_{14-28}$ | GAKRHRKVLRDNIQG | GAKRHRKVLRDNIQG |
| H4$_{49-63}$ | LIYEETRGVKFLE | LIYEETRGVKFLE |
| H2B$_{10-33}$ | PKKGSKKAVTKAQKKDGKKKRKRSR | |
| H4$_{16-39}$ | KRHRKVLRDNIQGITKPAIRRLAR | KRHRKVLRDNIQGITKPAIRRLAR |
| H4$_{71-94}$ | TYTEHAKRKTVTAMDVVYALKRQG | TYTEHAKRKTVTAMDVVYALKRQG |

FIG. 22A

| FIG. 22A | FIG. 22B |

FIG. 22

| HISTONE AUTO-EPITOPES | HLR-DR BINDING MOTIFS |
|---|---|
| | HLA-DR8 |
| H2A$_{34-48}$ | |
| H2B$_{13-27}$ | |
| H3$_{91-105}$ | |
| H3$_{100-114}$ | |
| H4$_{14-28}$ | |
| H4$_{49-63}$ | LIYEETRGVKFLE |
| H2B$_{10-33}$ | |
| H4$_{16-39}$ | |
| H4$_{71-94}$ | TYTEHAKRKTVTAMDVVYALKRQG |

FIG. 22B

| Histone Peptide Autoepitopes | Sequence ID No. | Nucleotide Sequence |
|---|---|---|
| H2A 34-48 | 27 | CTGCGGAAAG GTAACTACGC GGAGCGGGTG GGGGCCGGAG CGCCCGT |
| H2A 72-86 | 28 | GACAACAAGA AGACGCGCAT CATCCCCCGC CACCTGCAGC TGGCCA |
| H2A 97-111 | 29 | CTGGGCCGCG TGACCATCGC GCAGGGCGGC GTCCTGCCCA ACATC |
| H2A 106-120 | 30 | GGCGTCCTGC CCAACATCCA GGCCGTGCTG CTGCCCAAGA AGACC |
| H2A 112-126 | 31 | CAGGCCGTGC TGCTGCCCAA GAAGACCGAG AGCCACCACA AGGCC |
| H2B 10-33 | 32 | CCGAAGAAGG GCTCCAAGAA GGCCGTCACC AAGGCCCAAA AGAA |
| | | GGATGGCAAG AAGCGCAAGC GCAGCCGC |
| H2B 13-27 | 33 | GGCTCCAAGA AGGCGGTGAC CAAGACCCAG AAGAAGGGCG ACAAG |
| H2B 46-60 | 34 | AAGCAGGTGC ACCCCGACAC GGGCATCTCG TCCAAGGCCA TGGGC |
| H2B 68-82 | 35 | GACATCTTCG AGCGCATCGC CGGCGAGGCG TCGCGCCTGG CGCAC |

FIG. 27A

| HISTONE PEPTIDE AUTOEPITOPES | SEQUENCE ID NO. | NUCLEOTIDE SEQUENCE |
|---|---|---|
| H3 55-69 | 36 | CAGAAGTCCA CGGAGCTGCT GATCCGCAAG CTGCCCTTCC AGCGC |
| H3 83-97 | 37 | CGCTTCCAGA GCTCGGCCGT CATGGGCCTG CAGGAGGCGA GCGAG |
| H3 85-102 | 38 | CGAGCTCGGC CGTCATGGCG CTGCAGGAGG CGAGCGAGGC CTACCTGGTG GGG |
| H3 91-105 | 39 | GCGCTGCAGG AGGCGAGCGA GGCCTACCTG GTGGGGCTCT TCGAG |
| H3 100-114 | 40 | CTCGTGGGTC TGTTTGAGGA CACCAACCTG TGCGCCATCC ACGCC |
| H4 5-19 | 41 | AAGGGCGGGA AGGGGCTCGG CAAGGGCGGC GCCAAGCGCC ACCGC |
| H4 14-28 | 42 | GGCGCCAAGC GCCACCGCAA GGTGCTGCGC GACAACATCC AGGGC |
| H4 16-39 | 43 | AAGCGCCACC GCAAGGTGCT GCGCGACAAC ATCCAGGGCA TCACCAAGCC GGCCATCCGC CGCCTGGCGC GG |
| H4 49-63 | 44 | CTCATCTACG AGGAGACGCG CGGCGTGCTC AAGGTCTTCC TGGAG |

FIG. 27B

| HISTONE PEPTIDE AUTOEPITOPES | SEQUENCE ID NO. | NUCLEOTIDE SEQUENCE |
|---|---|---|
| H4 67-81 | 45 | CGGCGACGCCG TCACCTACAC CGAGCACGCC AAGAGGAAGA CGGTC |
| H4 71-94 | 46 | ACCTACACCG AGCACGCCAA GAGGAAGACG GTCACGGCCA TGGACGT GGTCTACGCG CTCAAGCGCC AGGGA |
| H4 73-84 | 47 | ACCGAGCACG CCAAGAGGAA GACGGTCACG GCCATGGACG TGGTC |
| H4 79-93 | 48 | AAGACGGTCA CGGCCATGGA CGTGGTCTAC GCGCTCAAGC GCCAG |
| EP-1 | 49 | TCGCAGAAGG AGGAGGAGGA GGGCGCGCAA CGTGAGAAAG AGG |
| EP-2 | 50 | GACTGGATGG AGGAGGAGGA GGGCGCGCAA CGTGAGAAAG AGG |
| H5 22-42 | 51 | TCGGGCATCGC ACCCCACCTA CTCGGAGATG ATCGGGGCGG CCAT CCGTGCGGAA AAGAGCCGC |
| H1 22-42 | 52 | TCCACGGACC ACCCCAAGTA TTCAGACATG ATCGTGGCTG CTATCCAGG CAGAGAAGAA CCGT |

FIG. 27C

SEQUENCE LISTING

<160> NUMBER OF SEQ ID NOS: 61

<210> SEQ ID NO 1
<211> LENGTH: 24
<212> TYPE: PRT
<213> ORGANISM: Artificial Sequence
<220> FEATURE:
<223> OTHER INFORMATION: Histone fragment

<400> SEQUENCE: 1

Thr Tyr Thr Glu His Ala Lys Arg Lys Thr Val Thr Ala Met Asp Val
1               5                   10                  15

Val Tyr Ala Leu Lys Arg Gln Gly
            20

<210> SEQ ID NO 2
<211> LENGTH: 15
<212> TYPE: PRT
<213> ORGANISM: Artificial Sequence
<220> FEATURE:
<223> OTHER INFORMATION: Histone fragment

<400> SEQUENCE: 2

Leu Ile Tyr Glu Glu Thr Arg Gly Val Leu Lys Val Phe Leu Glu
1               5                   10                  15

<210> SEQ ID NO 3
<211> LENGTH: 24
<212> TYPE: PRT
<213> ORGANISM: Artificial Sequence
<220> FEATURE:
<223> OTHER INFORMATION: Histone fragment

<400> SEQUENCE: 3

Lys Arg His Arg Lys Val Leu Arg Asp Asn Ile Gln Gly Ile Thr Lys
1               5                   10                  15

Pro Ala Ile Arg Arg Ile Ala Arg
            20

<210> SEQ ID NO 4
<211> LENGTH: 15
<212> TYPE: PRT
<213> ORGANISM: Artificial Sequence
<220> FEATURE:
<223> OTHER INFORMATION: Histone fragment

<400> SEQUENCE: 4

Gly Ala Lys Arg His Arg Lys Val Leu Arg Asp Asn Ile Gln Gly
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Histone fragment

<400> SEQUENCE: 5

Leu Val Gly Leu Phe Glu Asp Thr Asn Leu Cys Ala Ile His Ala
1               5                   10                  15

<210> SEQ ID NO 6
<211> LENGTH: 15
<212> TYPE: PRT

```
<213> ORGANISM: Artificial Sequence
<220> FEATURE:
<223> OTHER INFORMATION: Histone fragment

<400> SEQUENCE: 6

Lys Thr Val Thr Ala Met Asp Val Val Tyr Ala Leu Lys Arg Gln
1               5                   10                  15

<210> SEQ ID NO 7
<211> LENGTH: 24
<212> TYPE: PRT
<213> ORGANISM: Artificial Sequence
<220> FEATURE:
<223> OTHER INFORMATION: Histone fragment

<400> SEQUENCE: 7

Pro Lys Lys Gly Ser Lys Lys Ala Val Thr Lys Ala Gln Lys Lys Asp
1               5                   10                  15

Gly Lys Lys Arg Lys Arg Ser Arg
            20

<210> SEQ ID NO 8
<211> LENGTH: 15
<212> TYPE: PRT
<213> ORGANISM: Artificial Sequence
<220> FEATURE:
<223> OTHER INFORMATION: Histone fragment

<400> SEQUENCE: 8

Asp Ile Phe Glu Arg Ile Ala Gly Glu Ala Ser Arg Leu Ala His
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Histone fragment

<400> SEQUENCE: 9

Leu Arg Lys Gly Asn Tyr Ala Glu Arg Val Gly Ala Gly Ala Pro
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Histone fragment

<400> SEQUENCE: 10

Asp Asn Lys Lys Thr Arg Ile Ile Pro Arg His Leu Gln Leu Ala
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Histone fragment

<400> SEQUENCE: 11

Gln Lys Ser Thr Glu Leu Leu Ile Arg Lys Leu Pro Phe Gln Arg
1               5                   10                  15

<210> SEQ ID NO 12
```

```
<211> LENGTH: 15
<212> TYPE: PRT
<213> ORGANISM: Artificial Sequence
<220> FEATURE:
<223> OTHER INFORMATION: Histone fragment

<400> SEQUENCE: 12

Arg Phe Gln Ser Ser Ala Val Met Ala Leu Gln Glu Ala Ser Glu
1               5                   10                  15

<210> SEQ ID NO 13
<211> LENGTH: 18
<212> TYPE: PRT
<213> ORGANISM: Artificial Sequence
<220> FEATURE:
<223> OTHER INFORMATION: Histone fragment

<400> SEQUENCE: 13

Gln Ser Ser Ala Val Met Ala Leu Gln Glu Ala Ser Glu Ala Tyr Leu
1               5                   10                  15

Val Gly

<210> SEQ ID NO 14
<211> LENGTH: 15
<212> TYPE: PRT
<213> ORGANISM: Artificial Sequence
<220> FEATURE:
<223> OTHER INFORMATION: Histone fragment

<400> SEQUENCE: 14

Ala Leu Gln Glu Ala Ser Glu Ala Tyr Leu Val Gly Leu Phe Glu
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Histone fragment

<400> SEQUENCE: 15

Thr Glu His Ala Lys Arg Lys Thr Val Thr Ala Met Asp Val Val
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Histone fragment

<400> SEQUENCE: 16

Leu Gly Lys Val Thr Ile Ala Gln Gly Gly Val Leu Pro Asn Ile
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Histone fragment

<400> SEQUENCE: 17

Gly Val Leu Pro Asn Ile Gln Ala Val Leu Leu Pro Lys Lys Thr
1               5                   10                  15
```

```
<210> SEQ ID NO 18
<211> LENGTH: 15
<212> TYPE: PRT
<213> ORGANISM: Artificial Sequence
<220> FEATURE:
<223> OTHER INFORMATION: Histone fragment

<400> SEQUENCE: 18

Gln Ala Val Leu Leu Pro Lys Lys Thr Glu Ser His His Lys Ala
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Histone fragment

<400> SEQUENCE: 19

Gly Ser Lys Lys Ala Val Thr Lys Ala Gln Lys Lys Asp Gly Lys
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Histone fragment

<400> SEQUENCE: 20

Lys Gln Val His Pro Asp Thr Gly Ile Ser Ser Lys Ala Met Gly
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Histone fragment

<400> SEQUENCE: 21

Arg Asp Ala Val Thr Tyr Thr Glu His Ala Lys Arg Lys Thr Val
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Histone fragment

<400> SEQUENCE: 22

Lys Gly Gly Lys Gly Leu Gly Lys Gly Gly Ala Lys Arg His Arg
1               5                   10                  15

<210> SEQ ID NO 23
<211> LENGTH: 14
<212> TYPE: PRT
<213> ORGANISM: Artificial Sequence
<220> FEATURE:
<223> OTHER INFORMATION: Histone fragment

<400> SEQUENCE: 23

Ser Gln Lys Glu Glu Glu Gly Ala Gln Arg Glu Lys Glu
1               5                   10

<210> SEQ ID NO 24
```

```
<211> LENGTH: 14
<212> TYPE: PRT
<213> ORGANISM: Artificial sequence
<220> FEATURE:
<223> OTHER INFORMATION: Histone fragment

<400> SEQUENCE: 24

Asp Trp Met Glu Glu Glu Glu Gly Ala Gln Arg Glu Lys Glu
1               5                   10

<210> SEQ ID NO 25
<211> LENGTH: 21
<212> TYPE: PRT
<213> ORGANISM: Artificial sequence
<220> FEATURE:
<223> OTHER INFORMATION: Histone fragment

<400> SEQUENCE: 25

Ser Ala Ser His Pro Thr Tyr Ser Glu Met Ile Ala Ala Ala Ile Arg
1               5                   10                  15

Ala Glu Lys Ser Arg
            20

<210> SEQ ID NO 26
<211> LENGTH: 21
<212> TYPE: PRT
<213> ORGANISM: Artificial sequence
<220> FEATURE:
<223> OTHER INFORMATION: Histone fragment

<400> SEQUENCE: 26

Ser Thr Asp His Pro Lys Tyr Ser Asp Met Ile Val Ala Ala Ile Gln
1               5                   10                  15

Ala Glu Lys Asn Arg
            20

<210> SEQ ID NO 27
<211> LENGTH: 47
<212> TYPE: DNA
<213> ORGANISM: Artificial sequence
<220> FEATURE:
<223> OTHER INFORMATION: Histone fragment

<400> SEQUENCE: 27
ctgcggaaag gtaactacgc ggagcgggtg ggggccggag cgcccgt            47

<210> SEQ ID NO 28
<211> LENGTH: 46
<212> TYPE: DNA
<213> ORGANISM: Artificial sequence
<220> FEATURE:
<223> OTHER INFORMATION: Histone fragment

<400> SEQUENCE: 28
gacaacaaga agacgcgcat catcccccgc cacctgcagc tggcca             46

<210> SEQ ID NO 29
<211> LENGTH: 45
<212> TYPE: DNA
<213> ORGANISM: Artificial sequence
<220> FEATURE:
<223> OTHER INFORMATION: Histone fragment

<400> SEQUENCE: 29
ctgggccgcg tgaccatcgc gcagggcggc gtcctgccca acatc              45
```

<210> SEQ ID NO 30
<211> LENGTH: 45
<212> TYPE: DNA
<213> ORGANISM: Artificial sequence
<220> FEATURE:
<223> OTHER INFORMATION: Histone fragment

<400> SEQUENCE: 30
ggcgtcctgc ccaacatcca ggccgtgctg ctgcccaaga agacc          45

<210> SEQ ID NO 31
<211> LENGTH: 45
<212> TYPE: DNA
<213> ORGANISM: Artificial sequence
<220> FEATURE:
<223> OTHER INFORMATION: Histone fragment

<400> SEQUENCE: 31
caggccgtgc tgctgcccaa gaagaccgag agccaccaca aggcc          45

<210> SEQ ID NO 32
<211> LENGTH: 72
<212> TYPE: DNA
<213> ORGANISM: Artificial sequence
<220> FEATURE:
<223> OTHER INFORMATION: Histone fragment

<400> SEQUENCE: 32
ccgaagaagg gctccaagaa ggccgtcacc aaggcccaaa agaaggatgg caagaagcgc          60
aagcgcagcc gc          72

<210> SEQ ID NO 33
<211> LENGTH: 45
<212> TYPE: DNA
<213> ORGANISM: Artificial sequence
<220> FEATURE:
<223> OTHER INFORMATION: Histone fragment

<400> SEQUENCE: 33
ggctccaaga aggcggtgac caagacccag aagaagggcg acaag          45

<210> SEQ ID NO 34
<211> LENGTH: 45
<212> TYPE: DNA
<213> ORGANISM: Artificial sequence
<220> FEATURE:
<223> OTHER INFORMATION: Histone fragment

<400> SEQUENCE: 34
aagcaggtgc accccgacac gggcatctcg tccaaggcca tgggc          45

<210> SEQ ID NO 35
<211> LENGTH: 45
<212> TYPE: DNA
<213> ORGANISM: Artificial sequence
<220> FEATURE:
<223> OTHER INFORMATION: Histone fragment

<400> SEQUENCE: 35
gacatcttcg agcgcatcgc cggcgaggcg tcgcgcctgg cgcac          45

<210> SEQ ID NO 36
<211> LENGTH: 45
<212> TYPE: DNA
<213> ORGANISM: Artificial sequence

```
<220> FEATURE:
<223> OTHER INFORMATION: Histone fragment

<400> SEQUENCE: 36
cagaagtcca cggagctgct gatccgcaag ctgcccttcc agcgc          45

<210> SEQ ID NO 37
<211> LENGTH: 45
<212> TYPE: DNA
<213> ORGANISM: Artificial sequence
<220> FEATURE:
<223> OTHER INFORMATION: Histone fragment

<400> SEQUENCE: 37
cgcttccaga gctcggccgt catggcgctg caggaggcga gcgag          45

<210> SEQ ID NO 38
<211> LENGTH: 53
<212> TYPE: DNA
<213> ORGANISM: Artificial sequence
<220> FEATURE:
<223> OTHER INFORMATION: Histone fragment

<400> SEQUENCE: 38
cgagctcggc cgtcatggcg ctgcaggagg cgagcgaggc ctacctggtg ggg     53

<210> SEQ ID NO 39
<211> LENGTH: 45
<212> TYPE: DNA
<213> ORGANISM: Artificial sequence
<220> FEATURE:
<223> OTHER INFORMATION: Histone fragment

<400> SEQUENCE: 39
gcgctgcagg aggcgagcga ggcctacctg gtggggctct tcgag          45

<210> SEQ ID NO 40
<211> LENGTH: 45
<212> TYPE: DNA
<213> ORGANISM: Artificial sequence
<220> FEATURE:
<223> OTHER INFORMATION: Histone fragment

<400> SEQUENCE: 40
ctcgtgggtc tgtttgagga caccaacctg tgcgccatcc acgcc          45

<210> SEQ ID NO 41
<211> LENGTH: 45
<212> TYPE: DNA
<213> ORGANISM: Artificial sequence
<220> FEATURE:
<223> OTHER INFORMATION: Histone fragment

<400> SEQUENCE: 41
aagggcggga aggggctcgg caagggcggc gccaagcgcc accgc          45

<210> SEQ ID NO 42
<211> LENGTH: 45
<212> TYPE: DNA
<213> ORGANISM: Artificial sequence
<220> FEATURE:
<223> OTHER INFORMATION: Histone fragment

<400> SEQUENCE: 42
ggcgccaagc gccaccgcaa ggtgctgcgc gacaacatcc agggc          45
```

<210> SEQ ID NO 43
<211> LENGTH: 72
<212> TYPE: DNA
<213> ORGANISM: Artificial sequence
<220> FEATURE:
<223> OTHER INFORMATION: Histone fragment

<400> SEQUENCE: 43
aagcgccacc gcaaggtgct gcgcgacaac atccagggca tcaccaagcc ggccatccgc    60
cgcctggcgc gg                                                        72

<210> SEQ ID NO 44
<211> LENGTH: 45
<212> TYPE: DNA
<213> ORGANISM: Artificial sequence
<220> FEATURE:
<223> OTHER INFORMATION: Histone fragment

<400> SEQUENCE: 44
ctcatctacg aggagacgcg cggcgtgctc aaggtcttcc tggag                    45

<210> SEQ ID NO 45
<211> LENGTH: 45
<212> TYPE: DNA
<213> ORGANISM: Artificial sequence
<220> FEATURE:
<223> OTHER INFORMATION: Histone fragment

<400> SEQUENCE: 45
cgcgacgccg tcacctacac cgagcacgcc aagaggaaga cggtc                    45

<210> SEQ ID NO 46
<211> LENGTH: 72
<212> TYPE: DNA
<213> ORGANISM: Artificial sequence
<220> FEATURE:
<223> OTHER INFORMATION: Histone fragment

<400> SEQUENCE: 46
acctacaccg agcacgccaa gaggaagacg gtcacggcca tggacgtggt ctacgcgctc    60
aagcgccagg ga                                                        72

<210> SEQ ID NO 47
<211> LENGTH: 45
<212> TYPE: DNA
<213> ORGANISM: Artificial sequence
<220> FEATURE:
<223> OTHER INFORMATION: Histone fragment

<400> SEQUENCE: 47
accgagcacg ccaagaggaa gacggtcacg gccatggacg tggtc                    45

<210> SEQ ID NO 48
<211> LENGTH: 45
<212> TYPE: DNA
<213> ORGANISM: Artificial sequence
<220> FEATURE:
<223> OTHER INFORMATION: Histone fragment

<400> SEQUENCE: 48
aagacggtca cggccatgga cgtggtctac gcgctcaagc gccag                    45

<210> SEQ ID NO 49
<211> LENGTH: 43

```
<212> TYPE: DNA
<213> ORGANISM: Artificial sequence
<220> FEATURE:
<223> OTHER INFORMATION: Histone fragment

<400> SEQUENCE: 49
tcgcagaagg aggaggagga gggcgcgcaa cgtgagaaag agg           43

<210> SEQ ID NO 50
<211> LENGTH: 43
<212> TYPE: DNA
<213> ORGANISM: Artificial sequence
<220> FEATURE:
<223> OTHER INFORMATION: Histone fragment

<400> SEQUENCE: 50
gactggatgg aggaggagga gggcgcgcaa cgtgagaaag agg           43

<210> SEQ ID NO 51
<211> LENGTH: 63
<212> TYPE: DNA
<213> ORGANISM: Artificial sequence
<220> FEATURE:
<223> OTHER INFORMATION: Histone fragment

<400> SEQUENCE: 51
tcggcatcgc accccaccta ctcggagatg atcgcggcgg ccatccgtgc ggaaaagagc    60
cgc                                                                  63

<210> SEQ ID NO 52
<211> LENGTH: 63
<212> TYPE: DNA
<213> ORGANISM: Artificial sequence
<220> FEATURE:
<223> OTHER INFORMATION: Histone fragment

<400> SEQUENCE: 52
tccacggacc accccaagta ttcagacatg atcgtggctg ctatccaggc agagaagaac    60
cgt                                                                  63

<210> SEQ ID NO 53
<211> LENGTH: 10
<212> TYPE: PRT
<213> ORGANISM: Artificial sequence
<220> FEATURE:
<223> OTHER INFORMATION: Histone fragment

<400> SEQUENCE: 53

Met Ile Ala Ala Ala Ile Arg Ala Glu Lys
1               5                   10

<210> SEQ ID NO 54
<211> LENGTH: 21
<212> TYPE: PRT
<213> ORGANISM: Artificial sequence
<220> FEATURE:
<223> OTHER INFORMATION: Histone fragment

<400> SEQUENCE: 54

Ser Ala Ser His Pro Thr Tyr Ser Glu Met Ile Ala Ala Ala Ile Arg
1               5                   10                  15

Ala Glu Lys Ser Arg
            20
```

```
<210> SEQ ID NO 55
<211> LENGTH: 13
<212> TYPE: PRT
<213> ORGANISM: Artificial sequence
<220> FEATURE:
<223> OTHER INFORMATION: Histone fragment

<400> SEQUENCE: 55

Glu Met Ile Ala Ala Ala Ile Arg Ala Glu Lys Ser Arg
1               5                   10

<210> SEQ ID NO 56
<211> LENGTH: 11
<212> TYPE: PRT
<213> ORGANISM: Artificial sequence
<220> FEATURE:
<223> OTHER INFORMATION: Histone fragment

<400> SEQUENCE: 56

Ile Ala Ala Ala Ile Arg Ala Glu Lys Ser Arg
1               5                   10

<210> SEQ ID NO 57
<211> LENGTH: 15
<212> TYPE: PRT
<213> ORGANISM: Artificial Sequence
<220> FEATURE:
<223> OTHER INFORMATION: Histone fragment

<400> SEQUENCE: 57

Ala Met Gly Ile Met Asn Ser Phe Val Asn Asp Ile Phe Glu Arg
1               5                   10                  15

<210> SEQ ID NO 58
<211> LENGTH: 12
<212> TYPE: PRT
<213> ORGANISM: Artificial sequence
<220> FEATURE:
<223> OTHER INFORMATION: Histone fragment

<400> SEQUENCE: 58

Ser Glu Met Ile Ala Ala Ala Ile Arg Ala Glu Lys
1               5                   10

<210> SEQ ID NO 59
<211> LENGTH: 20
<212> TYPE: PRT
<213> ORGANISM: Artificial sequence
<220> FEATURE:
<223> OTHER INFORMATION: Histone fragment

<400> SEQUENCE: 59

Ser Ala Ser His Pro Thr Tyr Ser Glu Met Ile Ala Ala Ala Ile Arg
1               5                   10                  15

Ala Glu Lys Ser
            20

<210> SEQ ID NO 60
<211> LENGTH: 16
<212> TYPE: PRT
<213> ORGANISM: Artificial sequence
<220> FEATURE:
<223> OTHER INFORMATION: Histone fragment

<400> SEQUENCE: 60

Ser Ala Ser His Pro Thr Tyr Ser Glu Met Ile Ala Ala Ala Ile Arg
1               5                   10                  15
```

```
<210> SEQ ID NO 61
<211> LENGTH: 13
<212> TYPE: PRT
<213> ORGANISM: Artificial sequence
<220> FEATURE:
<223> OTHER INFORMATION: Histone fragment

<400> SEQUENCE: 61

Lys Pro Ala Gly Pro Ser Val Thr Glu Leu Ile Thr Lys
1               5                   10
```

LOCALIZATION OF MAJOR PEPTIDE AUTOEPITOPES FOR NUCLEOSOME SPECIFIC T CELLS OF SYSTEMIC LUPUS ERYTHEMATOSUS

CROSS-REFERENCE TO RELATED APPLICATIONS

This application is entitled to priority pursuant to 35 U.S.C. §119(e) to U.S. Provisional Patent Application No. 60/131,448, which was filed on Apr. 28, 1999.

STATEMENT REGARDING FEDERALLY SUPPORTED RESEARCH AND DEVELOPMENT

This invention was made in part using funds obtained from the U.S. Government (National Institutes of Health Grant Nos. RO1 AR 39157 and RO1 AI 41985) and the U.S. Government may therefore have certain rights in the invention.

BACKGROUND OF THE INVENTION

Nucleosome-specific T helper cells (Th cells) initiate and sustain the production of pathogenic, anti-nuclear autoantibodies during the onset and progression of systemic lupus erythematosus (SLE) through cognate interaction with autoimmune B cells (Mohan et al., 1993, J. Exp. Med. 177:1367; Desai-Mehta et al., 1995, J. Clin. Invest. 95:53; Kaliyaperumal et al., 1996, J. Exp. Med. 183:2459; Shi et al., 1998, J. Exp. Med. 187:367; Voll et al., 1997, Arthritis Rheum. 40:2162; Kretz-Rommel, et al., 1997, J. Clin. Invest. 99:1888). These SLE-associated Th cells are primarily responsible for driving the pathogenic autoimmune response. Without the help provided by these Th cells, autoimmune B cells are unable to produce the disease-causing (pathogenic) autoantibodies associated with SLE. Some of the critical epitopes (i.e. autoantigenic determinants) to which these Th cells are directed have been localized to the histone proteins of nucleosomes (i.e. DNA-protein complexes in the nuclei of animal cells). For example, in lupus prone mice, SLE-associated autoepitopes have been identified at amino acid positions 10–33 of the H2B histone protein, at amino acid positions 85–102 of the H3 histone protein, and at amino acid positions 16–39 and 71–94 of the H4 histone protein (Kaliyaperumal et al., 1996, J. Exp. Med. 183:2459).

SLE-associated autoimmune B cells recognize and bind autoantigenic determinants in DNA, histones, or other proteins in nucleosomes through surface molecules (i.e. B cell receptors, BCRs) which are antibody (i.e. immunoglobulin or Ig) receptors. Autoantigenic recognition and binding by an autoimmune B cell is followed by endocytosis and processing of the entire nucleosome particle which bears the recognized autoantigen. As illustrated in FIG. 1, the processed histone autoepitope (i.e. a histone peptide) is loaded onto a major histocompatibility complex class II molecule (i.e. a MHC class II molecule or I-$A^d$ molecule) of the B cell, and is presented as a complex on the surface of the B cell in an interaction with an autoimmune Th cell which has receptors specific for nucleosomal histone peptide autoepitopes. Upon receiving this antigen-specific signal (i.e. signal 1) and other co-stimulatory signals (i.e. signal 2) from the B cell, the autoimmune Th cell helps the autoimmune B cell by recruiting intermolecular support and enabling the B cell to survive and differentiate into an autoantibody-producing B cell associated with SLE (Datta and Kaliyaperumal, 1997, Ann. New York Acad. Sci. 815:155; Datta, 2000, Nature Med. 6:259).

Autoimmune T cells of lupus-prone mice are spontaneously primed to SLE-associated autoepitopes early in life before overt autoantibody production or any clinical manifestations of the disease are present (Kaliyaperumal et al., 1996, J. Exp. Med. 183:2459). Moreover, immunization of pre-autoimmune mice with peptides corresponding to SLE-associated nucleosomal autoepitopes precipitates SLE-associated nephritis by triggering autoimmune T helper cells of subtype 1 (i.e. Th 1 cells) which, in turn, initiate anti-nuclear autoantibody production (Kaliyaperumal et al., 1996, J. Exp. Med. 183:2459). The T helper cell subtypes 2 and 0 (i.e., Th2 and Th0 cells, respectively) are also involved in the progression of SLE, as these T helper cell subtypes maintain autoantibody production (Mohan et al., 1993, J. Exp. Med. 177:1367; Nakajima et al., 1997, J. Immunol. 158:1466).

Unlike organ-specific autoimmune diseases in which the autoimmune response targets a restricted set of autoepitoes and is mediated by a single population of T cells, the autoimmune response in SLE involves a complex web of polyclonal T cell and B cell hyperactivity and appears to be directed by multiple susceptibility genes (Datta et al., 1982, J. Immunol. 129:1539; Klinman and Steinberg, 1987, J. Exp. Med. 165:1755; Cohen and Eisenberg, 1991, Ann. Rev. Immunol. 9:243; Chan and Shlomchik, 1998, J. Immunol. 160:51; Jongstra-Bilen, 1997, J. Immunol. 159:5810; Mohan et al., 1995, J. Immunol. 154:1470; Desai-Mehta, 1996, J. Clin. Invest. 97:2063; Koshy et al., 1996, J. Clin. Invest. 98:826; Liossis, et al., 1996, J. Clin. Invest. 98:2549; Wakeland et al., 1997, J. Clin. Immunol. 17:272; Vyse and Kotzin 1996, Opin. Immunol. 8:843; Kono and Theofilopoulos, 1996, J. Autoimmunity 9:437).

Previously, it has not been considered that a brief tolerogenic regimen of nucleosomal peptides could delay the development of SLE-associated nephritis. Moreover, chronic tolerogenic therapy with peptides has not previously been pursued, as it was not foreseen that such therapy might have the effect of prolonging survival and slowing SLE progression. There has long been a need in the art to identify immunololgically specific agents which could significantly affect the therapeutic outcome of SLE by delaying or preventing the onset and progression of the disease and complications thereof. The present invention provides a novel therapeutic approach to satisfying this need.

SUMMARY OF THE INVENTION

The present invention provides a composition comprising an isolated peptide which has an amino acid sequence corresponding to the amino acid sequence of a portion of a nucleosome histone protein and, and which is capable of promoting immunological tolerance in an animal having systemic lupus erythematosus.

The invention includes an isolated peptide which has an amino acid sequence corresponding to the amino acid sequence of a portion of a nucleosome histone protein, wherein the portion of the nucleosome histone protein corresponds to an autoepitope which is associated with systemic lupus erythematosus and which is recognized by one or more of an autoimmune T cell and an autoimmune B cell.

In one embodiment, the isolated peptide can correspond in amino acid sequence to a nucleosome histone protein which is selected from the group consisting of histone 1 (H1), histone 2A (H2A), histone 2B (H2B), histone 3 (H3), and histone 4 (H4).

In multiple embodiments, the isolated peptide comprises not more than 27 contiguous amino acids and has an amino acid sequence selected from the group consisting of SEQ ID NOs: 1, 2, 3, 4, 5, 6, 7, 8, 9, 10, 11, 12, 13, 14, 15, 16, 17, 18, 19, 20, 21, 22, 23, 24, 25, and 26.

In other embodiments, the isolated peptide can further comprise a covalently attached moiety selected from the group consisting of a fluorophore, a chromophore, a biotin moiety, a light reactive group, and an enzyme cleavable group.

In one aspect, the invention includes a composition comprising a pharmaceutically acceptable carrier and an isolated peptide which has an amino acid sequence corresponding to the amino acid sequence of a portion of a nucleosome histone protein and, and which is capable of promoting immunological tolerance in an animal having systemic lupus erythematosus.

In another aspect, the invention includes an isolated nucleic acid encoding an isolated peptide which has an amino acid sequence corresponding to the amino acid sequence of a portion of a nucleosome histone protein and, and which is capable of promoting immunological tolerance in an animal having systemic lupus erythematosus. In this aspect, the isolated nucleic acid can comprise a nucleotide sequence selected from the group consisting of SEQ ID NOS.: 27, 28, 29, 30, 31, 32, 33, 34, 35, 36, 37, 38, 39, 40, 41, 42, 43, 44, 45, 46, 47, 48, 49, 50, 51 and 52. Also included in this aspect of the invention is a vector comprising the isolated nucleic acid.

In multiple embodiments the isolated nucleic acid of the invention comprises a nucleotide sequence selected from the group consisting of SEQ ID NOS.: 27, 28, 29, 30, 31, 32, 33, 34, 35, 36, 37, 38, 39, 40, 41, 42, 43, 44, 45, 46, 47, 48, 49, 50, 51 and 52.

The invention also includes a cell comprising an isolated nucleic acid encoding an isolated peptide which has an amino acid sequence corresponding to the amino acid sequence of a portion of a nucleosome histone protein and, and which is capable of promoting immunological tolerance in an animal having systemic lupus erythematosus.

In multiple embodiments, the cell comprising the isolated nucleic acid is selected from the group consisting of a prokaryotic cell and a eukaryotic cell. In one embodiment, the cell is an insect cell.

The invention additionally includes a method of treating an animal having an autoimmune disorder. This method comprises administering to the animal an isolated peptide comprising a portion of a nucleosome histone protein, wherein the isolated peptide is capable of promoting immunological tolerance in an animal, thereby treating the autoimmune disorder in the animal.

In multiple embodiments, the autoimmune disorder is selected from the group consisting of rheumatoid arthritis, scleroderma, and systemic lupus erythematosus.

In other embodiments, the isolated peptide is administered in an amount which is from at least about 10 micrograms per kilogram of animal to at least about 1 gram per kilogram of animal, and from at least about 100 micrograms per kilogram of animal to about 600 micrograms per kilogram of animal.

In still other embodiments, the isolated peptide comprises not more than 27 contiguous amino acids and having an amino acid sequence selected from the group consisting of SEQ ID NOs: 1, 2, 3, 4, 5, 6, 7, 8, 9, 10, 11, 12, 13, 14, 15, 16, 17, 18, 19, 20, 21, 22, 23, 24, 25, and 26.

Alternatively, the method of treating an animal having an autoimmune disorder comprises administering to the animal a modified histone peptide, wherein the modified histone peptide is an altered peptide ligand, and wherein the modified histone peptide is capable of promoting immunological tolerance in the animal, thereby treating the autoimmune disorder. In various embodiments of this method, the autoimmune disorder is selected from the group consisting of rheumatoid arthritis, scleroderma, and systemic lupus erythematosus, and the isolated peptide is administered in an amount which is from at least about 10 micrograms per kilogram of animal to at least about 1 gram per kilogram of animal, and from at least about 100 micrograms per kilogram of animal to about 600 micrograms per kilogram of animal.

In other embodiments, the modified peptide comprises not more than 27 contiguous amino acids and has an amino acid sequence which is at least one amino acid different relative to an amino acid sequence selected from the group consisting of SEQ ID NOs: 1, 2, 3, 4, 5, 6, 7, 8, 9, 10, 11, 12, 13, 14, 15, 16, 17, 18, 19, 20, 21, 22, 23, 24, 25, and 26.

The invention includes a method of treating nephritis in an animal having systemic lupus erythematosus. This method comprises administering to the animal an isolated peptide comprising a portion of a nucleosome histone protein, wherein the isolated peptide is capable of promoting immunological tolerance in an animal, thereby alleviating the nephritis in the animal. Alternatively, this method comprises administering to the animal a modified histone peptide, wherein the modified histone peptide is an altered peptide ligand, and wherein the modified histone peptide is capable of promoting immunological tolerance in the animal, thereby alleviating the nephritis in the animal.

The invention encompasses a method of reducing the production of autoantibodies in an animal. This method comprises administering to the animal an isolated peptide comprising a portion of a nucleosome histone protein, wherein the isolated peptide is capable of promoting immunological tolerance in an animal, and wherein the peptide is administered in an amount sufficient to promote immunologic tolerance in the animal, thereby reducing the production of autoantibodies in the animal. Alternatively, this method comprises administering to said animal a modified histone peptide, wherein the modified histone peptide is an altered peptide ligand capable of promoting immunological tolerance in an animal, and wherein the modified histone peptide is administered in an amount sufficient to promote immunologic tolerance in the animal, thereby reducing the production of autoantibodies in the animal.

In another aspect, the invention encompasses a method of treating inflammation in an animal, which inflammation is caused by the production of autoantibodies in the animal. This method comprises administering to the animal an isolated peptide comprising a portion of a nucleosome histone protein, wherein the isolated peptide is capable of promoting immunological tolerance in an animal, and wherein the peptide is administered in an amount sufficient to promote immunological tolerance in the animal, thereby inhibiting the production of autoantibodies in the animal and alleviating inflammation in the animal. Alternatively, this method comprises administering to the animal a modified histone peptide, wherein the modified histone peptide is an altered peptide ligand capable of promoting immunological tolerance in an animal, and wherein the modified histone peptide is administered in an amount sufficient to promote immunological tolerance in the animal, thereby inhibiting the production of autoantibodies in the animal and alleviating inflammation in the animal.

In multiple embodiments, the invention provides a method of diagnosing systemic lupus erythematosus in an animal. This method comprises (a) contacting a sample from the animal with a composition comprising an isolated histone peptide complex, wherein said histone peptide complex comprises i) a histone peptide portion, histone peptide portion comprising no more than 27 contiguous amino acids and having an amino acid sequence corresponding to a portion of a nucleosome histone protein;

ii) a fused portion having an amino acid sequence which corresponds to a portion of a protein selected from the group consisting of a major histocompatibility class II molecule and an immunoglobin; and compatible iii) an indicator portion, wherein said indicator portion is a molecule which is capable of producing a detectable chemical signal, and which is selected from the group consisting of a flourophore, a chromophore, a light reactive moiety and a biotin moiety; and wherein each of said histone peptide portion, said fused portion, and said indication portion is covalently linked to at least one other component of the histone peptide complex; and (b) identifying in the animal the signal produced by the indicator portion, whereby the identification of the signal in the animal is an indication that the animal has systemic lupus erythematosus, thereby diagnosing systemic lupus erythematosus in the animal. In other embodiments, the invention includes a method of tracking an autoimmune cell associated with systemic lupus erythematosus in an animal. This method comprises (a) contacting a sample from the animal with a composition comprising one or more of a modified histone peptide and an isolated histone peptide complex, wherein the modified histone peptide comprises (i) an modified portion wherein said modified portion is a molecule which is capable of producing a detectable chemical signal, and which is selected from the group consisting of a flourophore, a chromophore, a light reactive moiety and a biotin moiety; and (ii) a peptide portion comprising not more than 27 contiguous amino acids and having an amino acid sequence corresponding to a nucleosome histone protein, and wherein the peptide portion and the modified portion are covalently linked; and wherein the histone peptide complex comprises (iii) a histone peptide portion, comprising no more than 27 contiguous amino acids and having an amino acid sequence corresponding to a portion of a nucleosome histone protein, (iv) a fused portion having an amino acid sequence which corresponds to a portion of a protein selected from the group consisting of a major histocompatibility class II molecule and an immunoglobin, and (v) an indicator portion, wherein the indicator portion is a molecule which is capable of producing a detectable chemical signal, and which is selected from the group consisting of a flourophore, a chromophore, a light reactive moiety and a biotin moiety; and wherein each of the histone peptide portion, the fused portion, and the indicator portion is covalently linked to at least one other component of the histone peptide complex; and (b) identifying and monitoring in the animal the signal produced by the indicator portion, wherein the identification and monitoring of the signal in the animal constitutes the identification and monitoring of an autoimmune cell associated with systemic lupus erythematosus to which the histone protein complex is bound, thereby tracking the autoimmune cell associated with systemic lupus erythematosus in the animal.

BRIEF DESCRIPTION OF THE DRAWINGS

FIGS. 4A–4C, is a series of graphs depicting the effect of IL-2 on the ability of T cells obtained from treated mice to facilitate autoantibody production by autoimmune B cells. The concentration of rIL-2 used in these experiments was 100 units per milliliter of culture medium. The results are expressed as a mean number of antibody units per deciliter of culture medium±SEM of five experiments.

FIG. 9, comprising FIGS. 9A–9D, is a series of graphs depicting IgG autoantibody levels in the serum of peptide-injected mice. Sera from SNF$_1$ mice were assayed for levels of IgG autoantibodies to dsDNA (FIG. 9A), ssDNA (FIG. 9B), nucleosomes (FIG. 9C), and histones (FIG. 9D). Sera were obtained for these analyses at the start of peptide injections, and at 36 weeks of age. The results are expressed as a mean number of antibody units per deciliter of serum±SEM of five experiments.

FIG. 12, comprising

FIG. 13, comprising FIG. 13A depicts a dose response curve of a representative SLE-associated T cell line. IL-2 production by this T cell line was observed during co-culture with autologous EBV-B cells acting as APCs which were pre-incubated with selected concentrations of the histone peptide, H4$_{49-63}$. FIG. 13B depicts an example of MHC class II, HLADR-dependent recognition of nucleosomal peptides by an SLE-associated Th cell line. In this figure, stimulation with concentrations of peptide from 0.01 micromolar to 100 micromolar exhibited significant differences (p<0.05 at 0.01 μM, Student's test) relative to background level of T cells cultured with APC and without peptide. Presentation of the H4$_{49-63}$ peptide by autologous EBV-B cells to the short-term T cell line L-EB, was inhibited mainly by anti-DR mAb.

FIG. 14, comprising

FIG. 15, comprising

FIG. 16, comprising In FIG. 16D, the bar labeled "Nuc" represents the mean value of responses for all ten cell lines to a whole nucleosome preparation.

FIG. 17 is a table which lists the amino acid sequences of histone peptides that correspond to SLE-associated autoepitope regions identified using SLE-associated T-cell lines described herein, particularly in Examples 2 and 3.

FIG. 18, comprising FIG. 18A illustrates IFN-γ and IL-10 production in patient R-WG in response to stimulation by either anti-CD3, nucleosomes or one of the histone peptides. FIG. 18B depicts IL-2 and IL-4 production in patient R-SC in response to stimulation by anti-CD3, nucleosomes, or selected histone peptides. Demarcation of the quadrants was based on background staining of the T cells cultured in medium alone without stimulation.

FIG. 19, comprising FIGS. 19A and 19B, is a table which lists the data from flow cytometry experiments performed using intracellular cytokine staining of viable, CD4$^+$ T cells of the peripheral blood from each of twelve SLE patients. A T cell response to a histone peptide was considered positive when the percent of positive cells from a given patient sample was two times greater than the percent of positive cells in the background sample (i.e. a sample comprised of cells cultured in medium only), and when at least 0.2% of the total viable CD4$^+$ T cells in the patient sample were stained positive. A positive response is indicated by outlined and bold numbers.

FIG. 21 is a table indicating the frequency of SLE patients whose T cells responded to histone peptide epitopes. Patients listed correspond to those listed in FIG. 19. Bold, outlined numbers indicate histone peptides to which 50% or more of patients responded. Bold, italicized numbers indicate histone peptides to which at least 40% of patients responded.

FIG. 22 is a table which lists human MHC II-{HLA-DR} binding motifs in histone autoepitopes. The autoepitopes shown in FIG. 21 which were identified as being recurrently recognized by SLE-associated T cells, were aligned with various known HLA-DR-binding motifs (Southwood et al., 1998, Immunol. 160:3363–3373; Chicz et al., 1993, Exp. Med. 178:27–47; Chicz et al., 1992, Nature 358:764–768). Underlining indicates amino acids which are anchor residues (i.e. amino acids which interact directly with residues in the MHC II groove. $H4_{71-94}$ also contains the binding motif for HLA-DR alleles, 1, 3, 4, 5, 7, and 8, in addition to those shown.

FIG. 23, comprising FIG. 23A depicts an analysis using high-performance liquid chromatography (HPLC) of peptides eluted from mouse $I-A^d$ molecules obtained from a chromatin pulsed APC line. Peptides having molecular weights of less than 3,000 Daltons were purified by elution through a C-18 column using acetonitrile and a solution comprising water and 0.1% trifluoroacetic acid (TFA). FIG. 23B is a graph depicting IL-2 release by a representative, SLE-associated pathogenic Th clone, L-3A, after stimulation with HPLC-purified histone peptides, using the A20 cell line as APCs. FIG. 23C depicts a mass spectral analysis of one of the stimulatory fractions (#23) from HPLC purification.

FIG. 25, comprising FIG. 25A depicts the results of a helper assay performed using Th clone 5E9. FIG. 25B depicts the results of a helper assay performed using Th clone 1D12. FIG. 25C depicts the results of a helper assay performed using Th clone 3F6. FIG. 25D depicts the results of a helper assay performed using Th clone 1 G1, which is known to respond only to nucleosome preparations, not to individual, naturally processed peptides.

FIG. 27 is a table which lists the nucleotide sequences (SEQ ID Nos: 27–52) that encode histone peptides described herein (SEQ ID Nos: 1–26).

DETAILED DESCRIPTION

Figure 1:
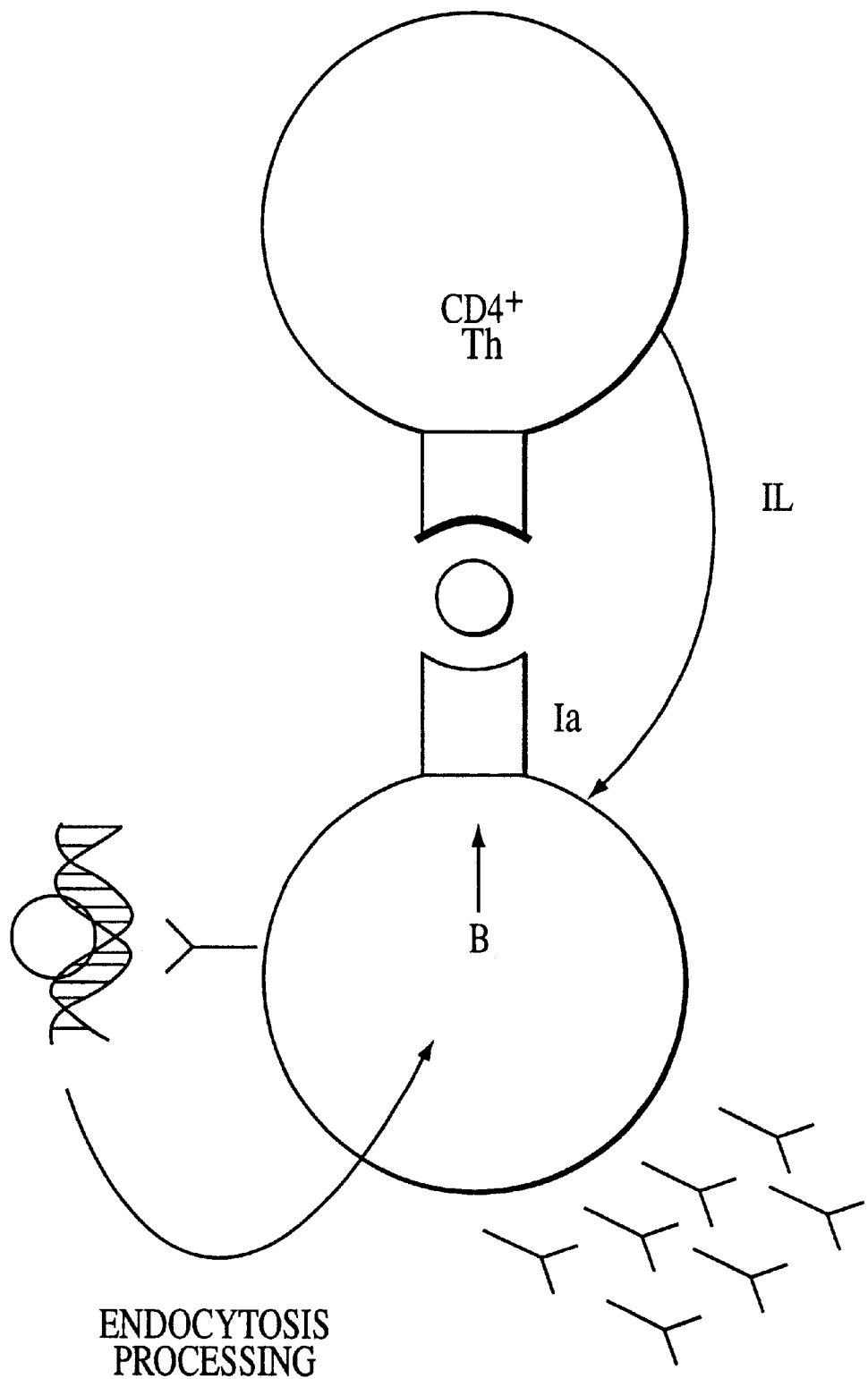
FIG. 1 is a diagram depicting the mechanism by which an autoimmune T helper cell ($CD^+4$ Th) drives the production of SLE-associated autoantibodies by autoimmune B cells. For simplicity, costimulatory signaling molecules are not shown. In this figure, Ia refers to the MHC class II molecule-autoantigenic peptide complex, and IL refers to interleukins.

The invention relates to the discovery that certain peptides derived from nucleosomal histone proteins are useful for delaying the onset and progression of nephritis associated with systemic lupus erythematosus (i.e. lupus or SLE). The invention includes a series of peptides which span specific regions of the histone proteins (i.e. H1, H2A, H2B, H3, and H4), and additionally encompasses isolated nucleic acids encoding histone peptides for the production of same, modified histone peptides, such as biotinylated histone peptides, amino acid-substituted histone peptides, and altered peptide ligands (APLs), and histone peptide complexes, such as histone peptide/MHC II (major histocompatability complex class II) tetramer complexes and histone peptide/MHC II-Ig (Immunoglobin) chimeric dimer complexes. The invention further encompasses pharmaceutical compositions which comprise one or more of a histone peptide, a modified histone peptide, a histone peptide complex, and an isolated nucleic acid encoding a histone peptide. The histone peptides, modified histone peptides, and histone peptide complexes described herein are therapeutically useful as compositions for the treatment of SLE and complications thereof. The isolated nucleic acids encoding the peptides are useful as described herein for the production of histone peptides and histone peptide complexes, and for tracking, in vivo, SLE-associated T and B cells.

The invention further provides methods of using histone peptides or modified histone peptides to promote tolerance to SLE-associated autoepitopes in an animal, inhibit production of autoantibodies in an animal, inhibit an autoimmune response and associated inflammation in an animal, and treat disorders in an animal which are related to the production of autoantibodies and complications thereof, such as inflammatory diseases, autoimmune disorders, and nephritis. The invention encompasses methods of using one or more of modified histone peptides, histone peptide complexes, and isolated nucleic acid encoding histone peptides or histone peptide complexes to track SLE-associated T cells and SLE associated B cells, and to diagnose SLE in an animal. The invention also provides methods of making modified histone peptides and histone peptide complexes.

Additionally, the invention provides kits which comprise one or more of a histone peptide, a modified histone peptide, a histone peptide complex, and an instructional material. The kits provided by the invention are useful for tracking SLE-associated T and B cells, promoting tolerance to SLE-associated autoepitopes, inhibiting the production of autoantibodies, inhibiting an immune response and associated inflammation, treating SLE or other autoimmune disorders and complications thereof, and in the diagnosis and prognostication of SLE in an animal.

Definitions

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

As used herein, amino acid residues are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

Unless otherwise indicated, all amino acid sequences listed in this disclosure are listed in the order from the amino terminus to the carboxyl terminus.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

An "isolated nucleic acid", as used herein, refers to a nucleic acid sequence, segment, or fragment which has been purified from the sequences which flank it in a naturally occurring state, e.g., a DNA fragment which has been removed from the sequences which are normally adjacent to the fragment e.g., the sequences adjacent to the fragment in a genome in which it naturally occurs. The term also applies to nucleic acids which have been substantially purified from other components which naturally accompany the nucleic acid, e.g., RNA or DNA or proteins which naturally accompany it in the cell.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

"Complementary" as used herein, refers to the subunit sequence complementarily between two nucleic acid molecules, e.g., two DNA molecules or two RNA molecules. When a subunit position in both of the two molecules is occupied by a complementary monomeric subunit, e.g., if one position in each of two DNA molecules is occupied by adenine and the other is occupied by a thymine, then they are complementary at that position. Similarly, if one position in each of two DNA molecules is occupied by guanine and the other is occupied by a cytosine, then they too are complementary at that position. The degree of complementarity between two sequences is a direct function of the number of positions occupied by complementary bases, e.g., if half (e.g., five positions in a polymer ten subunits in length) of the positions in two compound sequences contain complementary bases then the two sequences share 50% complementarity, if 90% of the positions, e.g., 9 of 10, contain bases complementary to each other, the two sequences share 90% complementarity. By way of example, the DNA sequences 5'ATTGCC3' and 3'GGCGCC5' share 50% complementarity.

"Homologous" as used herein, refers to the subunit sequence similarity between two polymeric molecules, e.g., between two nucleic acid molecules, e.g., two DNA molecules or two RNA molecules, or between two peptide molecules. When a subunit position in both of the two molecules is occupied by the same monomeric subunit, e.g., if a position in each of two DNA molecules is occupied by adenine, then they are homologous at that position. The homology between-two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3' ATTGCC 5' and 3' TATGCG 5' share 50% homology. Any of a variety of known algorithms may be used to calculate the percent homology between two nucleic acids or two proteins of interest and these are well-known in the art.

An "isolated peptide" is a peptide which has been substantially separated from components (e.g., DNA, RNA, other proteins and peptides, carbohydrates and lipids) which naturally accompany it in a cell.

As used herein, a "15-mer" refers to an isolated peptide which comprises 15 contiguous amino acids.

As used herein, "tracking" an autoimmune T cell or B cell refers to one or more of identifying and monitoring the autoimmune T cell or B cell. Tracking as it is used herein refers to both in vivo and in vitro identification and monitoring.

A disorder is "alleviated" if one or more of the frequency, the severity, and the duration of either the disorder or a symptom of the disorder are reduced.

The term "pharmaceutically acceptable carrier" means a chemical composition with which a pharmaceutically active agent can be combined and which, following the combination, can be used to administer the agent to a subject (e.g. a mammal such as a human).

The term "physiologically acceptable" ester or salt means an ester or salt form of a pharmaceutically active agent which is compatible with any other ingredients of the pharmaceutical composition and which is not deleterious to the subject to which the composition is to be administered.

As used herein, the term "SLE-associated T cells" refers to autoimmune T cells which are involved in a pathogenic process associated with SLE. "SLE-associated nephritis" refers to inflammation of the kidney in an animal which occurs as a result of autoantibody production and which is concurrent with other symptoms of SLE.

"Autoimmune T cells" refer to T cells of an animal which are stimulated by, and provide help to mount an immune response to, antigens which are native to, or derived, from the animal itself (i.e. autoantigenic determinants or autoepitopes).

"Autoimmune B cells" refers to B cells of an animal that produce autoantibodies directed to antigenic epitopes which are native to, or derived from, the animal itself (i.e. autoepitopes).

As used herein, the term "SLE-associated autoepitope" refers to an amino acid sequence of a peptide or protein which is native to, or derived from, the animal itself, and which is recognized by, elicits a response from, or stimulates the activity of an autoimmune T cell or B cell which is involved in a pathogenic process associated with SLE.

As used herein, the term "help" refers to the interaction between a T helper cell (i.e. Th cell) and an antigen-specific B cell which results in antibody production and the recruitment of other immune cells to assist in mounting an immune response to the antigen. As an example, an autoimmune Th cell of an animal can help an autoimmune B cell of the animal which is specific for an autoantigen (i.e. an antigen which is derived from the animal itself), resulting in the production of autoantibodies. In addition, this interaction of the Th cell with B cell results in the production of cytokines and other chemotactic factors by the Th cell, which in turn, leads to the recruitment of macrophages and other immune cells, subsequent inflammation, and perpetuation of the autoimmune response.

As used herein, "tolerance" refers to an immune condition which develops in an animal by, for example, exposure to a given antigen in a certain form. Tolerance to a given antigen in an animal is generally characterized by immune responses in the animal to the antigen which are reduced with respect to one or more of numbers of recruited immune cells, incidence, intensity, and duration, relative to an animal which has not developed tolerance to the antigen.

The term "tolerogen" refers to an antigenic agent which promotes the development of tolerance in an animal. The terms "antigen" and "epitope" may be used somewhat interchangeably herein to refer to portions of histone proteins to which antibodies are directed, and which T cells recognize.

As used herein, to "load" a histone peptide onto a major histocompatibility complex class II (MHC II) molecule (i.e. an I-A$^d$ molecule) in a B cell means to cause an interaction and the formation of a complex between a histone peptide and a MHC II molecule in the B cell.

Description

Prior to the investigations described in this disclosure, the complexity of SLE has permitted only limited understanding of how the disease is initiated in an otherwise healthy animal. Further, it was not considered that autoantigen-specific, immune-based therapy would be effective in combating the disease. As a result, it has not previously been contemplated that therapy with histone peptides, which may act to promote tolerance in an animal to SLE-associated autoepitoes, and thereby inhibit production of the pathogenic autoantibodies responsible for SLE-associated nephritis, could be successful in delaying the onset and progression of SLE and complications thereof.

The present invention includes substantially any histone peptide corresponding to and overlapping a portion of the amino acid sequence of one or more of the histone proteins, including Hi, H2A, H2B, H3, and H4, that make up nucleosomes in an animal cell. A histone peptide of the present invention may comprise a portion of a histone protein which corresponds to an SLE-associated autoepitope that is known or becomes known, and is useful in the methods described herein.

A histone peptide of the invention can correspond to the amino acid sequence of a histone protein from substantially any animal. Preferably, the histone peptide used in the methods described herein has an amino acid sequence corresponding to a histone protein from the same species of the animal in whom tolerance is to be promoted. By way of example, a histone peptide described herein which is administered to a human will preferably have an amino acid sequence corresponding to a region of a human histone protein.

Preferably, a histone peptide of the invention is capable of promoting tolerance in an animal to an SLE-associated autoepitope, thereby inhibiting production by an animal of autoantibodies directed at antigens native to the animal (i.e., autoepitopes), such as those derived from single-stranded DNA (ssDNA), double-stranded DNA (dsDNA), nucleosomal particles, and histones of all of the animal's cells. The invention should be understood to include peptides corresponding to histone protein amino acid sequences which are known to be associated with, or which become associated with, an autoimmune disorder. Also preferable is a histone peptide having an amino acid sequence corresponding to any of SEQ. ID Nos. 1–26 and any of those listed in FIG. 17.

The present invention also provides modified histone peptides (i.e. analogs of histone peptides) which promote tolerance to SLE-associated autoepitopes in an animal or which are useful for identifying SLE associated T and B cells. Such modifications should not render the peptide more immunogenic, but rather, should render the peptide more tolerogenic. Analogs of histone peptides can differ from histone peptides described herein by conservative amino acid sequence differences or by modifications which do not affect sequence, or by both. For example, conservative amino acid changes may be made, which although they alter the primary sequence of the protein or peptide, do not normally alter its function. Conservative amino acid substitutions typically include substitutions within the following groups:

glycine, alanine;

valine, isoleucine, leucine;

aspartic acid, glutamic acid;

asparagine, glutamine;

serine, threonine;

lysine, arginine;

phenylalanine, tyrosine.

Modifications (which do not normally alter primary sequence) include in vivo, or in vitro chemical derivatization of peptides, e.g., acetylation, or carboxylation. Also included are sequences which have phosphorylated amino acid residues, e.g., phosphotyrosine, phosphoserine, or phosphothreonine. In addition, modifications which result in histone peptides that can be useful as probes to identify SLE-associated immune cells are included. Examples of this type of peptide modification include covalent attachment of a flourophore or chromophore, covalent attachment of a chemical moiety which can specifically bind other probe molecules or which can be derivatized to produce such binding, and covalent attachment of a chromogenic, enzyme cleavable moiety. An exemplary modification of a histone peptide is biotinylation which produces a biotinylated histone peptide that can be useful for identifying (i.e. tracking) SLE associated Th and B cells.

A particular type of modified histone peptide contemplated in the present invention is an altered peptide ligand or APL. APLs are peptides which are very similar in amino acid sequence to native (i.e. wild type) histone autoepitope peptides, but have different amino acid residues at positions in the autoepitopes that are known to contact the Th cell receptor (TCR). As the amino acid sequences of APLs would differ from the wild type histone peptide sequences only at those residues, it is considered well within the ability of the skilled artisan to design and synthesize APLs with single amino acid substitutions which bind an MHC class II molecule, such as the HLA-DR on a human B cell, but fail to stimulate the SLE-associated Th cells, thereby inhibiting autoantibody production. APLs which are useful in the methods of the present invention can therefore be readily prepared based on the sequences of the histone autoepitopes described herein.

Also included are peptides which have been modified using ordinary molecular biological techniques in order to improve their resistance to proteolytic degradation or to optimize solubility properties or to render them more suitable as a therapeutic agent. Analogs of such peptides include those containing residues other than naturally occurring L-amino acids, e.g., D-amino acids or non-naturally occurring synthetic amino acids. The peptides of the invention are not limited to products of any of the specific exemplary processes listed herein.

A histone peptide included in the present invention comprises from at least about three contiguous amino acids to at least about 50 amino acids, and from at least about twelve contiguous amino acids to at least about twenty five contiguous amino acids, wherein the peptide corresponds to portion of the amino acid sequence of a histone protein. Preferably, a histone peptide comprising from at least about fifteen contiguous amino acids to at least about twenty one contiguous amino acids.

The invention includes histone peptides, modified histone peptides, and histone peptide complexes that are encoded by an isolated nucleic acid, as well as those which are produced by synthetic means. A histone peptide, a modified histone peptide, or a histone peptide complex described herein can be made, purified, or both, using any of a variety of techniques known in the art. Representative techniques include using an automated peptide synthesizing apparatus, as well as recombinant techniques in which an isolated nucleic acid encoding a histone peptide or histone peptide complex is operably linked with transcriptional and translational regulatory sequences (e.g. using any of a variety of known and commercially available expression vectors) and expressed to yield the histone peptide. Alternatively, a naturally-occurring histone protein can be isolated and cleaved to yield a histone peptide. A histone peptide complex as described herein can be prepared by an ordinarily skilled artisan using the nucleotide sequences of the histone autoepitopes disclosed herein, for example, in FIG. 27, and either established recombinant DNA technology (Crawford et al. 1998, Immunity 8:675; Novak et al. 1999, J. Clin. Invest. 104:R63-R67; Kotzin et al. 1999, Proc. Natl. Acad. Sci. USA. 97:291), or other published technology (Lebowitz et al. 1999, Cell. Immunol. 192:175; McMichael and Kelleher 1999, J. Clin. Invest. 104:1669). Likewise, modified histone peptides such as those described herein, can be prepared by a method described herein and modified using any suitable modification methods or manufacturer's protocols.

The invention further includes an isolated nucleic acid encoding a histone peptide described herein. The isolated nucleic acid of the invention may be one which encodes a histone peptide corresponding to a portion of histone protein, and comprises from at least about three contiguous amino acids to at least about fifty amino acids, and preferably, from at least about twelve contiguous amino acids to at least about twenty five contiguous amino acids. More preferably, an isolated nucleic acid of the invention encodes a histone peptide comprising from at least about fifteen contiguous amino acids to at least about twenty one contiguous amino acids.

Alternatively, an isolated nucleic acid included in the invention can encode a histone peptide complex comprising an amino acid sequence corresponding to a portion of a histone protein and an amino acid sequence corresponding to a portion of one or more of a MHC II molecule and an immunoglobin (Ig) molecule. An isolated nucleic acid described herein can encode a histone peptide complex comprising a histone peptide fused to all or part of the amino acid sequence of one or more of a MHC II molecule and an immunoglobin (Ig) molecule. A histone protein complex encoded by an isolated nucleic acid of the invention can include a histone peptide which comprises from at least about three contiguous amino acids to at least about fifty amino acids, and preferably, from at least about twelve contiguous amino acids to at least about twenty five contiguous amino acids. More preferably, an isolated nucleic acid of the invention encodes a histone peptide complex which includes a histone peptide comprising from at least about fifteen contiguous amino acids to at least about twenty one contiguous amino acids. Even more preferably, the invention includes an isolated nucleic acid comprising any of the nucleotide sequences shown in FIG. 27 and any of SEQ ID Nos: 27–52.

In various embodiments, the invention includes an isolated nucleic acid which is a vector comprising an nucleic acid sequence which encodes a histone peptide of the invention. The vector can be used to introduce the nucleic acid encoding a histone peptide into a cell. Substantially, any type of vector known in the art is suitable for this purpose, including without limitation, plasmid based vectors, viral based vectors, and non-DNA vectors. Examples of suitable plasmid based vectors include, without limitation, any plasmid which comprises sequences capable of facilitating either of propagation and expression of the desired gene in a prokaryotic or eukaryotic cell. Examples of suitable viral vectors include, but are not limited to, retroviral vectors, adenoviral vectors, and adeno-associated viral vectors. Examples of non-DNA vectors include, without limitation, polylysine compounds, liposomes, and the like.

A vector comprising an nucleic acid sequence which encodes a histone peptide can comprise a promoter/regulatory sequence capable of driving histone peptide expression, a translational start codon, a histone peptide coding region, and a translational stop codon. Optionally, the vector can comprise expression-enhancing nucleotide sequences and nucleotide sequences which encode stabilizing amino acids or peptide sequences.

An isolated nucleic acid encoding a histone peptide described herein is assembled into, for example, an expression vector, using ordinary molecular biology techniques, such as those described in Sambrook et al. (1989, Molecular Cloning: A Laboratory Manual, Cold Spring Harbor Laboratory, New York), in Ausubel et al. (1997, Current Protocols in Molecular Biology, John Wiley & Sons, New York), and in Gerhardt et al. eds. (1994, Methods for General and Molecular Bacteriology, American Society for Microbiology, Washington, D.C.). Accordingly, the design of functional elements required to generate a vector capable of expressing a histone peptide, such as start and stop codons, stabilizing and expression-enhancing sequences, and any appropriate restriction endonuclease sites, is understood to be within the ability of one skilled in the art of molecular biology. Upon reading the disclosure provided herein, and using standard reference material, it is a simple matter for the skilled artisan to construct a vector comprising an isolated nucleic acid encoding a histone peptide, such that it can be useful in the methods of the present invention. By simply substituting a desired histone peptide-encoding nucleotide sequence in the appropriate location of substantially any commercially available expression vector, it is a simple matter to construct a vector comprising an isolated nucleic acid which encodes the desired histone peptide.

The SLE-associated autoepitopes, which have been localized (as illustrated herein in the Examples) to the amino acid sequences of nucleosomal histone proteins, H1, H2A, H2B, H3, and H4, are released for example, during kidney cell death. The onset of SLE is marked by, among other things, the development of inflammation in the kidney (i.e. nephritis) progressing to kidney disease and kidney failure. The inventors have discovered that administering to an animal histone peptides corresponding to these SLE-associated autoepitope regions of histone proteins can promote tolerance in the animal for these autoepitopes. While not wishing to be bound by a particular mechanism of action, the histone peptides described herein are believed to promote tolerance in an animal to SLE-associated autoepitopes which results in decreased SLE-associated autoantibody production by the animal, thereby delaying the onset and progression of SLE-associated nephritis. Thus, a composition comprising one or more of a histone peptide and a modified histone peptide can be administered to an animal in order to treat SLE-associated nephritis.

It has been discovered that portions of the histone proteins, H1, H2A, H2B, H3 and H4 are recognized as antigens (i.e. autoepitopes) by autoimmune Th cells that are essential for driving autoimmune B cells to produce a class of antibodies herein referred to as SLE-associated autoantibodies. These SLE-associated Th cells and autoantibodies occur in an animal having SLE, and are directed to autoepitopes associated with the onset or progression of SLE in the animal. The production of autoantibodies as is observed in SLE can be associated with other autoimmune disorders, and results in immune responses which can damage and destroy any cells or tissues of the animal by the formation of immune complexes. The histone peptides described herein correspond to autoepitope regions of the histone proteins which have been associated with the initiation and progression of SLE. Thus, a composition comprising one or more of a histone peptide and a modified histone peptide can be administered to an animal in order to promote tolerance in an animal to the autoepitope corresponding to the amino acid sequence of the histone peptide administered, and thereby, decrease the production of SLE-associated autoantibodies and inhibit an inflammation response associated with the production of SLE-associated autoantibodies. In addition, as these histone autoepitopes may be recognized by Th cells and autoantibodies associated with multiple other autoimmune disorders, compositions comprising one or more of a histone peptide and a modified histone peptide can be administered to an animal to treat an autoimmune disorder. Examples of other autoimmune disorders include, but are not limited to, rheumatoid arthritis and scleroderma.

It has further been discovered that an altered peptide ligand (APL) as described herein is useful for promoting tolerance to SLE-associated autoepitopes in mice. APLs are able function as antagonists or as partial agonist ligands for Th cells bearing receptors which are specific for wild type histone autoepitopes, analogous to other antigen systems (Evabold et al., 1993, Immunol. Today. 14:602; Sloan-Lancaster et al., 1994, J. Exp. Med. 180:1195; DeMagistris et al., 1992, Cell. 68:625; Madrenas et al., 1997, J. Exp. Med. 185:219; Korb et al., 1999, J. Immunol. 162:6401; DePalma et al.,1999, J. Immunol. 162:1982). Without wishing to be bound by a particular mechanism, it appears that T cells stimulated with partial agonist peptides (i.e. APLs) may enter a state of anergy in which they are unresponsive to subsequent stimulation with the wild type histone peptide. Because the binding of these modified peptides is controlled by fast dissociation kinetics, the APLs are unable to simultaneously engage a threshold number of Th cell receptors in a given population (Rabinowitz et al., 1996, Immunity 5:125). Therefore, APLs send a negative signal to (i.e. do not stimulate) autoimmune Th cells through inefficient binding of Th cell receptors, which in turn, results in decreased production of SLE-associated autoantibodies by autoimmune B cells. Thus, this type of modified histone peptide can be useful for promoting tolerance to SLE-associated autoepitopes, reducing the level of autoantibodies in an animal, inhibiting an immune response and associated inflammation, and treating SLE and other autoimmune disorders and complications thereof such as, SLE-associated nephritis.

The present invention includes modified histone peptides and histone peptide complexes which are useful for methods of identifying and tracking SLE-associated T cells and B cells. For example, the binding of a SLE-associated autoimmune T cell receptor (SLE-TCR) to its cognate antigenic histone peptide complexed with a MHC II molecule (i.e. a histone peptide/MHC II complex) on the surface of an autoimmune B cell, could be mimicked by a histone peptide complex, such as a fluorochrome-conjugated histone peptide/MHC II complex, which would be useful for binding, and thereby staining, SLE-associated T cells. By way of alternative example, a biotinylated histone peptide or histone peptide complex could be used to stain and track autoimmune B or T cells, respectively, in an animal with SLE at various stages of disease activity, including the active, recent remission, and long-term remission stages. This type of cell staining has previously been used to facillitate identification and tracking the antigen-specific T cells (McMichael and Kelleher. 1999, J. Clin. Invest. 104: 1669).

Due to the promiscuous nature of SLE-TCR/nucleosomal peptide interactions, a significant proportion of the SLE-associated T cells present in an animal, such as a human, may be detected using a histone peptide complex, such as a histone peptide/DR tetramer. Thus, a modified histone peptide or a histone peptide complex would be useful for early detection of SLE-associated T and B cells, and diagnosis of SLE before any clinical manifestations of the disease. Further, the onset and progression of SLE could be characterized with respect to disease manifestations, such as SLE-associated nephritis, using a modified histone peptide or a histone peptide complex. An improved clinical picture may result from instituting a more aggressive course of therapy at an earlier stage of the disease. Therefore, either a histone peptide complex or a modified histone peptide described herein can be useful for diagnosis or prognostication of SLE, and may also improve the therapeutic outcome of treating SLE and complications thereof by virtue of their diagnostic and prognostic value.

As noted elsewhere herein, an isolated nucleic acid encoding either a histone peptide or a histone peptide complex can be useful for tracking (i.e. identifying and monitoring) a pathogenic, SLE-associated T cell or B cell, and for producing useful quantities of one or more histone peptides or histone peptide complexes.

The histone peptides described in this disclosure, such as any of SEQ ID Nos: 1–26, and isolated nucleic acids which encode histone peptides and histone peptide complexes, such as an expression vector expressing a histone peptide or histone peptide complex, can be incorporated into pharmaceutical compositions for ethical administration to humans and other animals. Such pharmaceutical compositions are described elsewhere herein.

Methods

The present invention provides a method of promoting tolerance in an animal to SLE-associated autoepitopes, a method of reducing the production of autoantibodies in an animal, and a method of inhibiting inflammation associated with the production of autoantibodies. Each of these methods comprises administering to an animal, preferably a human, one or more of a histone peptide and an isolated nucleic acid encoding a histone peptide. This administration preferably results in one or more of the development of tolerance in the animal, the reduction of autoantibody production in the animal and the inhibition of inflammation associated with SLE-associated autoantibody production in the animal. More preferably, this administration results in the reduction of SLE-associated autoantibody production or inflammation derived therefrom.

As the production of SLE-associated autoantibodies to histone autoepitope regions may be involved in autoimmune disorders such as SLE, the present invention encompasses methods of treating an autoimmune disorder in an animal, such as a human, by administering a composition comprising a histone peptide or or a modified histone peptide in an amount sufficient to promote tolerance in the animal to autoepitopes associated with the autoimmune disorder, thereby inhibiting the production of autoantibodies associated with the disorder in the animal. In these methods, the preferred animal is a human, and the administration of such a composition promotes tolerance and results in reduced intermolecular help, less intense immune responses to autoantigens, and the inhibition of autoantibody production, thereby treating the autoimmune disorder in the animal. In an alternative embodiment, the modified histone peptide is an APL.

The present invention includes a method of tracking one or more of an SLE-associated T cell and an SLE-associated B cell. This method comprises administering to a population of immune cells, either in vivo or in vitro, a composition comprising one or more of a modified histone peptide, histone peptide complex, and an isolated nucleic acid encoding a histone peptide complex or modified histone peptide in an amount sufficient to detect binding of the histone peptide complex or modified histone peptide to an SLE-associated T cell or SLE-associated B cell present in the population. The binding of the peptide or peptide complex to the SLE-associated B or T cells is assessed by detecting an indicator portion (i.e. detectable label which emits or is associated with the emission of a detectable chemical signal) which is covalently linked (i.e. attached) to the peptide or peptide complex as described elsewhere herein. Preferably, this method results in the tracking SLE-associated cells and effectively tagging (i.e. staining) these cells so that the cells can be monitored (i.e. tracked) in a population of immune cells either within the body of an animal (i.e. in vivo), or obtained from the animal (i.e. in vitro). More preferably, this method employs a histone peptide complex comprising either a fluorochrome-conjugated histone peptide/MHC II molecule tetramer or a fluorochrome-conjugated histone peptide/MHC II-Ig chimeric dimer, or a modified histone peptide comprising a biotinylated histone peptide.

An isolated nucleic acid encoding a histone peptide complex, such as a vector comprising a histone peptide/MHC II gene, can be used to express a histone peptide complex in a cell, and therefore, can also be useful in tracking one or more of an SLE-associated T cell and an SLE-associated B cell. Accordingly, the above method of tracking one or more of an SLE-associated T cell and an SLE-associated B cell using an isolated nucleic acid which encodes a histone peptide complex or modified histone peptide complex additionally comprises administering the isolated nucleic acid to an animal or to the cells of an animal in a manner which permits the expression of a histone peptide complex or modified histone peptide in an amount sufficient to detect binding of the histone peptide complex or modified histone peptide to an SLE-associated T cell or SLE-associated B cell present in the population.

Specific Applications of Pharmaceutical Compositions

Peptides can be administered orally, intranasally, intravenously, intraperitoneally, or subcutaneously for tolerance therapy, and these classical methods have been described using other protein or peptide antigens over many decades (Wells. 1911, J. Infect. Dis. 8:147; Chase. 1946, Proc. Soc. Exp. Biol. Med. 61:257; Liblau et al. 1997, Immunol. Today. 18:599; Weiner. 1994, Proc. Natl. Acad. Sci. USA. 91:10762; Strober et al. 1998, J. Clin. Immunol. 18:1; Anderton et al. 1999, Immunological Rev. 169:123). Usually relatively high doses of the peptides have to be administered, although tolerance by administering low doses of peptides have also been described in other systems (Briner et al. 1993, Proc. Natl. Acad. Sci. USA. 90:7608). The exact mechanism of tolerization may vary (Liblau et al. 1997, Immunol. Today. 18:599; Zhong et al. 1997, J. Exp. Med. 186:673; Jenkins and Schwartz. 1987, J. Exp. Med. 165:302; Weiner. 1994, Proc. Natl. Acad. Sci. USA. 91:10762). Most commonly, the peptides are taken up by resting APC, and because the peptides are in simple soluble form without any inflammatory adjuvant carriers, the APC are not activated to express any co-stimulatory signaling molecules. Thus the peptides are presented on MHC class II molecules of the APC to their cognate T cells, without any co-stimulatory signals. The autoimmune T cells receive only signal 1, from the peptide-MHC binding to their antigen receptors (TCR), but not signal 2 (costimulation), thus rendering them inactive (anergic) or dead (deleted). As a consequence of this inactivation and/or deletion of the autoimmune T cells, autoimmune B cells are deprived of T-cell help, and thus autoantibody production is markedly diminished, as shown in SLE using our system (see Example 1, below).

Peptides are usually stored frozen in lyophilized powder form at −20° C., for the short-term or at −70° C. for longer storage. For oral tolerance therapy, peptides are given in high doses, for example in mice, 300 mg daily feeding for 8 days (Javed et al. 1995, J. Immunol. 155:1599; Benson et al. 1999, J. Immunol. 162:6247; Weiner. 1994, Proc. Natl. Acad. Sci USA. 91:10762). For oral tolerance, the peptide may be suspended in 0.15 M bicarbonate buffer together with soybean trypsin inhibitor (20mg/ml) also suspended in the same buffer for protection against proteolysis in the stomach (Javed et al. 1995, J. Immunol. 155:1599). However others found that peptide administered in simple PBS buffer is as effective (Baggi et al. 1999, J. Clin. Invest. 104:1287). Our histone peptides carry charged residues and they go into aqueous solution readily (see Example 1, below). In humans, oral tolerance, can be achieved with peptides as a lyophilized powder enclosed in opaque gelatin capsules which dissolve in the stomach. Oral administration of 300 mg of myelin basic protein daily for one year has been tried in patients with multiple sclerosis in such a manner (Weiner et al., 1993, Science. 259:1321).

For administrations through the other routes mentioned above (intranasal, intravenous, or subcutaneous), peptides are usually reconstituted in sterile, phosphate buffered saline solutions (PBS), just before administration. The dosage may vary from 100 to 300 microgram per day in mice for these alternate routes of tolerance induction.

Further Improvements in Tolerance Therapy with Overlapping B-cell and T-cell Autoepitopes Among the nucleosomal peptide epitopes for Th cells of SNF1 mice, $H4_{16-39}$ exhibited the most beneficial effect in tolerance therapy (see Example 1). Interestingly, the $H4_{16-39}$ peptide was not the most immunogenic among the nucleosomal autoepitopes in triggering pathogenic Th cells when administered with CFA into $SNF_1$ mice, nor did it have the highest affinity for MHC class II molecules (Kaliyaperumal et al. 1996, J. Exp. Med. 183:2459; Shi et al. 1998, J. Exp. Med. 187:367). But, $H4_{16-39}$, administered intravenously (I.V.) in saline, was able to tolerize both the autoimmune Th cells and the B cells of lupus, and thus was more efficient in "tolerance spreading" (Example 1). Autoimmune memory B cells were probably most affected by this peptide tolerogen, as they could not be rescued by stimulation with CD40L plus IL-4, or anti-Ig plus IL-4, or co-culture with autoimmune Th cells (Example 1). Apoptosis of mature B cells with high doses of peptide intravenously has been observed in the lysozyme system (Shokat and Goodnow 1995, Nature. 375:334), and it could have contributed to the tolerogenic effect of $H4_{16-39}$ peptide. Moreover, anergic B cells could be tolerogenic to autoimmune T cells, because they would present nucleosomal autoantigens without providing costimulation (Chan and Shlomchik 1998, J. Immunol. 160:51; Mohan et al. 1995, J. Immunol. 154:1470; Desai-Mehta et al. 1996, J. Clin. Invest. 97:2063; Eynon and Parker 1992, J. Exp. Med. 175:131; Mamula et al. 1994, J. Immunol. 152:1453; Buhlmann et al. 1995, Immunity 2:645).

Although B cell receptors (antibodies) are generally thought to recognize conformational determinants (shapes), a relevant peptide may form crucial parts of such determinants, as has been shown by antibody binding to peptides in many systems (Tung et al. 1997, Current Opin. Immunol. 9:839; Wucherpfennig et al. 1997, J. Clin. Invest. 100: 1114; Warren et al. 1995, Proc. Natl. Acad. Sci. USA. 92:11061). Nevertheless, the histone autoepitope, $H4_{16-39}$ falls within the region targeted by lupus autoantibodies. The overlapping of epitopes for pathogenic Th cells and autoimmune B cells of lupus makes $H4_{16-39}$ a highly efficient tolerogen. An additional epitope in nucleosomal core histone H3, $H3_{85-102}$, has been identified to which the splenic T cells of pre-nephritic $SNF_1$ mice spontaneously responded (Kaliyaperumal et al. 1996, J. Exp. Med. 183:2459). Interestingly, this T-cell epitope was also bound by spontaneously arising anti-DNA autoantibodies of lupus (Example 1). More recently, by analysing naturally processed peptides, the $H1_{22-42}$ peptide was identified as another dominant autoepitope for the autoimmune T, as well as B cells of lupus (see Example 3).

Thus, autoantigen-experienced and presumably memory T and B cells of lupus can be functionally inactivated in concert, at least for their ability to produce pathogenic autoantibodies by tolerogenic therapy with nucleosomal peptides. Importantly, some of the recurrent T-cell autoepitopes of human lupus that have been identified so far (Example 2), fall within the regions that might also be B-cell epitopes, i.e. targeted by lupus autoantibodies.

To establish this epitope sharing, the peptide epitopes recognized by T cells of lupus patients that have been identified (Example 2 and 3), can be tested for competitive inhibition of binding of autoantibodies in lupus patient's sera, to nucleosomes. Peptide competition ELISAs for autoantibodies have been described (Gavalchin et al. 1985, J. Immunol. 134:885; Tung et al. 1997, Current Opin. Immunol. 9:839; Wucherpfennig et al. 1997, J. Clin. Invest.

100:1114; Warren et al. 1995, Proc. Natl. Acad. Sci. USA. 92:11061). Anti-DNA autoantibodies from lupus sera can be affinity-purified on DNA-cellulose columns (Datta et al.1987, J. Exp. Med. 165:1252; Shivakumar et al. 1989, J. Immunol. 143:103), and then tested in similar competition immunoassay. It has been reported that such pathogenic anti-DNA autoantibodies of lupus mice (Gavalchin et al. 1985, J. Immunol. 134:885) bind nucleosomes as strongly as DNA (Mohan et al. 1993, J. Exp. Med. 177:1367).

Tracking Autoimmune B cells

The histone peptide autoepitopes that are recognized by autoimmune B cells, in addition to the Th cells may be biotinylated to study binding of histone peptides to receptors on autoimmune B cells from peripheral blood of lupus patients, along with staining for a B-cell marker (CD19 or CD20) for two color flow-cytometry, using established procedures (Desai-Mehta et al. 1996, J. Clin. Invest. 97:2063; Shivakumar et al. 1989, J. Immunol. 143:103). Competitive inhibition by anti-human Ig (Fab'2) may indicate that binding of the peptides is occuring through a BCR. If this assay for tracking autoimmune B cells is found to be specific using the nucleosomal histone peptides, then it may be evaluated in lupus patients with active disease and those in remission, as well as other unrelated autoimmune diseases. Thus, this assay for tracking autoimmune B cells may be useful as a valuable diagnostic and prognostic tool, complementary to tracking autoimmune Th cells with tetramers, as described below. Monoclonal antibodies made against histone peptide-MHC II tetramers that are described below could also be used to stain and track autoimmune B cells.

Therapy with Analogs of Histone Peptide Epitopes or Altered Peptide Ligands (APLs)

APLs with changes in residues that contact the TCR, can function as antagonists or as partial agonist ligands for T cells specific for the unaltered (i.e. wild type or wt) peptide epitope (Evabold et al. 1993, Immunol. Today. 14:602; Sloan-Lancaster et al. 1994, J. Exp. Med. 180:1195; DeMagistris et al. 1992, Cell. 68:625; Madrenas et al. 1997, J. Exp. Med. 185:219; Korb et al. 1999, J. Immunol. 162:6401; DePalma et al.1999, J. Immunol. 162:1982). T cells stimulated with partial agonist peptides may enter a state of anergy in which they are unresponsive to subsequent stimulation with the agonist (wild type or wt) peptide (references cited above). APLs send a negative signal to the T cell because of failure to simultaneously engage a threshold number of TCRs as a result of fast dissociation kinetics (Rabinowitz et al. 1996, Immunity 5:125). Although, it has been determined that tolerization with unaltered nucleosomal epitopes in lupus prone mice can delay and even halt progression of established lupus nephritis by tolerance spreading (see Example 1), work on other autoimmune disease models has shown that APLs might be more effective than wt ligands (Kuchroo et al. 1994, J. Immunol. 153:3326; Karin et al. 1994, J. Exp. Med. 180:2227; Yu et al. 1996, J. Exp. Med. 183:1771). Moreover, the effect of APLs on the autoimmune Th cells of lupus is unknown. Therefore, based on the sequences of the immunodominant, nucleosomal autoepitopes, it may be feasible to synthesize single amino acid substituted analogs (i.e. APLs or modified histone peptides) that can still bind to MHC class II molecules, such as HLA-DRs in humans, but fail to stimulate the pathogenic autoantibody-inducing Th cells associated with SLE.

Fine mapping of MHC and TCR contact residues may be done as follows. The anti-DNA autoantibody-inducing Th cells of lupus patients recognize nucleosomal peptide autoepitopes complexed with HLA-DR (MHC class II) molecules, and the major peptide epitopes have multiple DR-binding motifs (see Example 2, below). This type of promiscuous binding and recognition is important for the striking therapeutic effect of the nucleosomal peptides by across-the-board tolerance spreading in $SNF_1$ mice with lupus nephritis (see Example 1). Therefore, to initially map the MHC contact residues, analogs of the histone peptide autoepitopes can be synthesized with single amino acid (alanine or glycine) substitution at each of the putative anchor residues and each analog peptide can be tested for its ability to bind purified HLA-DR molecules in a competition immunoassay (Shi et al. 1998, J. Exp. Med.187:367). Those substituted peptides which still bind HLA-DR can then be tested for their ability to stimulate autoimmune Th cells of SLE for cytokine production and proliferation (as described in Example 2).

Following the mapping of MHC contact residues, the TCR contact residues in the substituted peptides that still bind HLA-DR can be mapped. These residues would presumably constitute the residues that point "up" in relation to the MHC contact residues (Kuchroo et al. 1994, J. Immunol. 153:3326; Evabold et al. 1993, Immunol. Today. 14:602; Sloan-Lancaster et al. 1994, J. Exp. Med. 180:1195; Karin et al. 1994, *J Exp. Med.* 180:2227). After an initial alanine scanning to localize the TCR contact residues in the nucleosomal peptides using assays described herein, further non-conservative substitutions can be performed, such as changes in charge, size or hydrophobicity. The altered peptides may not be able to stimulate the T cell clones or lines of human lupus. Such APLs modified with changes in TCR contact residues but not in MHC binding, could be tested for induction of anergy or deletion of autoimmune Th cells of lupus in vitro. More relevant is that the effect of APLs on the complex T cell response to the native autoantigen associated with lupus be examined. The ability of the APLs to antagonize the response of the T cells to whole nucleosomes, and unrelated wild type peptide epitopes from the nucleosomes can be tested using the above assays.

The promiscuity of lupus TCRs and the ability of a single nucleosomal epitope to cause "tolerance spreading" in murine models (see Example 1 and 2), suggest that similar features will be found in human lupus. The functional effect of the APLs is best tested using the more rigorous T helper assay, rather than using simple cytokine responses which may or may not be affected. Therefore, APLs could be assayed for inhibiting the autoantibody-inducing ability of Th clones or lines from lupus patients in co-culture systems, as described (Shivakumar et al. 1989, J. Immunol. 143:103; Rajagopalan et al. 1990, Proc. Natl. Acad. Sci. USA. 87:7020), in the presence or absence of respective wild type peptide (i.e. unaltered autoepitope or agonist). Thus, the altered peptide ligands could be tested for antagonism to autoimmune Th cells of SLE. Highly efficient APLs should inhibit responses to the wild type peptide epitopes at equimolar or lower concentrations, but should not cause MHC blockade by having an affinity for the DR molecules any higher than the wt peptides. Such APLs can be prepared based on the sequences of the histone autoepitopes in this invention.

Histone Peptide-MHC class II Tetramers for Tracking Autoimmune Th Cells

T cell receptor (TCR) of a particular antigen-specific T cell binds to its cognate antigenic peptide complexed with MHC molecule. Therefore, fluorochrome-conjugated, multivalent (i.e. tetrameric), soluble complexes of the peptide-MHC molecules can been used to stain and track the antigen-specific T cells (McMichael and Kelleher. 1999, J. Clin. Invest. 104: 1669). Recognition of nucleosomal epitopes by T cells from different lupus patients is HLA-DR dependent (see Example 2). The major peptide epitopes appear to have promiscuous DR binding motifs (Example 2), and two of them, $H4_{16-39}$ and $H4_{71-94}$ have actually been shown to bind HLA-DR (Shi et al.1998, J. Exp. Med. 187:367). For these reasons and given the promiscuous nature of lupus TCR-nucleosomal peptide recognition, a significant proportion of autoimmune T cells in lupus patients may be detected by appropriate nucleosomal peptide-DR tetramers, which can be prepared by using established recombinant DNA technology (Crawford et al. 1998, Immunity 8:675; Novak et al. 1999, J. Clin. Invest. 104:R63–R67; Kotzin et al. 1999, Proc. Natl. Acad. Sci. USA. 97:291), by expressing HLA-DR genes covalently linked to any one of the nucleotide sequences of the histone autoepitopes which are supplied in this invention. Alternatively, chimeric molecules of histone peptide-HLA-DR dimer-IgG can also be made using published technology (Lebowitz et al. 1999, Cell. Immunol. 192:175), and again using the nucleic acid encoding the histone peptide autoepitopes. Another approach is to make empty HLA-DR molecules in insect cells using appropriate vectors (McMichael and Kelleher 1999, J. Clin. Invest. 104:1669) and then incubate the MHC class II molecules with any of the histone peptide autoepitopes for stable binding. Similarly, such tetramers of mouse MHC class II or I-$A^d$-nucleosomal peptide, and also chimeric peptide-I-$A^d$-Ig dimers, can be made to track autoimmune T cells in lupus-prone mice. The reason for making both types of constructs is because sometimes tetramers do not work for particular TCR-peptide interactions of low avidiy or poor association kinetics. However, lupus TCR-nucleosomal peptide interactions might be of high affinity (Shi et al. 1998. J. Exp. Med. 187:367).

The biotinylated tetramers or dimers can be used to stain and track autoimmune T cells in lupus patients at various stages of disease activity, such as active stage, recent remission and long-term remission stages. Correlations with particular type of disease manifestation can be made, particularly in the case of lupus nephritis. Because the autoimmune Th cells appear long before the onset of clinical disease, their presence may be used to predict relapses or flare-up of lupus well in advance, and may identify patients who are at risk for developing SLE-associated nephritis. In such patients, more aggressive and early therapy can be instituted. Therefore, the histone peptide-MHC tetramers or dimers (i.e. histone peptide complexes) have important diagnostic and prognostic value.

Pharmaceutical Compositions in General

Factors and considerations for the application of compositions and pharmaceutical compositions comprising one or more of a histone peptide, a modified histone peptide, a histone peptide complex, and an isolated nucleic acid encoding one or more of a histone peptide, modified histone peptide, and a histone peptide complex are now described.

As a general rule for induction of tolerance, peptides have to be administered in a simple soluble form without any adjuvants or any carriers that might cause aggregation.

The invention encompasses the preparation and use of medicaments and pharmaceutical compositions comprising one or more of a histone peptide and a modified histone peptide described herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. Administration of one of these pharmaceutical compositions to a subject is useful, for example, for alleviating disorders associated with the production of autoantibodies in the subject, as described elsewhere in the present disclosure. The active ingredient may be present in the pharmaceutical composition in the form of a physiologically acceptable ester or salt, such as in combination with a physiologically acceptable cation or anion, as is well known in the art.

It is important to understand when generating any of the formulations and dosage units described in this section, that any of the peptides of the invention are stable in the form of a lyophilized powder stored at −70° C., or at −20° C. for shorter periods of time. The peptides must not be aggregated or conjugated or precipitated (i.e. the peptides or peptide complexes must be in soluble form in aqueous solution) to be optimally useful for the tolerance therapy described herein, particularly in Examples 1–3.

The formulations of the pharmaceutical compositions described herein may be prepared by any method known or hereafter developed in the art of pharmacology. In general, such preparatory methods include the step of dissolving the active ingredient in an aqueous solvent carrier or one or more other accessory ingredients, and then, if necessary or desirable, shaping or packaging the product into a desired single-or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

Pharmaceutical compositions that are useful in the methods of the invention may be prepared, packaged, or sold in formulations suitable for oral, parenteral, (subcontaneous, intravenous or intraperitoneal) intranasal, or another route of administration. Other contemplated formulations include immunologically-based formulations for optimum tolerance induction.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient. A unit dose of a pharmaceutical composition of the invention will generally comprise from about 1 nanogram to about 1 gram of the active ingredient, and preferably comprises from about 50 nanograms to about 10 milligrams of the active ingredient.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous solution.

Soft gelatin capsules comprising the active ingredient may be made using a physiologically degradable composition, such as gelatin. Such soft capsules comprise the active ingredient, which may be mixed with water.

Pulsed release technology such as that described in U.S. Pat. No. 4,777,049 may also be used to administer the active agent to a specific location within the gastrointestinal tract. Such systems permit drug delivery at a predetermined time and can be used to deliver the active agent, optionally together with other additives that my alter the local microenvironment to promote agent stability and uptake, without relying on external conditions other than the presence of water to provide in vivo release.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid solutions may further comprise one or more additional ingredients including, but not limited to, suspending agents, dispersing or wetting agents, preservatives, buffers, salts, flavorings, coloring agents, and sweetening agents.

Liquid solutions of the active ingredient in aqueous solvents may be prepared so that the active ingredient is dissolved, rather than suspended in the solvent. Aqueous solvents include, for example, water and isotonic saline.

Powdered and granular formulations of a pharmaceutical preparation of the invention may be prepared using known methods. Such formulations may be administered directly to a subject, used, for example, to form tablets, to fill capsules, or to prepare an aqueous solution by addition of an aqueous vehicle thereto. Each of these formulations may further comprise one or more of dispersing or wetting agent, a suspending agent, and a preservative. Additional excipients, such as fillers and sweetening, flavoring, or coloring agents, may also be included in these formulations.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intravenous injection and intravenous, intraarterial, or kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules, in multi-dose containers containing a preservative, or in single-use devices for auto-injection or injection by a medical practitioner. Formulations for parenteral administration include, but are not limited to, solutions, or aqueous vehicles, pastes, and implantable sustained-release formulations. Such formulations may further comprise one or more additional ingredients including, but not limited to, stabilizing, or dispersing agents. In one embodiment of a formulation for parenteral administration, the active ingredient is provided in dry (i.e. lyophilized powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous solution. This solution may be formulated according to the known art, and may comprise, in addition to the active ingredient, additional ingredients such as the dispersing agents, or wetting agents, described herein. Such sterile injectable formulations may be prepared using a non-toxic parenterally-acceptable diluent or solvent, such as water or buffered saline, for example. Other acceptable diluents and solvents include, but are not limited to, Ringer's solution, or isotonic sodium chloride solution.

A pharmaceutical composition of the invention may be prepared, packaged, or sold in a formulation suitable for intranasal administration. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for intranasal delivery may also provide the active ingredient in the form of droplets of a solution or suspension. Such formulations may be prepared, packaged, or sold as aqueous solutions optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be administered to deliver a dose of the active ingredient which is from about 500 picograms per kilogram body weight per day to about 1 milligram per kilogram body weight per kilogram of an animal. Preferably the dose is from about 100 micrograms per kilogram of animal to about 600 micrograms per kilogram body weight.

As a general rule for induction of tolerance, peptides have to be administered in a simple soluble form without any adjuvants or any carriers that might cause aggregation. Peptides can be administered orally, intranasally, intravenously, intraperitoneally, or subcutaneously for tolerance therapy, and these classical methods have been described using other protein or peptide antigens over many decades (Wells. 1911, J. Infect. Dis. 8:147; Chase. 1946, Proc. Soc. Exp. Biol. Med. 61:257; Liblau et al. 1997, Immunol. Today. 18:599; Weiner. 1994, Proc. Natl. Acad. Sci. USA. 91:10762; Strober et al. 1998, J. Clin. Immunol. 18:1; Anderton et al. 1999, Immunological Rev. 169:123). Usually relatively high doses of the peptides have to be administered, although tolerance by administering low doses of peptides have also been described in other systems (Briner et al. 1993, Proc. Natl. Acad. Sci. USA. 90:7608). The exact mechanism of tolerization may vary (Liblau et al. 1997, Immunol. Today. 18:599; Zhong et al. 1997, J. Exp. Med. 186:673; Jenkins and Schwartz. 1987, J. Exp. Med. 165:302; Weiner. 1994, Proc. Natl. Acad. Sci. USA. 91:10762). Most commonly, the peptides are taken up by resting APC, and because the peptides are in simple soluble form without any inflammatory adjuvant carriers, the APC are not activated to express any co-stimulatory signaling molecules. Thus the peptides are presented on MHC class II molecules of the APC to their cognate T cells, without any co-stimulatory signals. The autoimmune T cells receive only signal 1, from the peptide-MHC binding to their antigen receptors (TCR), but not signal 2 (costimulation), thus rendering them inactive (anergic) or dead (deleted). As a consequence of this inactivation and/or deletion of the autoimmune T cells, autoimmune B cells are deprived of T-cell help, and thus autoantibody production is markedly diminished, as shown in SLE using our system (see Example 1, below).

Peptides are usually stored frozen in lyophilized powder form at −20° C., for the short-term or at −70° C. for longer storage. For oral tolerance therapy, peptides are given in high doses, for example in mice, 300 mg daily feeding for 8 days (Javed et al. 1995, J. Immunol. 155:1599; Benson et al. 1999, J. Immunol. 162:6247; Weiner. 1994, Proc. Natl. Acad. Sci USA. 91:10762). For oral tolerance, the peptide may be suspended in 0.15 M bicarbonate buffer together with soybin trypsin inhibitor (20 mg/ml) also suspended in the same buffer for protection against proteolysis in the stomach (Javed et al. 1995, J. Immunol. 155:1599). However others found that peptide administered in simple PBS buffer is as effective (Baggi et al. 1999, J. Clin. Invest. 104:1287). Our histone peptides carry charged residues and they go into aqueous solution readily (see Example 1, below). In humans, oral tolerance, can be achieved with peptides as a lyophilized powder enclosed in opaque gelatin capsules which dissolve in the stomach. Oral administration of 300 mg of myelin basic protein daily for one year has been tried in patients with multiple sclerosis in such a manner (Weiner et al., 1993, Science. 259:1321).

For administrations through the other routes mentioned above (intranasal, intravenous, or subcutaneous), peptides are usually reconstituted in sterile, phosphate buffered saline solutions (PBS), just before administration. The dosage may vary from 100 to 300 microgram per day in mice for these alternate routes of tolerance induction.

It is understood that the ordinarily skilled physician will readily determine and prescribe an effective amount of the active ingredient to alleviate an autoimmune disorder associated with autoantibody production in an animal. In so proceeding, the physician may, for example, prescribe a relatively low dose at first, subsequently increasing the dose until an appropriate response is obtained. It is further understood, however, that the specific dose level for any particular subject will depend upon a variety of factors including the activity of the specific compound employed, the age, body weight, general health, gender, and diet of the subject, the time of administration, the route of administration, the rate of excretion, any drug combination, and the severity of the disorder being treated.

Kits

Another aspect of the invention relates to a kit comprising a pharmaceutical composition of the invention and an instructional material. As used herein, an "instructional material" includes a publication, a recording, a diagram, or any other medium of expression which is used to communicate the usefulness of the pharmaceutical composition of the invention for inhibiting the production of autoantibodies in a subject. The instructional material may also, for example, describe an appropriate dose of the pharmaceutical composition of the invention. The instructional material of the kit of the invention may, for example, be affixed to a container which contains a pharmaceutical composition of the invention or be shipped together with a container which contains the pharmaceutical composition. Alternatively, the instructional material may be shipped separately from the container with the intention that the instructional material and the pharmaceutical composition be used cooperatively by the recipient.

The invention also includes a kit comprising a pharmaceutical composition of the invention and a delivery device for delivering the composition to a subject. By way of example, the delivery device may be a squeezable spray bottle, a metered-dose spray bottle, an aerosol spray device, an atomizer, a dry powder delivery device, a self-propelling solvent or powder-dispensing device, a syringe, a needle, or a dosage measuring container. The kit may further comprise an instructional material as described herein.

A kit provided by the invention can be useful for, among other things, tracking SLE-associated T and B cells, promoting tolerance to SLE-associated autoepitopes, inhibiting the production of autoantibodies, inhibiting an immune response and associated inflammation, treating SLE or other autoimmune disorders and complications thereof, and in the diagnosis and prognostication of SLE in an animal. Useful applications for a kit included in the present invention are described below.

The invention is now described with reference to the following examples. These examples are provided for the purpose of illustration only and the invention should in no way be construed as being limited to these examples but rather should be construed to encompass any and all variations which become evident as a result of the teaching provided herein.

EXAMPLE 1

Antigen-Specific Therapy of Murine Lupus Nephritis Using Nucleosomal Peptides

The experiments of this Example demonstrate that the pathogenic T and B cells of systemic lupus erythematosus are susceptible to autoantigen-specific tolerogens, and that administration of nucleosomal peptides can impair autoimmune T cell responses and inhibit production of pathogenic autoantibodies.

The materials and methods used in this Example are now described.

Mice

NZB and SWR mice were purchased from The Jackson Laboratory (Bar Harbor, Me.). (SWR×NZB)$F_1$ $SNF_1$ hybrid mice were bred and female progeny mice were used, in accordance with standard procedures. The lupus-prone $SNF_1$ mice spontaneously develop SLE and die from SLE-associated nephritis with age (Datta and Schwartz, 1976, Nature 263:412; Datta et al. 1978, J. Exp. Med. 147:854).

Antibodies

The following monoclonal antibodies (mAbs) were used: anti-I-$A^d$ (HB3), anti-I-$A^{b,d,q}$ (TIB120), anti-HSA (TIB183), anti-Thy1.2 (TIB99), anti-CD8 (TIB211), and anti-CD3 (145-2C11). All antibodies were obtained from American Type Culture Collection (ATCC, Rockville, Md.).

Synthesis of Peptides

All peptides were synthesized using FMOC-compatible protecting group, reagents and procedures by Chiron Mimotopes, (San Diego, Calif.). Purity of the peptides was verified by the manufacturer using amino acid analysis. The nucleosomal histone peptides used in these experiments were $H4_{16-39}$, $H4_{71-94}$, and $H2B_{10-33}$, which correspond to the histone 4 protein (H4), amino acids 16–34 and 71–94, and histone 2B protein, (H2B) amino acids 10–33, respectively. The peptides were purified by high performance liquid chromatography (HPLC) using a gradient of water and acetonitrile, and analyzed by mass spectrometry to verify purity.

Tolerance Induction with Histone Derived Peptides

Long-term experiments used 12 week-old, autoimmune, but pre-nephritic $SNF_1$ female mice. Nine mice per peptide test group were injected intravenously with either a saline (solution) or a peptide solution comprising saline and 300 micrograms of one of $H2B_{10-33}$, $H4_{16-39}$, and $H4_{71-94}$. Each mouse received three subsequent injections of either the saline solution or one of the peptide solutions at two-week intervals. The mice were monitored weekly for proteinuria using an Albustix kit (VWR Scientific, Chicago, Ill.), and sacrificed upon the development of persistent proteinuria. Persistent protenuria was identified as an amount of protein in urine that is equivalent to or greater than 300 milligrams per deciliter, and is a primary indication of severe kidney disease and damage associated with nephritis. Sera were collected from each mouse and the IgG anti-nuclear autoantibodies determined. Blood urea nitrogen (BUN) was measured by Azostix (Miles, Ekhart, Ind.). Immune complex deposition and glomerulonephritis in the kidney were detected by staining with Hematoxylin and Eosin and anti-mouse Ig. These procedures were carried out as previously described (Mohan et al., 1993, J. Exp. Med. 177:1367; Mohan et al., 1995, J. Immunol. 154:1470; Eastcott et al., 1983, J. Immunol. 131:2232; Adams et al., 1991, Proc. Natl. Acad. Sci. USA 88:11271; Kalled et al., 1998, J. Immunol. 160:2158; Gaynor et al., 1997, Proc. Natl. Acad. Sci. USA 94:1955).

Short-term experiments were conducted to test the early immunological consequences of tolerance therapy. Twelve week old $SNF_1$ mice were injected once a week for four weeks with either a saline solution or a peptide solution comprising saline and 300 micrograms of one of the above described peptides. Mice were sacrificed at two weeks after the last injection. Presence of autoimmune T and B cells was analyzed and renal lesions were graded.

For experiments investigating chronic therapy of established glomerulonephritis, 18 month old $SNF_1$ mice exhibiting persistent proteinuria were used. Six mice per group were injected intraperitoneally once each month with either a saline solution or a peptide solution comprising saline and 300 micrograms of one of the identified peptides. The endpoint of these experiments was the development of moribund state due to renal failure.

Autoantibody Quantitation

Levels of IgG class autoantibodies specific for single-stranded DNA (ssDNA), double-stranded DNA (dsDNA), histones, and nucleosomes (i.e. histone-DNA complexes), in culture supernatants or serum, were estimated using an enzyme-linked immunosorbent assay (ELISA). Anti-DNA mAbs 564 and 205 were used to generate standard curves as previously described (Mohan et al., 1993, J. Exp. Med. 177:1367; Kaliyaperumal et al., 1996, J. Exp. Med. 183:2459; Mohan et al., 1995, J. Immunol. 154:1470; Adams et al., 1991, Proc. Natl. Acad. Sci. USA 88:11271). Sera were diluted 1:400 and heat-inactivated before use according to standard procedures. Sera from normal SWR mice were used as the negative control. Total polyclonal IgG levels were also measured by ELISA as previously described (Mohan et al., 1993, J. Exp. Med. 177:1367; Mohan et al., 1995, J. Immunol. 154:1470; Adams et al., 1991, Proc. Natl. Acad. Sci. USA 88:11271).

Isolation of $CD4^+$ Cells and B Cells

Splenic $CD4^+$ T cells were isolated as described previously (Mohan et al., 1993, J. Exp. Med. 177:1367; Mohan et al., 1995, J. Immunol. 154:1470). Briefly, splenic T cells were purified from 3–4 month old $SNF_1$ mice by applying spleen cell preparations to a nylon wool column, lysing $CD8^+$ T cells, and contaminating B cells using antibody preparations, anti-CD8 (TIB211), ant-I-$A^{b\ d,q}$ (TIB120), anti-HSA (TIB183), and a 1:10 dilution of rabbit and guinea pig complement mixture (Pel Freeze Biologicals, Rogers, Ark.). B cells were prepared from $SNF_1$ mice by treating splenocytes that were applied to nylon wool columns twice with anti-T cell antibody, anti-Thy1.2 (TIB99) and complement.

Cytokine Assays

Fresh splenic $CD4^+$ T cells, obtained from each of the tolerized (i.e. peptide-injected) or control mice were seeded in flat-bottom 96-well plates (Costar) at a concentration of $1\times10^5$ cells per well. Cells were seeded in triplicate wells. Previously irradiated (3000 rads) APCs treated with anti-Thy-1.2 and complement were also seeded in each well at $5\times10^5$ cells per well. Preparation of APCs was described previously (Mohan et al., 1993, J. Exp. Med. 177:1367; Kaliyaperumal et al., 1996, J. Exp. Med. 183:2459). A 200 microliter volume of HL-1 serum free medium (Biowhittaker, Walkersville, Md.) containing varying concentrations of each test peptide was also added separately to the wells in triplicate. The cultures were incubated for 24–36 hours. Control cultures contained cells and medium without any peptide. The culture supernatants were removed from the wells, and cytokine assays were performed as previously described (Kaliyaperumal et al., 1996, J. Exp. Med. 183:2459). Anti-IL-2, anti-IFNγ, and anti-IL-4, capture and biotinylated antibody pairs, and their respective standard cytokines (rIL-2, rIL-4, rIFNγ) were purchased from Pharmingen (San Diego, Calif.). Streptavidin-conjugated horseradish peroxidase (Streptavidin-HRP) and the substrate, TMB, were purchased from Sigma Chemical Co. (St. Louis, Mo.). Cytokines were quantitated according to manufacturer instructions.

Helper Assays for IgG Autoantibody Production

T-cells from peptide-treated mice used in the short-term experiments were co-cultured with splenic B cells from unmanipulated mice. Conversely, T cells from unmanipulated $SNF_1$ mice (i.e. control mice) were co-cultured with splenic B cells from tolerized (i.e. peptide-injected) mice. Each of the cell types was seeded in 24-well plates at an initial concentration of $2.5 \times 10^6$ cells per well. Cultures were maintained for 7 days, as previously described (Datta et al., 1987, J. Exp. Med. 165:1252; Sainis and Datta, 1988, J. Immunol. 140:2215). B cells from unmanipulated or tolerized animals were cultured alone to measure baseline autoantibody production. Culture supernatants were collected, freeze-thawed, and assayed by ELISA for antibodies against ssDNA, dsDNA, histones and nucleosomes. For studies involving stimulation of B cells by soluble CD40 ligand, CD40L-CD8 fusion protein (Wortis et al., 1995, Proc. Natl. Acad. Sci. USA 92:3348) was added to either the co-culture wells or the wells with B cells alone and maintained in the medium for the entire 7-day culture period.

Assay for Regulatory T Cells

To determine whether tolerance therapy induced any regulatory T cell activity, T cells from either unmanipulated $SNF_1$ mice or tolerized (i.e. peptide injected) mice, were co-cultured with a mixture of splenic B cells and T cells from unmanipulated $SNF_1$ mice in 24-well plates for 7 days. Culture supernatants were then collected, freeze-thawed, and assayed for the presence of IgG antibodies against ssDNA, dsDNA, histones, and nucleosomes using an ELISA.

The results of the experiments presented in this Example are now described.

Brief Therapy with Nucleosomal Histone Peptides

Figure 2:
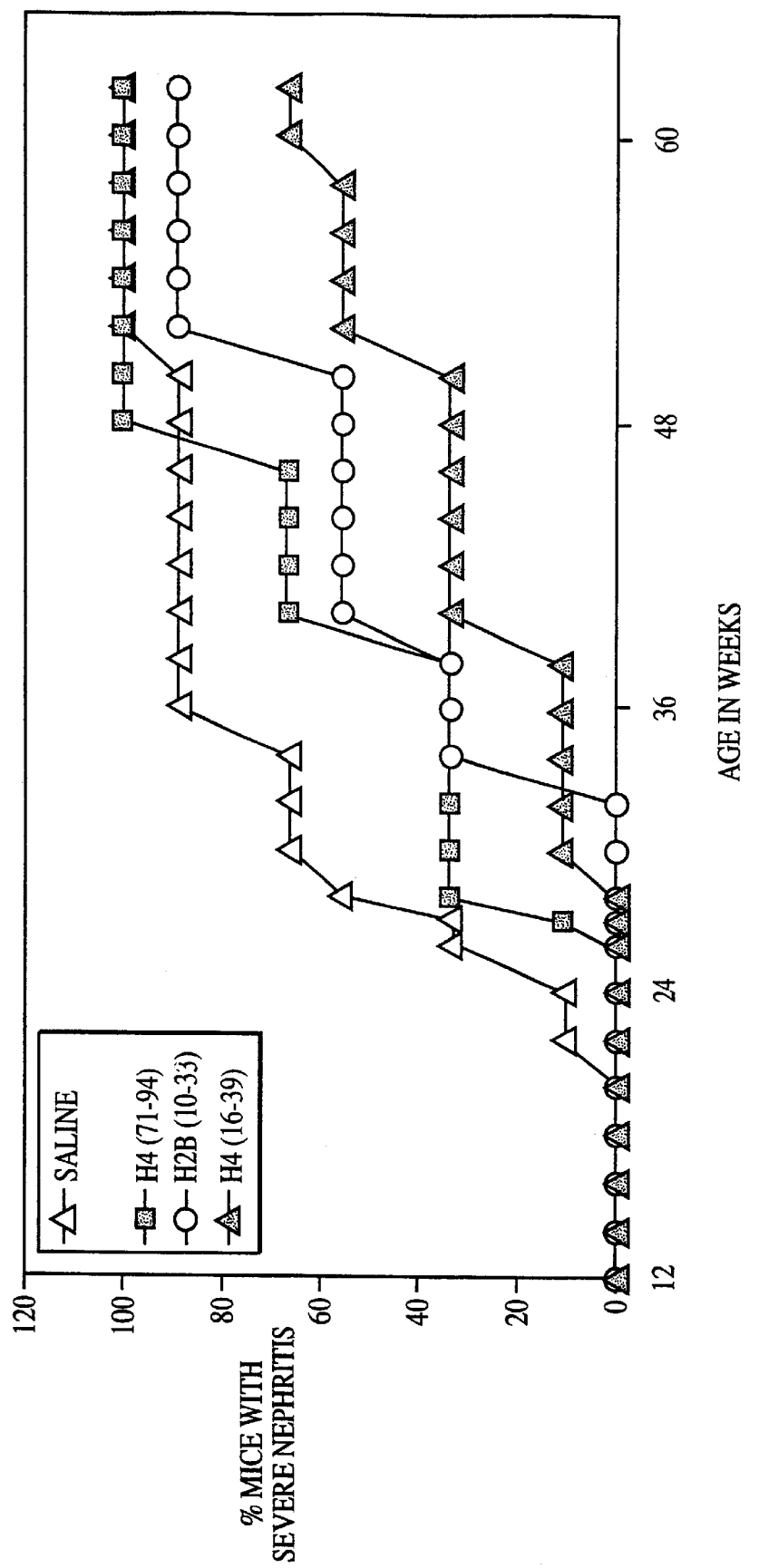
FIG. 2 is a graph illustrating the effect on SLE-associated nephritis of brief therapy with nucleosomal histone peptides. The figure illustrates the incidence of severe (4+grade) nephritis in $SNF_1$ mice that received four injections of either a histone peptide (i.e. $H4_{71-94}$, $H2B_{10-33}$, $H4_{16-39}$) or saline starting at 12 weeks age.

Twelve week old pre-nephritic $SNF_1$ female mice that did not have proteinuria, or any other evidence of kidney disease, were each injected intravenously with a peptide solution comprising Saline and one of the peptides, $H2B_{10-33}$, $H4_{16-39}$, or $H4_{71-94}$. The control group of mice were injected with a saline solution that did not contain peptide. Each group of animals received three additional injections at two week intervals. The mice were monitored weekly for proteinuria and sacrificed when they developed severe nephritis. As shown in FIG. 2, the control mice began developing severe nephritis at 22 weeks. At 28 weeks of age, 55.5% of the saline control group, and 33.3% (p=0.637, Fishers exact test) of the $H4_{71-94}$ peptide injected group of mice developed severe nephritis. In contrast, the $H2B_{10-33}$ and $H4_{16-39}$ injected mice did not develop disease at this age (p=0.029).

The largest difference in incidence of severe nephritis between the peptide injected groups and the control group was seen at 36–38 weeks of age. At this age, 88.8% of the control group mice had developed severe nephritis, whereas the $H2B_{10-33}$, and $H4_{71-94}$ groups of mice each had an incidence of only 33.3% (p=0.05) and the H4 16–39 group mice exhibited an incidence of only 11.1% (p=0.003). Mice in all groups, except the $H4_{16-39}$ group mice, developed severe nephritis by 54 weeks of age. The $H4_{16-39}$ group mice had a 55.5% incidence of severe nephritis at 54 weeks of age, but in relationship to the control group (p=0.08), this difference was not significant.

T Cell Response to Peptides in Treated Animals

In unmanipulated $SNF_1$ mice, T cells are spontaneously primed to nucleosomal peptides early in life, and have been shown to respond to them in vitro (Kaliyaperumal et al., 1996, J. Exp. Med. 183:2459). Therefore, T cells isolated at the time of sacrifice from peptide-injected or control mice in the long-term experiments, were co-cultured with APC in the presence of the peptides or whole nucleosomal particles. The response of these T cells was assessed by incorporation of $^3H$-thymidine as an indication of proliferation, and by ELISA to determine the extent of cytokine (IL-2, IFN-γ and IL-4) production. These mice had already developed a 4+ grade of severe nephritis at the time of testing, therefore the background levels of proliferation were high. There was no deviation in cytokine production when the saline treated group was compared with the peptide-treated groups.

The assessment of the incidence of nephritis and the grading of renal pathology in short term experiment mice are shown in Table 1. For these experiments, the mice were sacrificed two weeks after the last injection of either peptide solution or saline solution. The mice were 22–23 weeks old when the data were obtained. In these mice, no consistent differences were detected in cytokine production levels or cytokine profiles in T cells from the control group relative to the peptide-injected groups of mice in response to any of the peptides or to whole nucleosomes.

TABLE 1

Incidence of lupus nephritis at sacrifice in "short-term" batch of mice

| Group | Grading of Lupus Nephritis | | | | |
|---|---|---|---|---|---|
| | 0 | 1+ | 2+ | 3+ | 4+ |
| | Percent Incidence | | | | |
| Saline | | 33.3 | | 33.3 | 33.3 |
| $H2B_{10-33}$ | | 66.6 | 33.3 | | |
| $H4_{16-39}$ | 33.3 | 66.6 | | | |
| $H4_{71-94}$ | | | | 66.6 | 33.3 |

Effect of Peptide Therapy on $CD4^+$ Cell Help for Autoantibody Production

Figure 3:
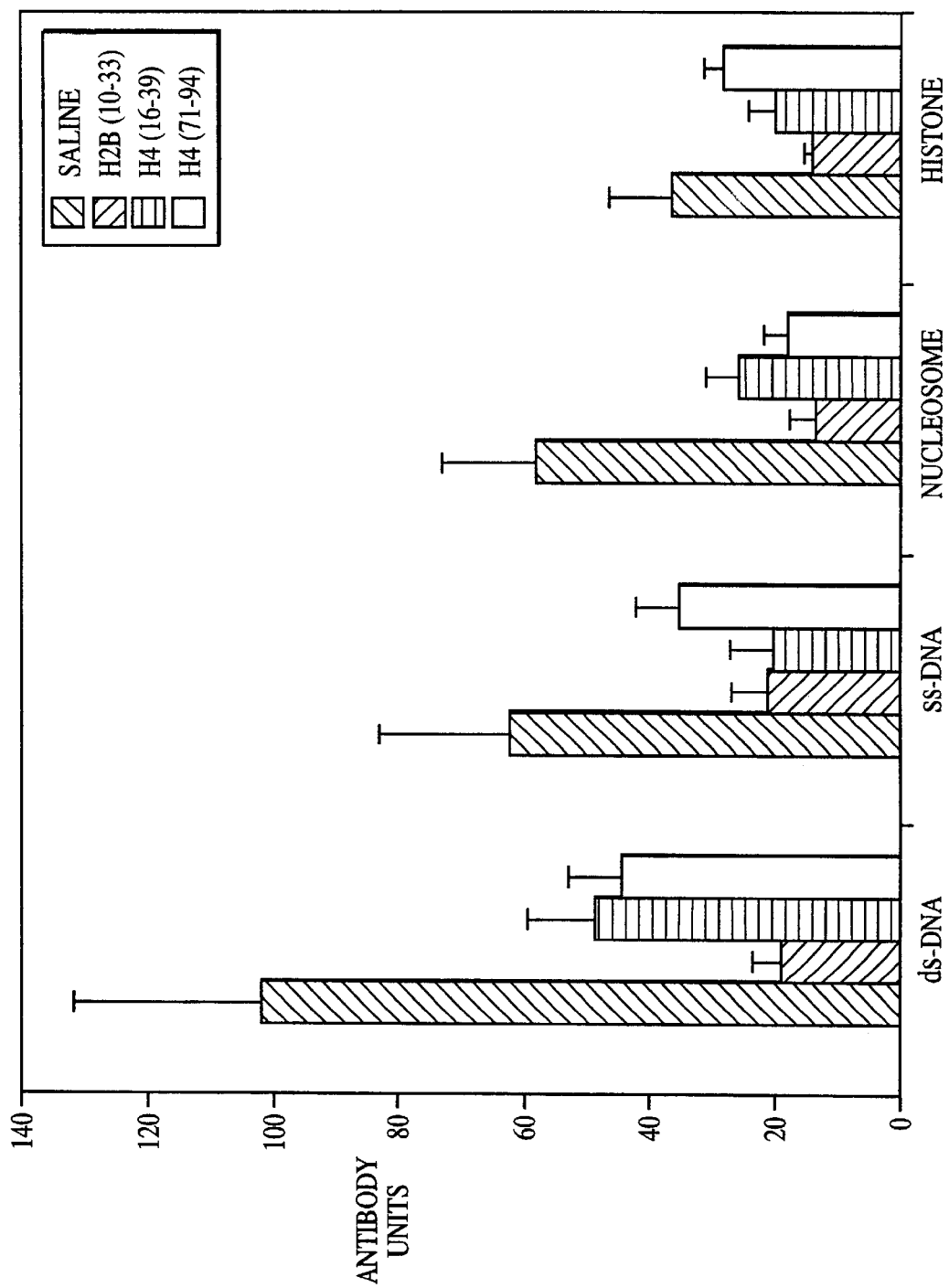
FIG. 3 is a bar graph depicting the ability of $CD4^+$ T cells obtained from treated mice to facilitate autoantibody production. Units of IgG autoantibodies produced in the culture supernatants are expressed as a mean number of antibody units per deciliter±the standard error of the mean (SEM) from five experiments. Baseline levels of IgG autoantibodies produced by B cells cultured alone were: anti-dsDNA, 4.1±0.8; anti-ssDNA, 2.2±0.1; anti-nucleosome, 4.4±1.1; and anti-histone, 3.7±0.6.
Figure 4C:
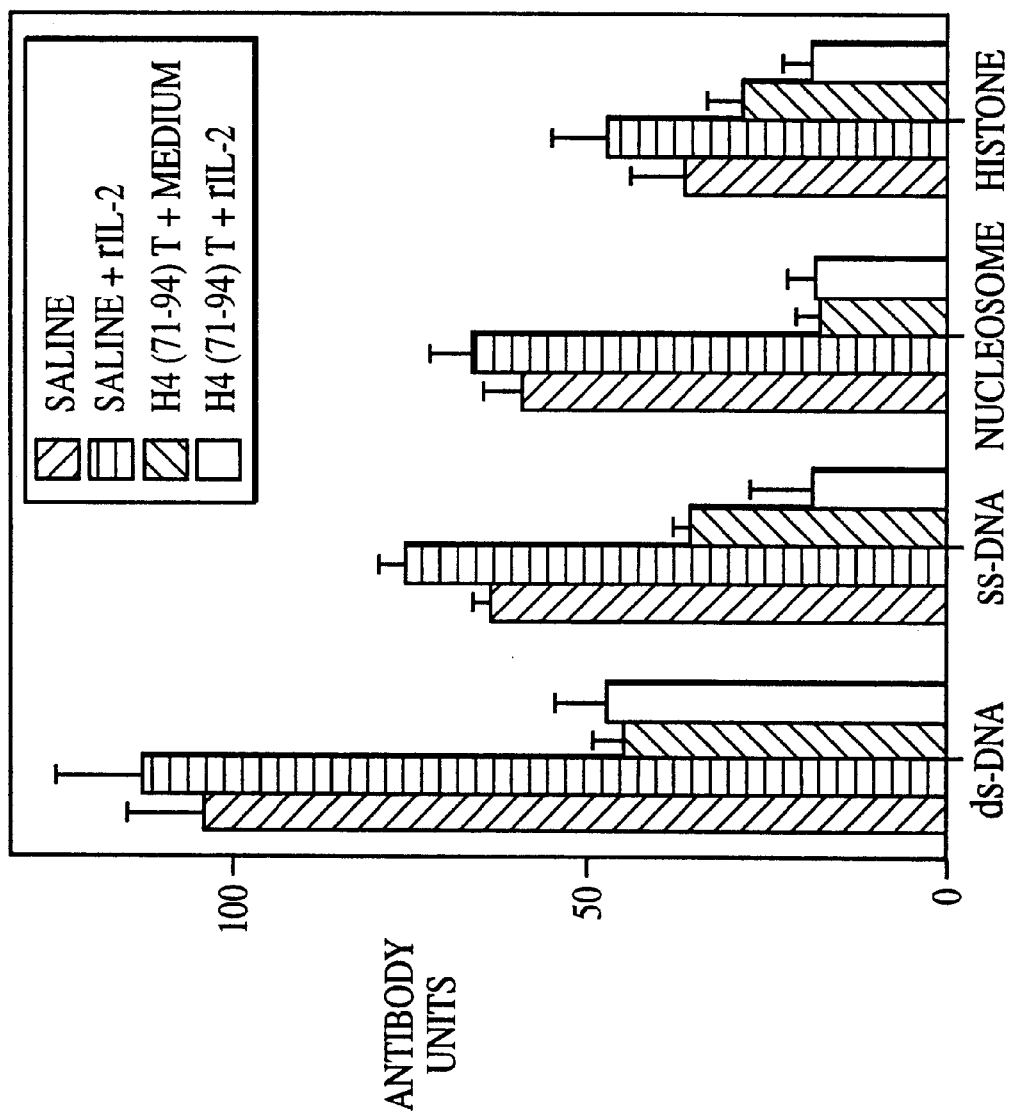

The helper assay, used to detect autoantibody-inducing ability in T cells, is a much more rigorous test for autoimmune T helper cell (Th) function. Therefore, in further experiments the helper assay as described above was used to determine the function of T and B cells in tolerized (i.e. peptide-injected) mice from the short-term experiments. The helper assay tests the ability of T cells to functionally help B cells to produce pathogenic autoantibodies to nuclear antigens. In this assay, $CD4^+$ T cells were isolated from the peptide-injected mice and co-cultured with B cells isolated from unmanipulated 16–20 week. old SNF mice. The co-culture supernatants were analyzed for the presence of IgG antibodies against ssDNA, dsDNA, nucleosomes, and histones using an ELISA. The results shown in FIG. 3 are the mean values±the standard error of the mean (SEM) of five experiments. Anti-dsDNA antibody production was reduced by approximately 50% in the cultures containing T cells from $H4_{71-94}$, and $H4_{16-39}$ treated group of mice as compared with the control group (p=0.03). The $H2B_{10-33}$ group mice exhibited a five fold decrease in anti-dsDNA antibody production relative to the control group mice. Induction of anti-ssDNA antibody production was also reduced by approximately 55% in the $H2B_{10-33}$ and $H4_{16-39}$ group mice, relative to the control group mice (p=0.005 to 0.001). However, reductions of anti-ssDNA antibody production in the $H4_{71-94}$ group mice were not significant. Anti-nucleosomal antibody production exhibited a similar pattern. The co-cultures of T and B cells from $H2B_{10-33}$, $H4_{16-39}$, and $H4_{71-94}$, injected group mice produced 2.5 to 4 times less anti-nucleosome antibody than the control group mice (p=0.03 to 0.05). The effect on anti-histone antibody induction in all groups was not significantly different (p=0.1) relative to the control group.

Addition of rIL-2 to $CD4^+$ Cells for Testing Anergy

Figures 1, 18A:
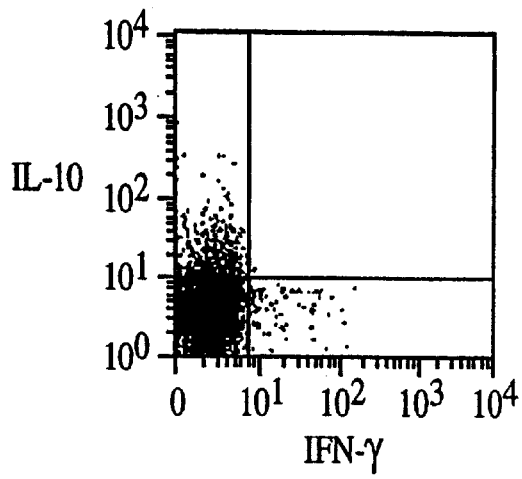
FIGS. 18A and 18B, depict representative examples of two-color intracellular cytokine staining of CD4$^+$ T cells freshly obtained from two SLE patients, designated R-WG and R-SC, who were in remission.
Figures 2, 18A:
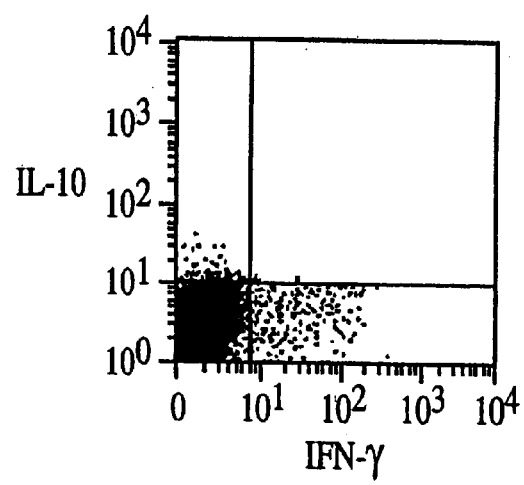
Figures 3, 18A:
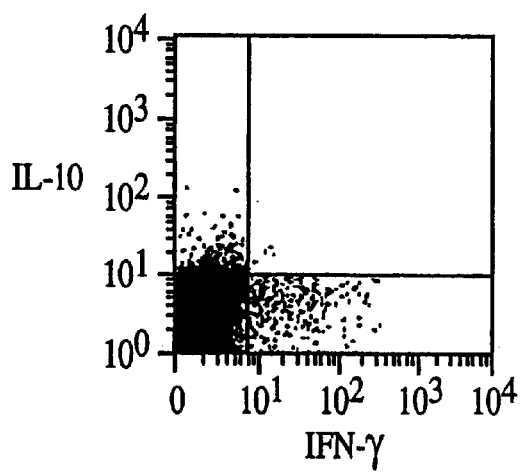
Figures 4, 18A:
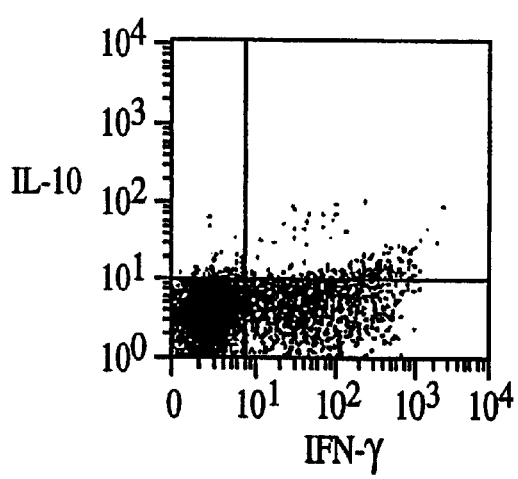
FIG. 4, comprising
Figures 1, 18B:
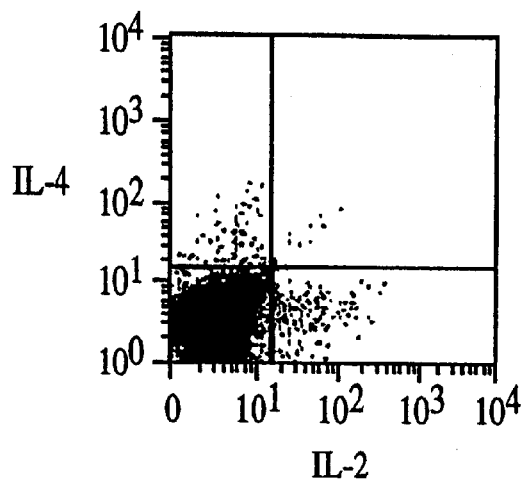
Figures 2, 18B:
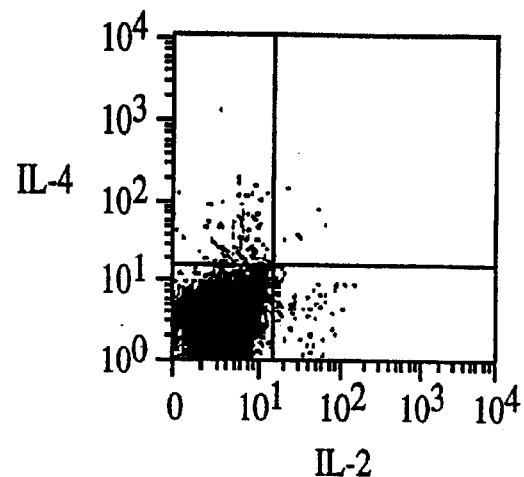
Figures 3, 18B:
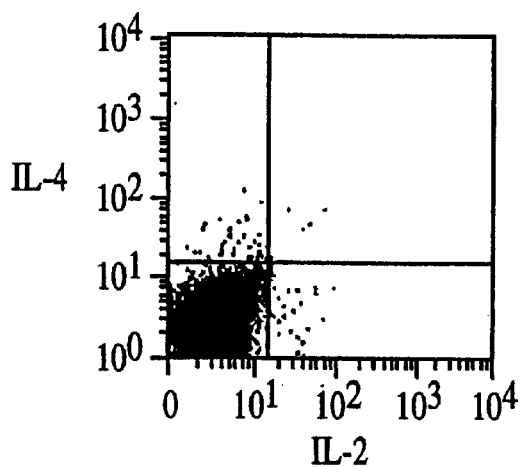
Figures 4, 18B:
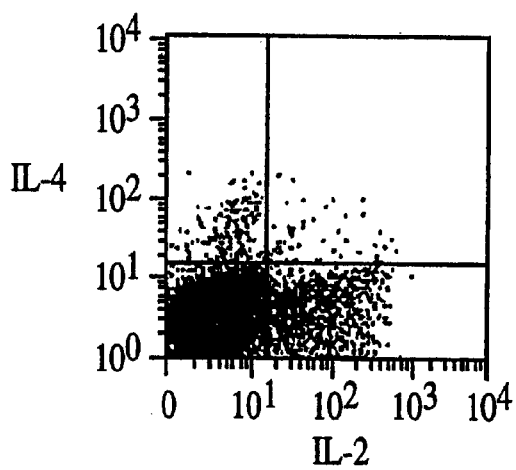

To determine if the diminished help observed in the above experiments by $CD4^+$ T cells from peptide treated mice was due to anergy or deletion, rIL-2 was added at the beginning of the 7-day culture period to the helper assay co-cultures, in a range of concentrations from 12.5 to 100 units per milliliter. The results of these experiments are shown in FIG. 4. The saline-injected control group mice produced 102±15.5 units of anti-dsDNA antibody per deciliter. The addition of rIL-2 increased this antibody production by only a small amount. $CD4^+$ T cells from the $H4_{71-94}$, and $H2B_{10-33}$ injected mice did not exhibit any increase in their ability to help in anti-dsDNA antibody production after the addition of rIL-2. T cells from the $H4_{16-39}$ treated group mice, exhibited only a modest increase of 35% in help for anti-dsDNA antibody production following the addition of rIL-2 (p=0.05). The $H4_{16-39}$ group mice also exhibited a 30% increase in anti-ssDNA antibodies and a 20% increase in anti-nucleosome antibodies, but these increases were not significant relative to the increases in control group mice.

Figure 5:
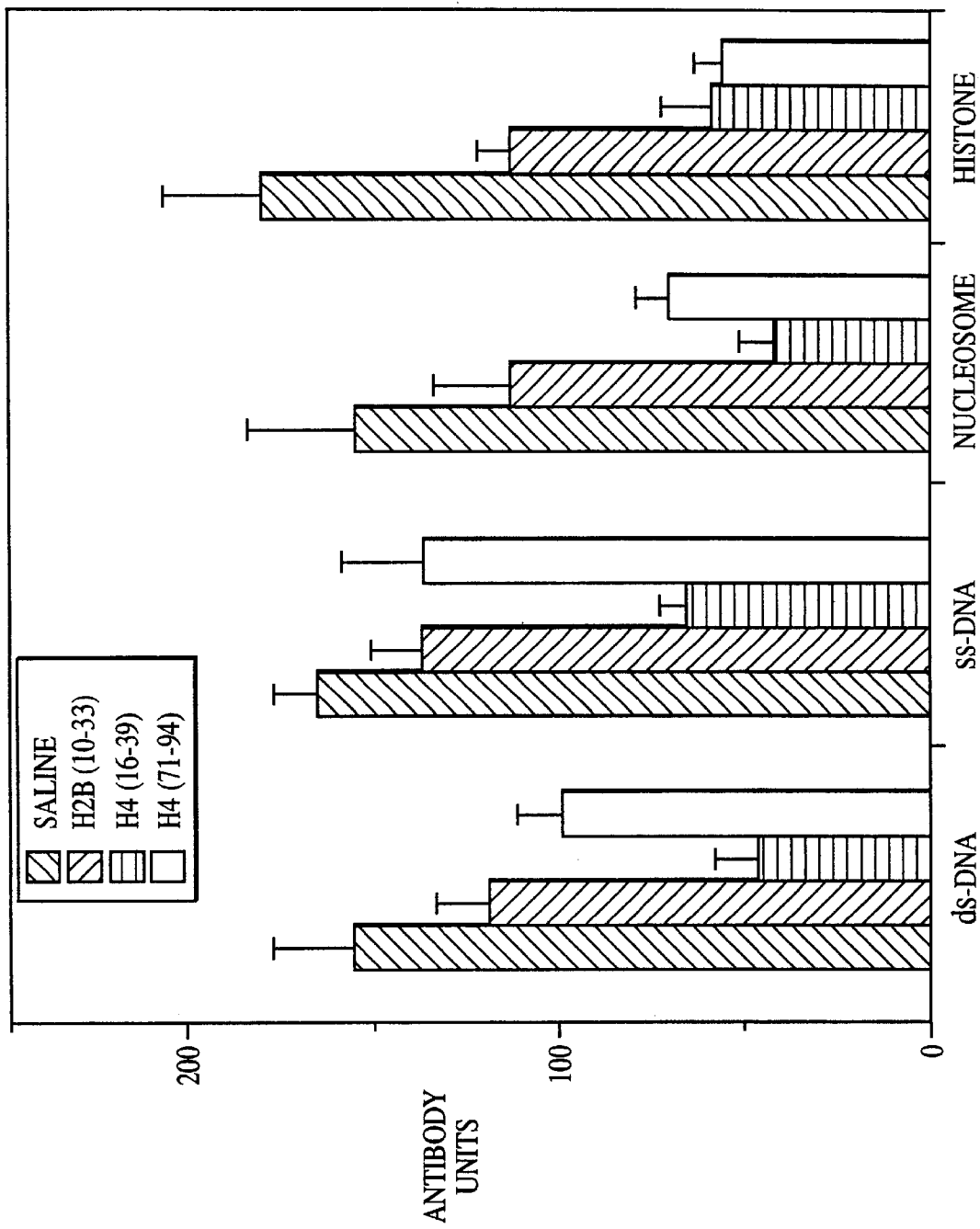
FIG. 5 is a graph depicting the effect of peptide therapy on the ability of B cells obtained from treated mice to receive help (i.e. facilitation in initiating autoantibody production) from Th cells. The amount of IgG autoantibodies produced is expressed as a mean number of units per deciliter of culture medium±SEM of five experiments. The base line autoantibody levels produced by B cells cultured alone were: anti-dsDNA, 2.4±0.96; anti-ssDNA, 2.1±0.34; anti-nucleosome, 2.5±1.9; and anti-histone, 1.3±1.0.

Effect of Peptide Therapy on the Ability of Autoimmune B Cells to Receive T Cell Help The effect of peptide therapy on the immune function of B cells was determined by co-culturing B cells from tolerized (i.e. peptide injected) mice with $CD4^+$ T cells from unmanipulated $SNF_1$ mice, and performing the helper assay using these co-cultures. In the presence of T helper cells, the B cells from the peptide-injected and control groups of mice did not exhibit any difference in their ability to produce IgG autoantibodies, with the exception of the $H4_{16-39}$ group mice B cells, which still produced diminished levels of all autoantibodies in co-culture experiments. As shown in FIG. 5, the level of anti-dsDNA antibodies produced by B cells from $H4_{16-39}$ injected mice (45±10.1 units per deciliter) was significantly reduced in comparison to control mice (160±18.5 units per deciliter) (p=0.03). Production of anti-ssDNA antibodies exhibited a similar pattern: the control group B cells produced 170±10.9 units per deciliter compared with the $H4_{16-39}$ group B cells which produced 60±7.9 units (p=0005). Production of anti-nucleosome antibodies was reduced by three fold in the $H4_{16-39}$ group mice relative to the control group mice, and anti-histone antibody production was reduced by approximately 4-fold (p=0.003) in $H4_{16-39}$ injected mice relative to control group mice. In $H4_{71-94}$ injected mice, production of anti-nucleosome (p=0.01) and anti-histone (p=0.003) antibodies, but not production of either anti-dsDNA or anti-ssDNA antibodies, remained significantly low relative to control group mice.

The baseline values for antibody production by B cells cultured alone ranged from 1.3 to 2.5 units per deciliter of culture medium in these experiments.

Figure 6:
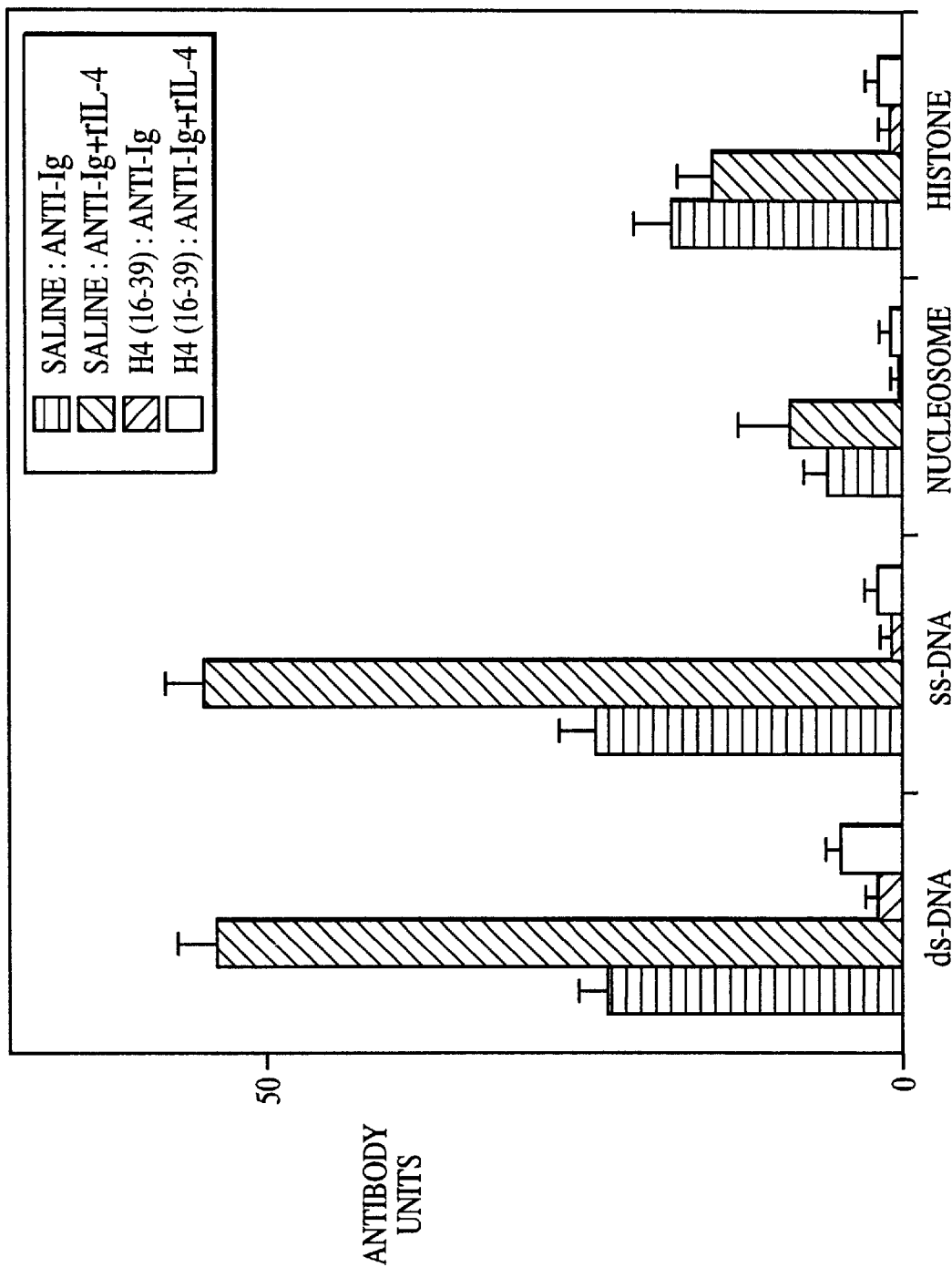
FIG. 6 is a graph depicting the effect of $H4_{16-39}$ peptide treatment on diminishing autoimmune B cells as assessed the absence of recovery of these cells following stimulation with either anti-Ig or anti-Ig and IL-4. Autoantibody production is expressed as a mean number of units per deciliter of culture supernatant±SEM of five experiments. The base line autoantibody levels produced by B cells cultured alone were: anti-dsDNA, 2.1±0.72; anti-ssDNA, 1.9±0.1; anti-nucleosome, 1.9±1.0; and anti-histone, 2.0±1.6.

Effect of Anti-Ig $(Fab')_2$, and rIL-4 on B Cells from $H4_{16-39}$—Treated Group of Mice As indicated by the above experimental results, B cells from $H4_{16-39}$ peptide-injected mice were less responsive to help from T cells of unmanipulated $SNF_1$ mice. In order to assess, whether this impairment was due to deletion or anergy, purified B cells from the $H4_{16-39}$ group mice were stimulated with anti-Ig $(Fab')_2$ in the presence or absence of rIL-4, and the production of IgG antibodies to dsDNA, ssDNA, nucleosomes and histones was measured. The results of these experiments are shown in FIG. 6. The B cells from control group mice produced high levels of antibodies, whereas B cells from the $H4_{16-39}$ group mice did not respond by increasing antibody production, even when stimulated with anti-Ig $(Fab')_2$ in the presence of high levels of rIL-4. This result suggested that deletion of autoimmune B cells may be partly responsible for reduced B cell responses. However, B cells from $H4_{71-94}$ group mice could be stimulated to produce autoantibodies at levels similar to those of the control mice. The basal level of antibody production by B cells cultured alone in these experiments ranged from 1.9 to 2.1 units per deciliter of culture medium.

Figure 7:
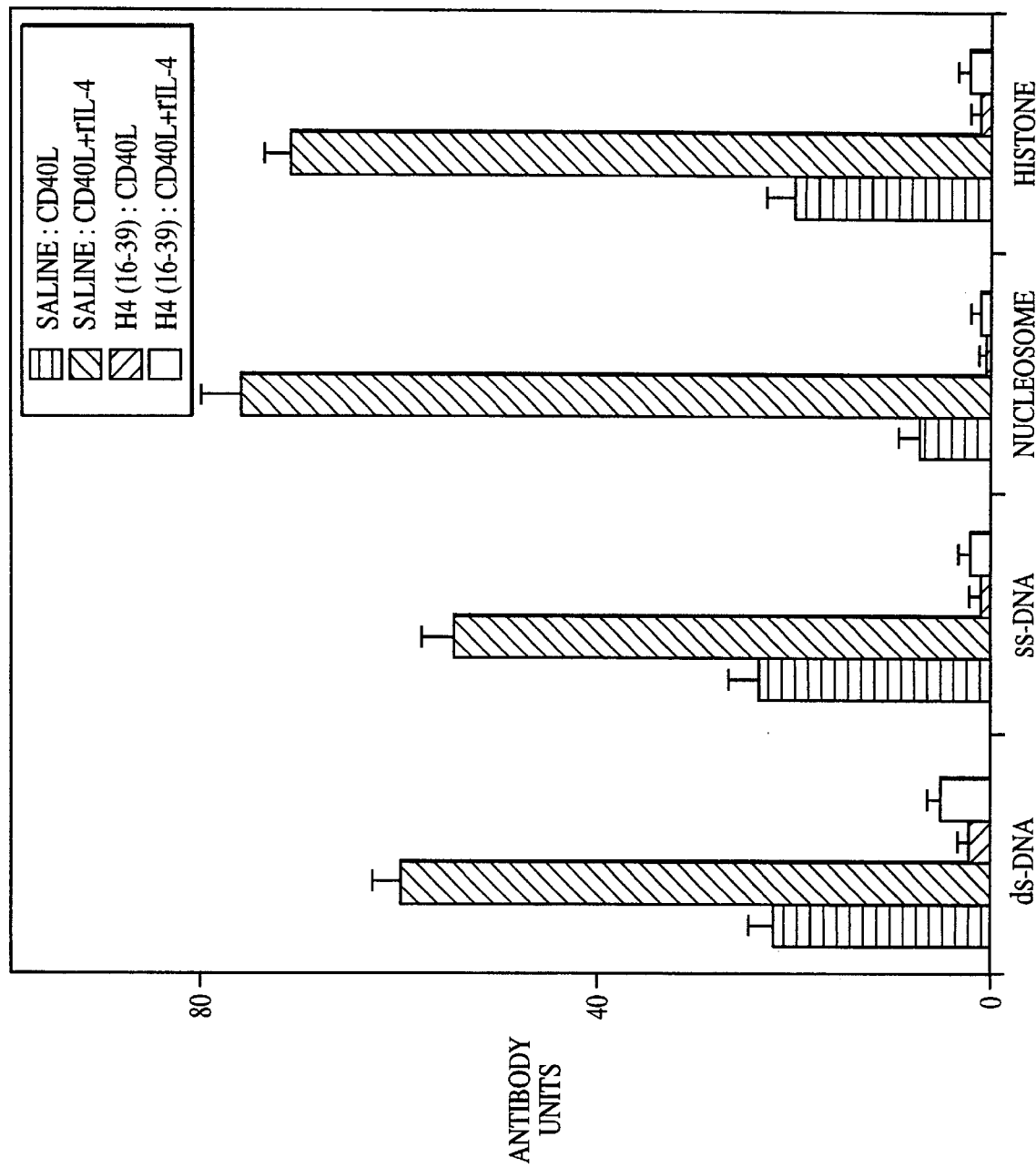
FIG. 7 is a graph depicting the effect of soluble CD40 ligand (CD40L) and IL-4 stimulation on B cells obtained from mice treated with either a saline solution or a solution comprising the $H4_{16-39}$ peptide. The results are expressed as a mean number of antibody units per deciliter of culture medium±SEM of five experiments.

Effect of Soluble CD40 Ligand and rIL-4 on B Cells of $H4_{16-39}$ Injected Mice In order to assess whether other molecules may be involved in autoantibody production, B cell cultures were incubated in a culture medium comprising HL-1 serum free medium, and soluble CD40L-CD8 fusion protein (CD40L) in a ratio of 4 to 1 with or without rIL-4. As shown in FIG. 7, purified (i.e. T-cell depleted) B cells from the control group mice produced anti-nuclear antibodies upon stimulation with CD40L. The addition of rIL-4 to these cultures enhanced the production of antibodies by B cells from the control group mice even further. However, a comparison of FIGS. 5 and 7 reveals that the increase in levels of antibody production with addition of soluble CD40L and rIL-4 were much less than with the addition of intact Th cells from autoimmune mice, indicating that additional molecules might be involved. B cells from the $H4_{16-39}$ group mice did not produce significant amounts of antibodies, even with the addition of CD40L and rIL-4.

B Cell Response to Lipopolysaccharide (LPS) in Peptide Injected Mice

Figure 8:
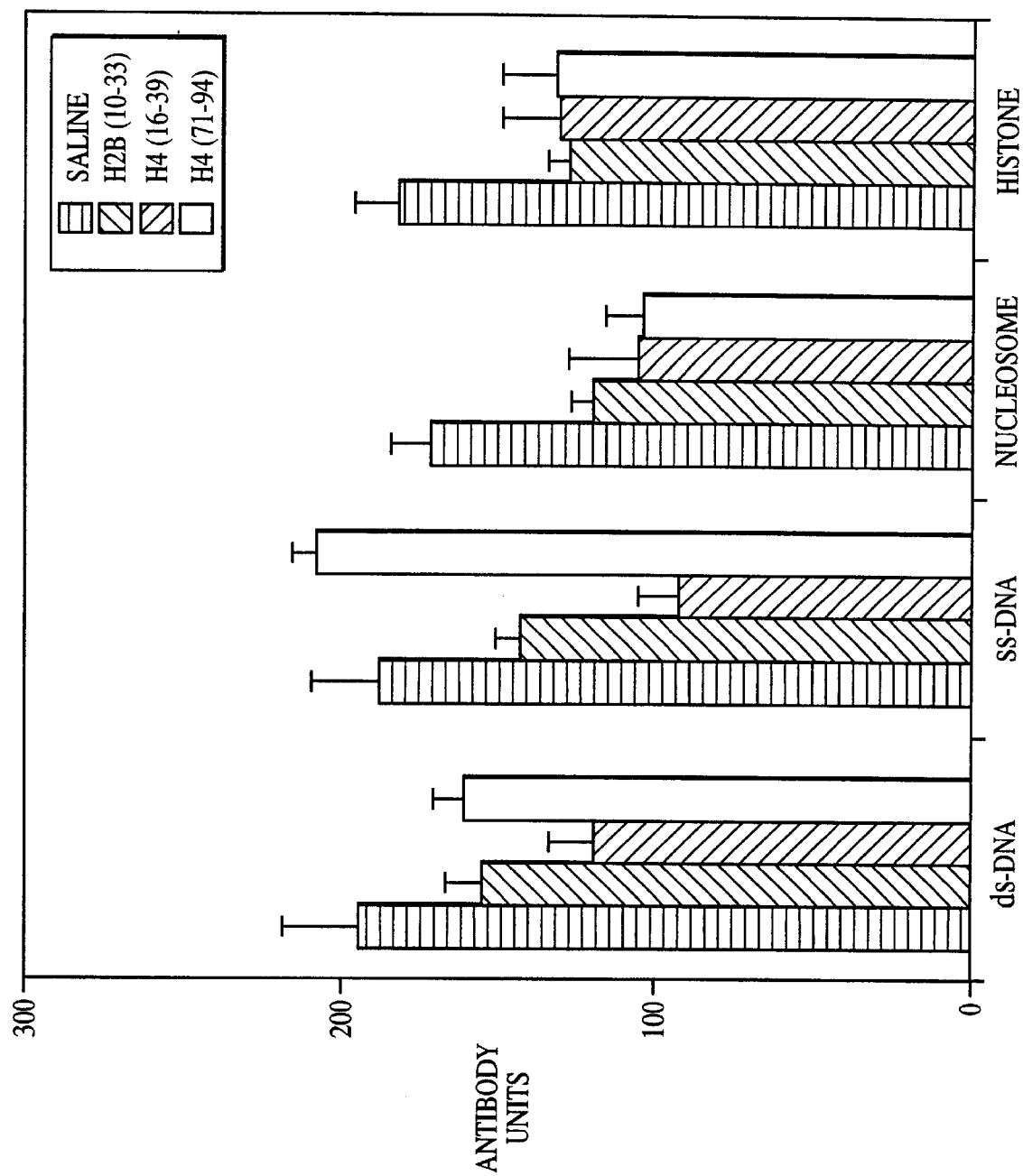
FIG. 8 is a graph depicting the response to lipopolysaccharide (LPS) by B cells from peptide-injected mice. The results are expressed as a mean number of antibody units per deciliter of culture supernatant±SEM of five experiments. The base line autoantibody levels produced by B cells cultured alone were the same as those shown in FIG. 6.

Purified B cells were isolated from peptide-injected mice and stimulated with the potent mitogen, LPS. As shown in FIG. 8, B cells from all the groups of mice responded with increases in antibody production which were comparable to increases observed in the control group mice (p=0.07 to 0.1).

IgG Anti-nuclear Autoantibody Levels in Sera of Peptide Injected Mice

Figure 9C:
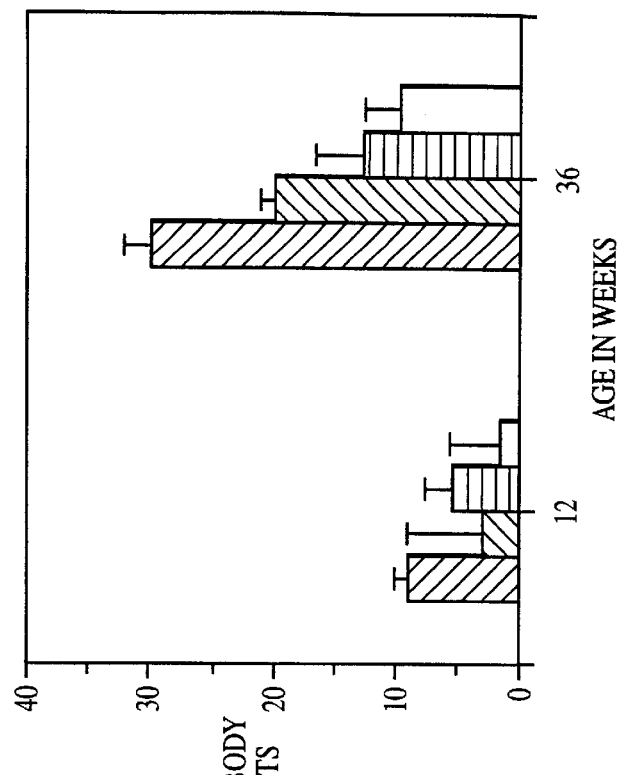
Figure 9D:
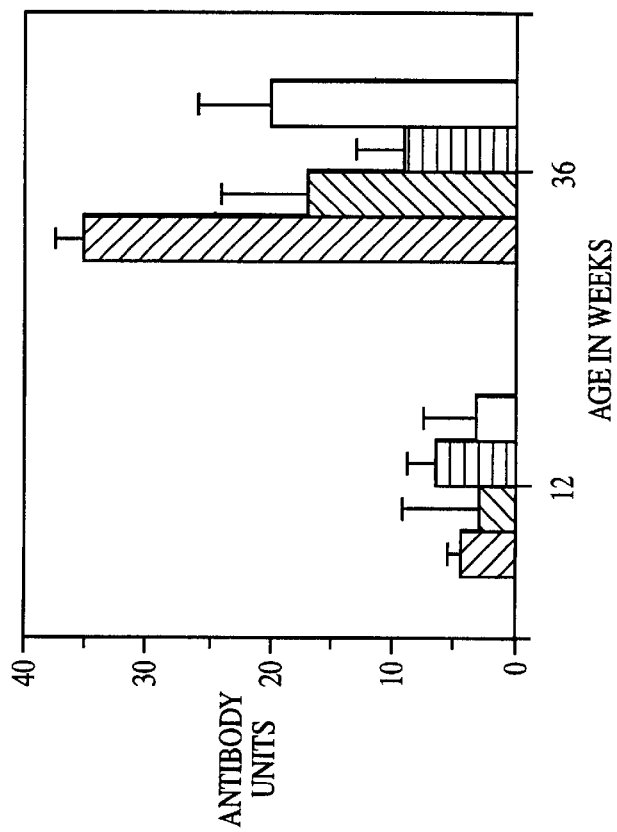

For the brief therapy experiments, sera were collected from 12 week old mice at the start of treatment, again at 36 weeks of age, and finally, at the peak of the severe nephritis. IgG antibody levels were measured for anti-dsDNA, anti-ssDNA, anti-nucleosome, and anti-histone antibodies using a 1:400 dilution of sera from mice. As shown in FIG. 9, the anti-dsDNA antibody level in the control group was 5.5±0.3 units, and in the $H2B_{10-33}$, $H4_{16-39}$, and $H4_{71-94}$ groups mice, the levels of anti-dsDNA were 7.7±0.9, 9.0±2.1, and 5.4±1.1 units, respectively, at the start of treatment. At 36 weeks of age in the control group, anti-dsDNA levels rose to 26±3.2 units. This level was 14.0±3.2, 13.0±4.0, 17.1±2.7 units in the $H2B_{10-33}$, $H4_{16-39}$, and $H4_{71-94}$ groups, respectively (p 0.03 to 0.05). Time point comparisons among the groups of mice revealed a reduction in anti-ssDNA antibody levels and anti-nucleosome antibody levels in sera from peptide-injected mice which was comparable to the reduction observed in their anti-ds-DNA antibody levels (p from 0.04 to 0.05). The levels of anti-histone antibodies varied among the groups (p=0.3 to p=0.01). At the time of sacrifice, when the mice had developed severe nephritis, the serum levels of antibodies were similar among all groups of mice. Total polyclonal IgG levels were not significantly different in the peptide-injected group mice relative to the control group mice varying from 8–11 milligrams per milliliter.

Search for Regulatory T Cells in Peptide-Injected Mice

In order to determine if any regulatory T cells might have been generated by peptide injection, the ability of the T cells from tolerized mice to inhibit autoantibody production in co-cultures of T and B cells from unmanipulated $SNF_1$ mice was determined. T cells or purified CD4+ or CD8+ subsets of T cells from short-term experiment mice in either the tolerized or control groups were co-cultured with unmanipulated $SNF_1$ splenic B and T cell mixtures in 24-well plates for 7 days. IgG antibody production in these cultures against ssDNA, dsDNA, histones, and nucleosomes was estimated using an ELISA. No significant reduction in antibody production by the addition of T cells from peptide-injected mice was observed.

Treatment of Established Glomerulonephritis with Nucleosomal Peptides

Figure 10:
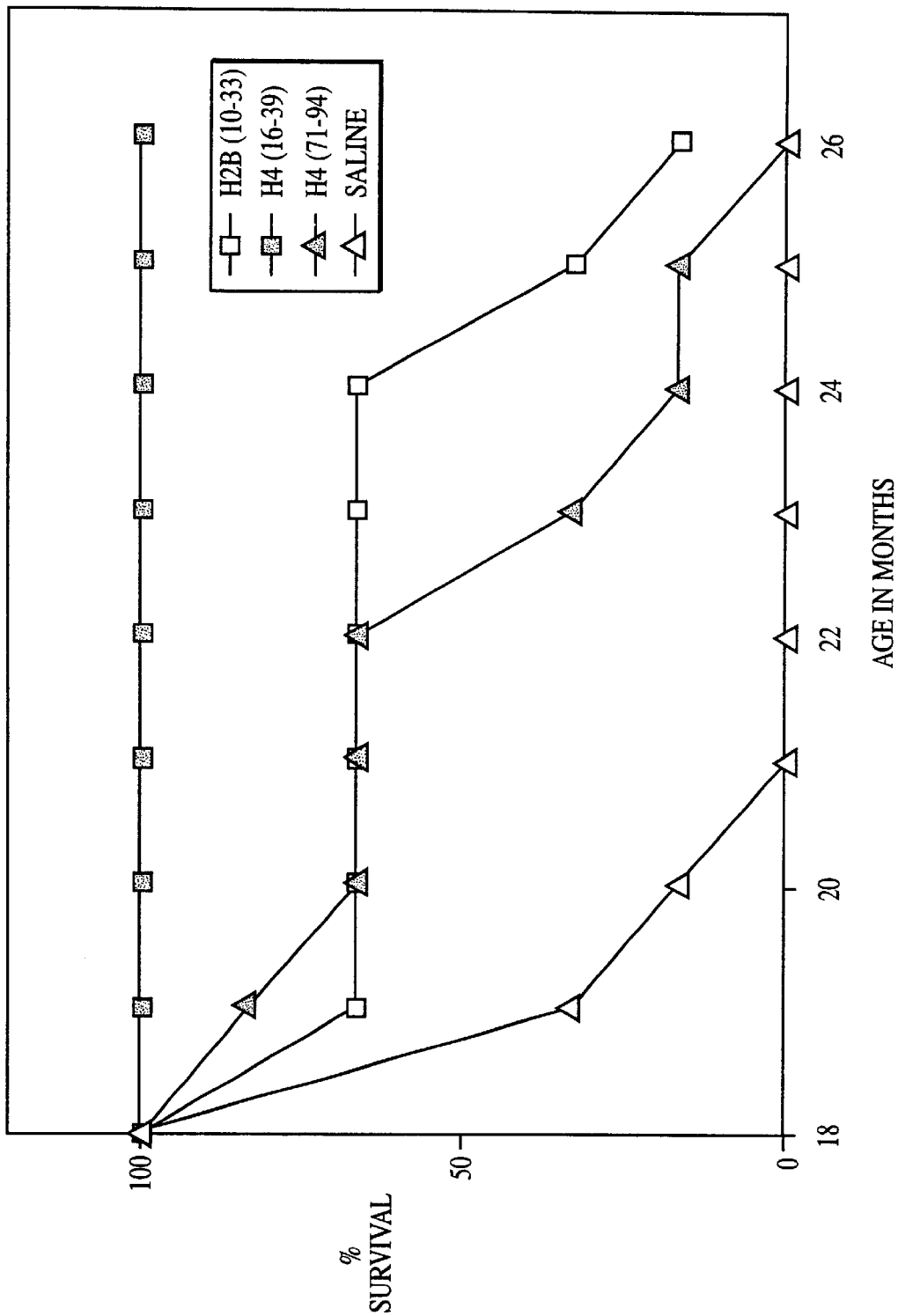
FIG. 10 is a graph depicting the results of experiments in which nucleosomal peptides were chronically administered to mice with established SLE-associated nephritis. The data represent the monitoring of proteinuria in mice until they died of kidney disease. The results are expressed as the percentage of mice that survived.

The results of chronic therapy experiments using 18-month old mice with established glomerulonephritis are shown in FIG. 10. The control group mice exhibited rapid progression of disease and died within two months after the start of the treatment. At this time point, 66.6% of the mice in the $H4_{71-94}$ and $H2B_{10-33}$ groups of mice were alive (p=0.061), whereas none of the mice in $H4_{16-39}$ group had died (p=0.002). All the tolerized groups maintained their starting levels of proteinuria during the course of the experiment, with the exception of the $H4_{16-39}$ group, in which 66.6% of the animals actually exhibited a reduction in proteinuria levels from 300–1000 milligrams per deciliter to less than 100 milligrams per deciliter. By 26 months age, all of the $H4_{16-39}$ group mice remained alive. By contrast, all of the $H4_{71-94}$ group mice had succumbed to renal disease (p=0.002), and only one mouse in the $H2B_{10-33}$ group survived (p=0.015 as compared with the $H4_{16-39}$ group).

Figure 11:
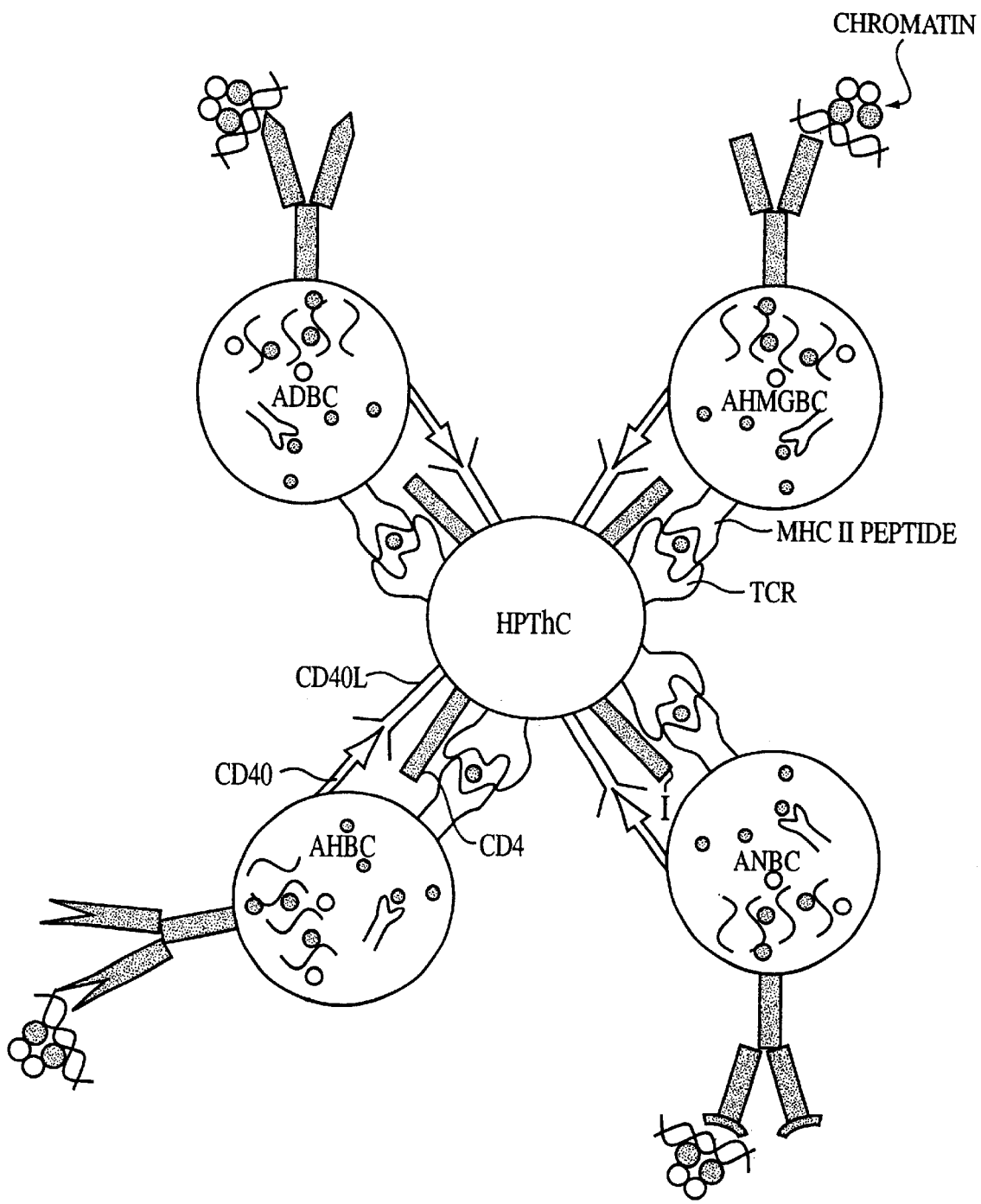
FIG. 11 depicts a proposed model for the production of diverse autoantibodies in SLE by multipotent, intermolecular T-cell help.
Figure 12A:
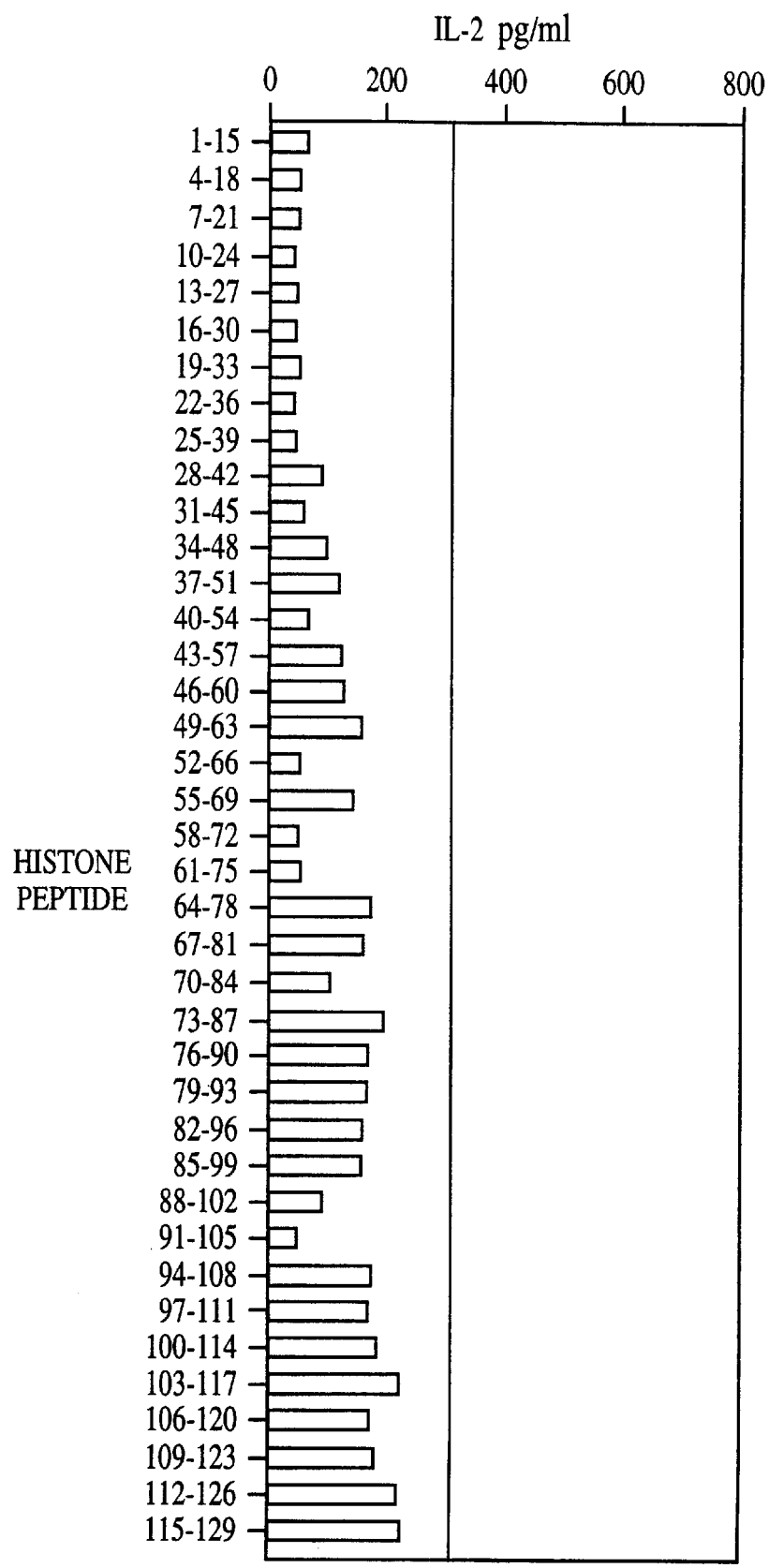
FIGS. 12A–12D, is a series of graphs depicting IL-2 production by a pathogenic CD4$^+$ T cell line in response to selected nucleosomal histone peptides which were overlapping 15-mers. The cell line was derived from CD4$^+$ T cell clone, DD2. An autologous EBV-B cell line incubated briefly (i.e. pulsed) with a selected histone peptide acted as the antigen presenting cell (APC) line in these experiments. The results depicted represent the mean of triplicate experiments. In this figure, values higher than 3 SD (designated by the horizontal line) above the mean of background were considered stimulatory. The background production of Il-2 by the T cell clone DD2 cultured with APC without added peptide was on the average 132 picograms of IL-2 per milliliter of culture supernatant. IL-2 production by T cell clone DD2 in response to anti-CD3 stimulation was 554 picograms per milliliter. Peptides corresponding to H2A histone protein are shown in FIG. 12A. Peptides corresponding to H2B histone protein are shown in FIG. 12B. Peptides corresponding to H3 histone protein are shown in FIG. 12C. Peptides corresponding to H4 histone protein are shown in FIG. 12D.
Figure 12B:
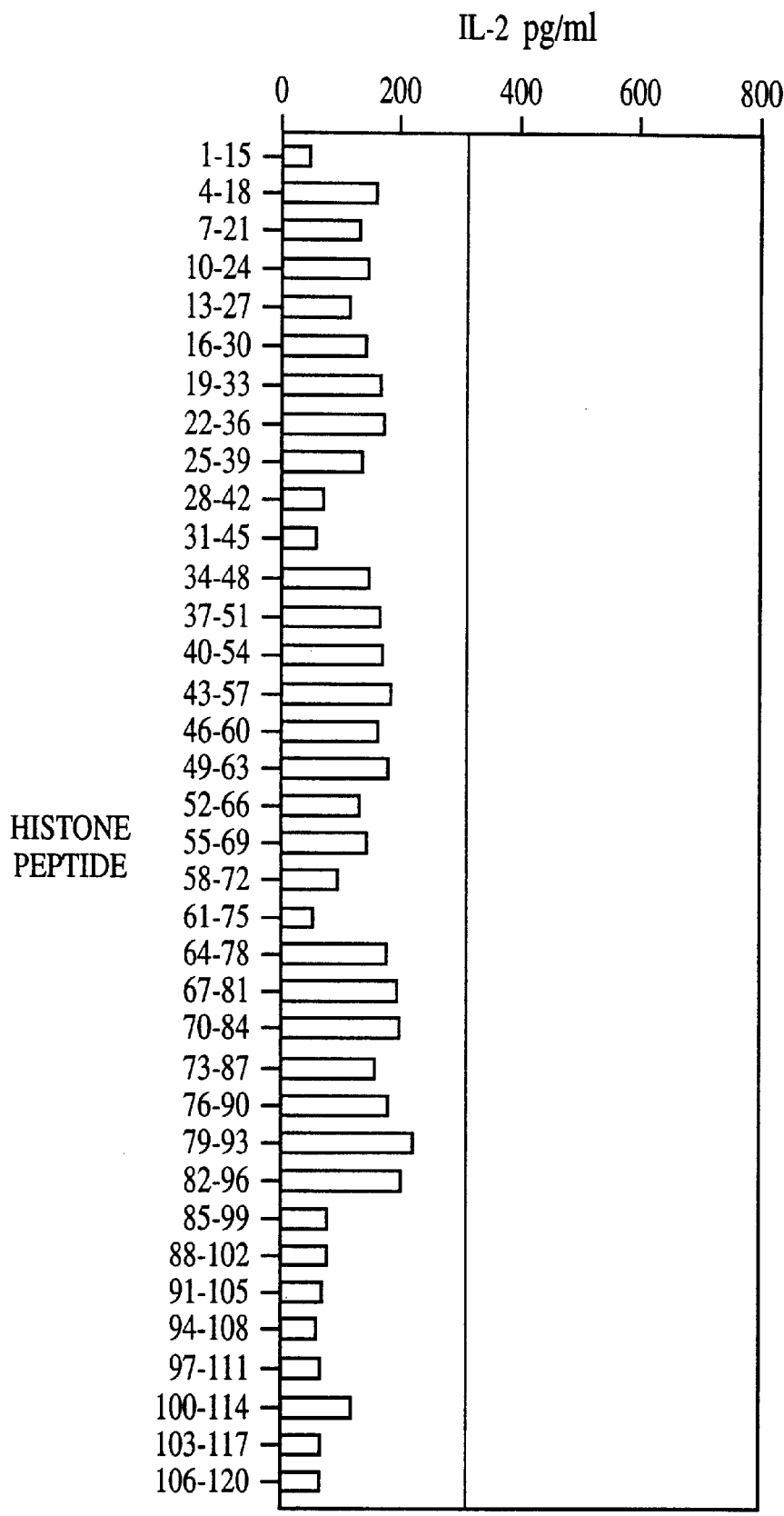
Figure 12C:
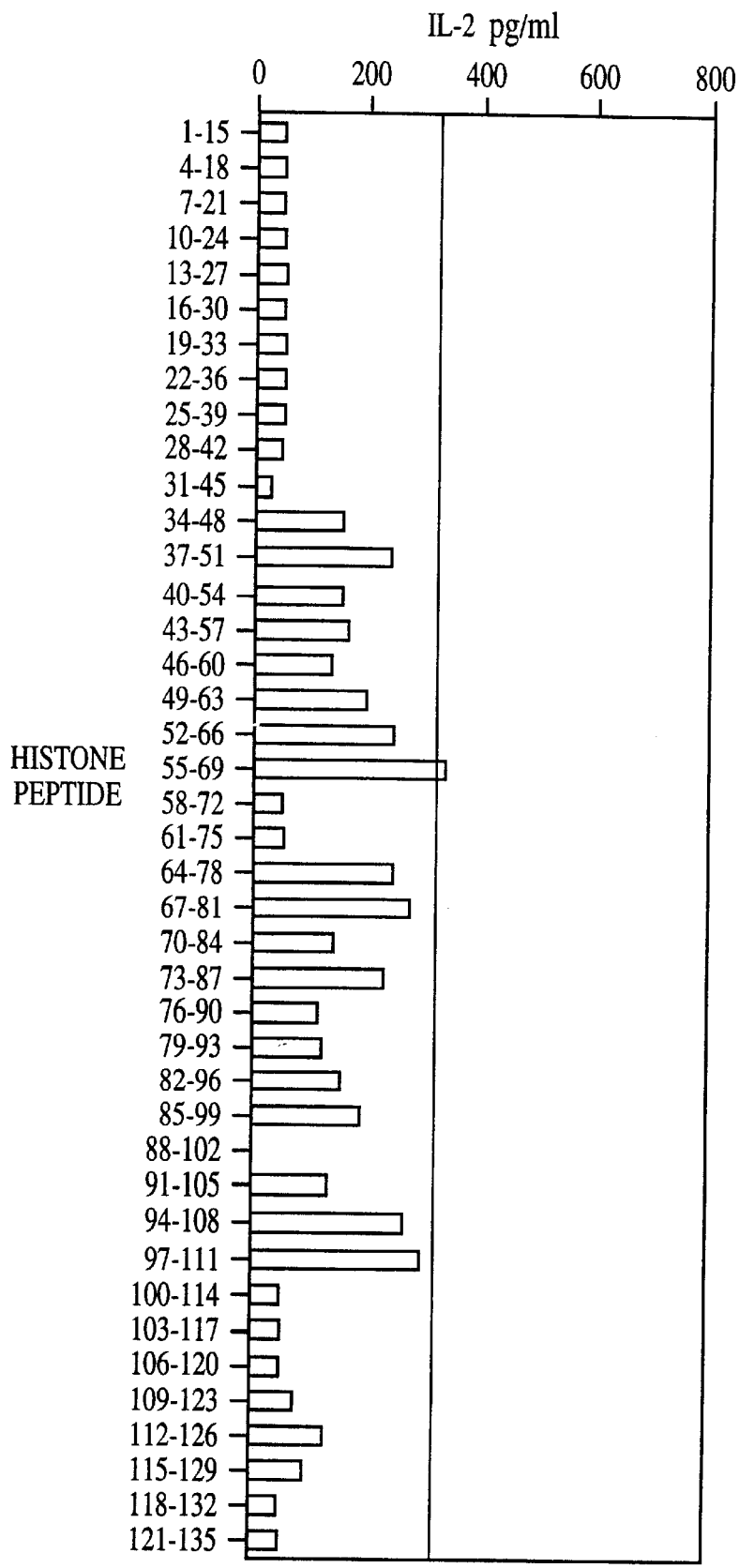
Figure 12D:
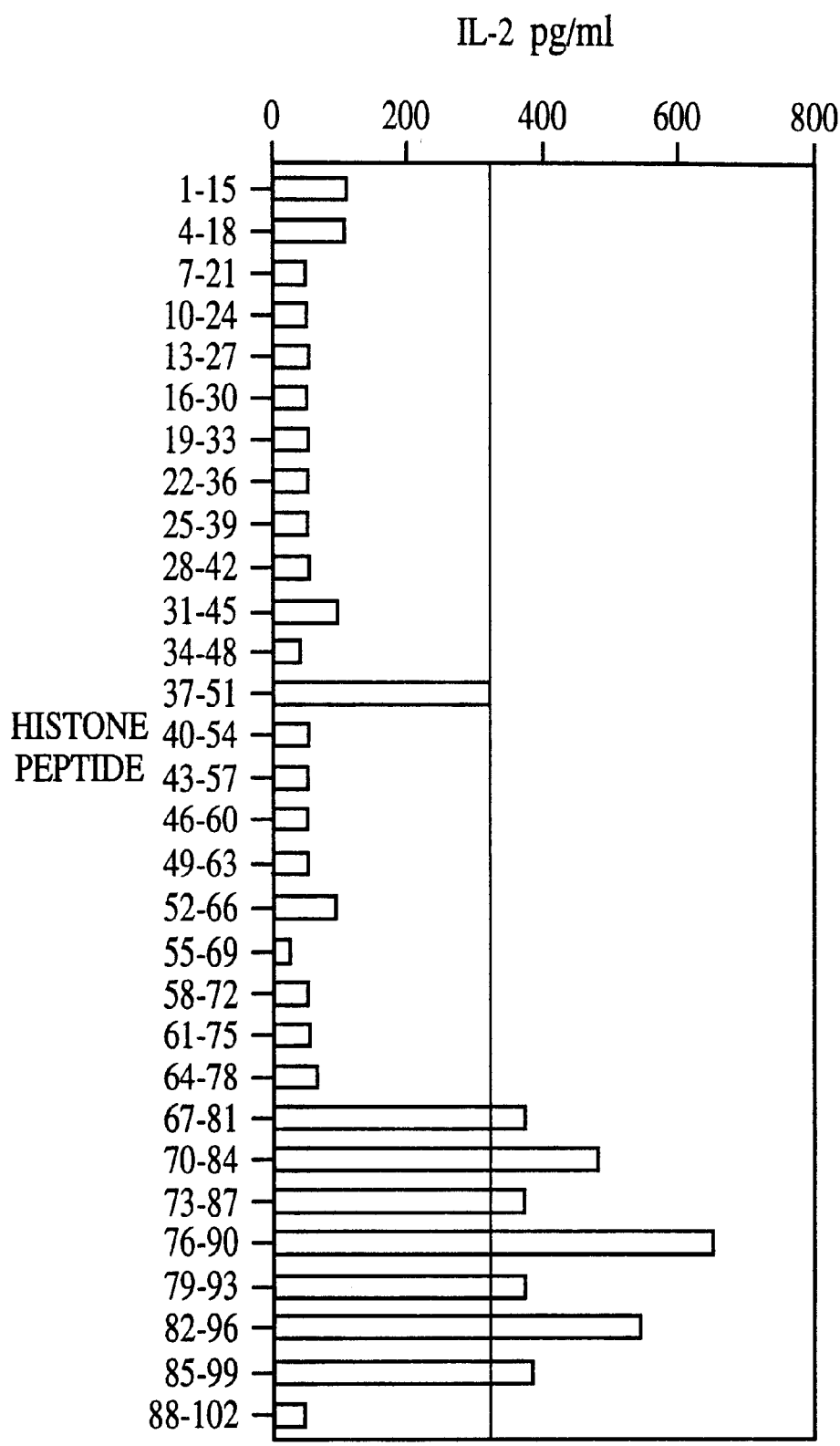

The multipotent and promiscuous helper activity of the pathogenic Th cells involved in SLE which is evident from these experiments is modelled in FIG. 11. This proposed model takes into account that a single lupus T helper clone appears to have been able to help different B cells which are specific for either dsDNA, ssDNA, histone, or nucleosomes. This could result from each of these B cells binding to its respective antigenic determinant on a whole chromatin particle, taking up and processing the chromatin, and presenting the relevant histone peptide epitope in the chromatin to the Th clone (Mohan et al., 1993, J. Exp. Med. 177:1467; Desai-Mehta, 1995, J. Clin. Invest. 95:531; Datta and Kaliyaperumal, 1997, Annals. New. York Acad. Sci. 815:155). The result of the interaction is that intermolecular help is provided to the different B cells by the same Th cell. The multipotent Th cells associated with SLE cause immediate epitope diversification, rather than the sequential epitope spreading seen in other types of inflammatory damage and progression of other autoimmune disease (Kalled et al., 1998, J. Immunol. 160:2158; Lehman et al., 1992, Nature 358:155; Craft and Fatenejad, 1997, Arthritis Rheum. 40:1374).

The experiments described in this Example demonstrate that despite an intrinsic polyclonal hyperactivity and a lowering of the threshold of activation observed previously (Datta et al., 1982, J. Immunol. 129:1539; Klinman and Steinberg, 1987, J. Exp. Med. 165:1755; Chan and Shlomchik, 1998, J. Immunol. 160:51; Jongstra-Bilen, 1997, J. Immunol. 159:5810; Mohan et al., 1995, J. Immunol. 154:1470; Desai-Mehta et al., 1996, J. Clin. Invest. 97:2063; Koshy et al., 1996, J. Clin. Invest. 98:826; Liossis et al., 1996, J. Clin. Invest. 98:2549), pathogenic T and B cells of established lupus can be functionally downregulated with injection of peptides corresponding to the appropriate autoepitopes.

Among the three nucleosomal peptides described herein, $H4_{16-39}$ exhibited the most beneficial effect. Interestingly, this peptide is not the most immunogenic among the nucleosomal autoepitopes in triggering pathogenic Th cells in $SNF_1$ mice (Kaliyaperumal et al., 1996, J. Exp. Med. 183:2459), nor does it have the highest affinity for MHC class II molecules (Shi et al., 1998, J. Exp. Med. 187:367). However, $H4_{16-39}$ administered intravenously, was able to tolerize both the autoimmune Th cells and the B cells involved in lupus. Autoimmune memory B cells were probably most affected by this peptide, as they could not be rescued by CD40L/IL-4, or anti-Ig/IL-4 stimulation. Addition of autoimmune Th cells from unmanipulated $SNF_1$ mice did increase autoantibody production by B cells from the $H4_{16-39}$ injected mice above baseline, but not comparably relative to other groups.

As shown in this Example, the overlapping of epitopes for pathogenic Th cells and autoimmune B cells of lupus makes $H4_{16-39}$ a highly efficient tolerogen, and this principle might be relevant to other autoimmune diseases as well (Tung et al., 1997, Current Opin. Immunol. 9:839; Wucherpfennig et al., 1997, J. Clin. Invest. 100:1114). An additional epitope was identified in nucleosomal core histone H3, $H3_{85-102}$, to which splenic T cells of pre-nephritic $SNF_1$ mice spontaneously responded. (Kaliyaperumal et al., 1996, J. Exp. Med. 183:2459). Interestingly, this T-cell epitope is also bound by spontaneously arising anti-DNA autoantibodies of lupus (Stemmer et al., 1996, J. Biol. Chem. 271:21257). Future studies should determine if $H3_{85-102}$ is also a potent tolerogen for therapy of lupus nephritis in $SNF_1$ mice. Thus, autoantigen-experienced and presumably memory T and B cells of lupus can be functionally inactivated, at least for their ability to produce pathogenic autoantibodies by tolerogenic therapy with nucleosomal peptides. Finally, despite tolerance spreading, the peptide treated mice did not develop any generalized immunosuppression. They were housed in conventional cages and their total serum IgG levels were not affected by the therapy.

The data presented in this Example can be summarized as follows.

Using the $(SWR \times NZB)F_1$ ($SNF_1$) mouse model of lupus, the critical autoepitopes have been identified. Nephritis-inducing Th cells are stimulated by autoepitopes present in the core histones of nucleosomes, at amino acid positions 10–33 of H2B, 85–102 of H3, and 16–39 and 71–94 of H4. The experiments in this Example demonstrate that brief therapy with the peptides administered intravenously to $SNF_1$ mice that were already producing pathogenic autoantibodies, markedly delayed the onset of severe lupus nephritis. Strikingly, injection of these peptides into mice with established glomerulonephritis, resulted in prolonged survival and halted the progression of renal disease. Remarkably, tolerization with any one of the nucleosomal peptides impaired autoimmune T-cell function, thereby inhibiting the production of multiple pathogenic autoantibodies. Moreover, suppressor T cells were not detected in the injected mice. The most promising effect was obtained using nucleosomal peptide H4$_{16-39}$, which had a tolerogenic effect not only on autoimmune Th cells, but on autoimmune B cells as well.

EXAMPLE 2

Major Peptide Autoepitopes for Nucleosome-Specific T Cells of Human SLE

In the experiments presented in this Example, overlapping peptides spanning the entire length of the core histones of nucleosomes have been tested for their ability to stimulate established T helper cell lines and primary T helper cell isolates from 23 SLE patients. The peptide autoepitopes in nucleosomes that are recurrently recognized by the autoimmune T cells of patients with SLE are identified herein. These Th cells are essential for sustaining the pathogenic autoantibody-producing B cells associated with SLE (Datta et al. 1987, J. Exp. Med. 165:1252–1268; Shivakumar et al. 1989, J. Immunol. 143:103–112; Ray et al., 1996, Proc. Natl. Acad Sci. USA. 93:2019–2024; Mohan et al., 1995, J. Immunol. 154:1470–1480).

The materials and methods used in this Example are now described.

Patients and Healthy Donors

The short-term CD4$^+$ T cell lines were derived from a patient group consisting of five female patients with active SLE ranging in age from 21–51 years, five female patients in long term SLE remission, ranging in age from 21–51 years, and normal healthy subjects, two male and four female, ranging in age from 24–52 years. Peripheral blood mononuclear cells (PBMC) used to study intracellular cytokine production were obtained from a separate patient group consisting of eight patients in long term SLE remission, including two males and six females, ranging in age from 28 to 55 years, and four female patients with active SLE, ranging in age aged from 22 to 47 years.

Disease activity by Systemic Lupus Activity Measure (i.e. SLAM), ranged between 7 and 20 for active patients (Liang et al., 1989, Arthritis. Rheum. 32:1107–1118). None of the patients in remission had detectable proteinuria or serum anti-DNA autoantibodies at the time of testing, and their SLAM ranged between 0 and 4. The patients in remission had never received any cytotoxic drugs, and were not receiving any steroids at the time their blood samples were drawn. Steroids had been discontinued for several years in the remission patients, except for two patients who had received a short course of low dose steriods (Prednisone, 10 milligrams per day) 2 months before the assays were performed.

Antibodies

A hybridoma (OKT3) which produces Anti-CD3 antibody (i.e. mAb) was obtained from the American Type Culture Collection (Rockville, Md.). The hybridoma supernatants were concentrated by precipitation in a solution comprising 47% saturated ammonium sulfate, and dialyzed before use. Anti-CD28 antibody (clone 9.3) containing ascites was provided by Bristol Myers Squibb (Seattle, Wash.). Purified mAbs used for ELISAs were purchased from Pharmingen (San Diego, Calif.). PE-conjugated mAb to human IL-10 and FITC-conjugated mAb to human IL-2 were purchased also from Pharmingen. PE-conjugated mAb to human IL-4, FITC-conjugated mAb to human IFN-γ, PerCP-conjugated anti-human CD4 and purified anti-human CD28 (clone L293) were purchased from Becton-Dickinson (San Jose, Calif.).

Antigens

All the peptides used in the experiments presented in this Example were synthesized by the pin method (Chiron Mimotopes, San Diego, Calif.), and purity of the peptides was verified by amino acid analysis (Kaliyaperumal et al., 1996, J. Exp. Med 183:2459–2469). Overlapping peptides comprising 15 amino acids each were designed to span the entire stretch of all four core histones, with each peptide overlapping at least one other peptide by 12 residues. Peptides used for intracellular cytokine response studies were core histone peptides comprising either 15 amino acids or 24 amino acids. The sequences of these peptides (SEQ ID Nos: 1–26), as well as those used elsewhere herein, are shown in FIG. 17 and Example 3. Nucleosomes were prepared as described previously (Mohan et al., 1993, J. Exp. Med. 177:1367–1381; Kaliyaperumal et al., 1996, J. Exp. Med 183:2459–2469.

Cell Preparation

PBMCs obtained from either patients or healthy donors were isolated from heparinized venous blood by density gradient sedimentation using Ficoll-Hypaque as a gradient matrix (Pharmacia LKB Biotechnology Inc., Piscataway, N.J.). Isolated PBMCs were washed twice in RPMI 1640 culture medium, and aliquots of the cells suspended in media were used to generate both short-term T cell lines and EBV-transformed B cell lines. Others cells were either used directly for stimulation with antigens or frozen into liquid nitrogen.

To make short-term, CD4$^+$ T cell lines, CD4$^+$ T cells were purified from PBMC using magnetic beads absorbed with anti-CD4 mAb, followed by using DetachBeads (Dynal Inc., Oslo, Norway). The CD4$^+$ T cells were expanded by one round of stimulation with plate-bound anti-CD3 mAb, anti-CD28 (clone 9.3) mAb, and rIL-2 (20 units per milliliter) in RPMI 1640 medium supplemented by 10% human AB serum (Pel-Freez Biologicals, Brown Deer, Wis.). The expanded T cells were frozen in liquid nitrogen within two weeks of culture using standard protocols and reagents.

EBV-B cell lines used as antigen presenting cells in co culture were generated as described previously. (Rajagopalan et al., 1990, Proc. Natl. Acad. Sci. 87:7020–7024; Desai-Mehta et al., 1995, J. Clin. Invest. 95:53 1–541).

The CD4$^+$ T cell clone DD2 was derived from a patient with active SLE and associated nephritis (Rajagopalan et al., 1990, Proc. Natl. Acad. Sci. 87:7020–7024; Desai-Mehta et al., 1995, J. Clin. Invest. 95:531–541).

Stimulation of Short-Term T Cell Lines

Short-term T cell lines were rapidly thawed from liquid nitrogen and expanded in the presence of plate-bound anti-CD3 mAb, anti-CD28 mAb, and rIL-2 (20 units per milliliter). The expanded cells were transferred to fresh culture wells and rested by incubating in fresh medium for 10 to 14 days. For stimulation assays, 96 well plates were coated with 2 micrograms per milliliter of goat anti-mouse IgG antibodies overnight at 37° C. After washing the plates twice with Dulbecco's phosphate-buffered saline (dPBS), autologous and previously irradiated (3,000 rad) EBV-B cells (APC) were first added to each well at a concentration of 1×10$^5$ cells per well. The cells (APC) were cultured together with either a core histone peptide or a control peptide for 6 hours in HL-1 serum free medium (Bio Whittaker, Maryland). This procedure was followed by the addition to each well of CD4$^+$ T cells from the short-term lines at a concentration of 1×10$^5$ cells per well, and the addition of 0.5 micrograms per milliliter of a mouse monoclonal antibody (mAb) to human CD28. The final volume of the cultures was 200 microliters per well. Cells were co-cultured for 24 hours at 37° C. One-half the volume of supernatant was collected from each well for ELISA analysis of interleukin levels. Fresh medium (100 microliters) was added to cells, and the cells were incubated an additional 48 hours. [$^3$H] thymidine was added, and the cultures were incubated an additional 18 hours. Incorporated radioactivity was measured to quantitate T cell proliferation as described previously (Desai-Mehta et al., 1995, J. Clin. Invest. 95:53 1–541). HLA class II dependence of antigen-specific responses by the CD4$^+$ T cells was determined by adding to the co-cultures a blocking antibody from a panel of mAb to HLA class II molecules, as described previously (Desai-Mehta et al., 1995, J. Clin. Invest. 95:53 1–541).

The autoantibody-inducing T cell clone, DD2, from a patient with SLE-associated nephritis was previously reported (Rajagopalan et al., 1990, Proc. Natl. Acad. Sci. 87:7020–7024; Desai-Mehta et al., 1995, J. Clin. Invest. 95:53 1–541). DD2 was stimulated as described above with autologous EBV-B cell lines which had been pre-pulsed with the histone peptides.

IL-2 Production Analysis

IL-2 secreted by CD4$^+$ T cells in short term experiments was measured using an ELISA. Capture and biotinylated antibody pairs directed at human IL-2 and standards for use therein were purchased from PharMingen. ELISAs were performed in 96-well Nunc-Immunoplate (Maxisorb™, Nunc, Denmark). Streptavidin-conjugated horseradish peroxidase and the substrate 3, 3', 5, 5'-tetramethyl benzidine dihydrochloride were purchased from Sigma Chemical Co. (St. Louis, Mo.). ELISAs were performed according to the protocol provided by manufacturer.

Direct Stimulation of PBMCs

Measurement of antigen-specific, intracellular cytokine responses of T cells were performed as described with slight modifications (Waldrop et al., 1997, J. Clin. Invest. 99:1739–1750; Openshaw et al., 1995, J. Exp. Med 182:1357–1367; Estcourt et al., 1997, Clin. Immunol. Immunopathol. 83:60–67). Purified, PBMCs were placed in 12×75 millimeter polystyrene tissue culture tubes (Becton Dickinson, Lincoln Park, N.J.) at a concentration of 1×10$^6$ cells per tube. A solution comprising 0.5 milliliters of HL-1 serum free medium, 100 units per milliliter of penicillin, 100 units per milliliter streptomycin, 2 millimolar L glutamine (Gibco BRL), varying amounts of individual histone peptides, and 1 unit of anti-CD28 mAb (Becton-Dickinson, Lincoln Park, N.J.) was added to each tube. Anti-CD3 mAb was added to a duplicate set of normal PBMC cultures as positive control. Culture tubes were incubated for 1 hour. Brefeldin A was added to individual tubes at a concentration of 1 microgram per milliliter, and the tubes were incubated for an additional 17 hours.

Flow Cytometry Analysis

The assays were performed as described previously (Waldrop et al., 1997, J. Clin. Invest. 99:1739–1750; Openshaw et al., 1995, J. Exp. Med 182:1357–1367; Estcourt et al., 1997, Clin. Immunol. Immunopathol. 83:60–67). PBMCs stimulated as described above were harvested by washing the cells twice with a solution comprising Dulbecco's phosphate-buffered saline (dPBS) and 10 units of Brefeldin A. These washed cells were fixed by incubation for 10 minutes in a solution comprising 0.5 milliliters of 4% paraformaldehyde and dPBS. The cells were washed with a solution comprising dPBS and 2% fetal calf serum (FCS). The cells were then either used immediately for intracellular cytokine and surface marker staining or were frozen for no more than three days in freezing medium, as described (Waldrop et al., 1997, J. Clin. Invest. 99:1739–1750).

For intracellular cytokine staining, the cell preparations were rapidly thawed in a 37° C. water bath and washed once with dPBS. Cells, either fresh or frozen, were resuspended in 0.5 milliliters of permeabilizing solution (Becton Dickinson Immunocytometry systems, San Jose, Calif.) and incubated for 10 minutes at room temperature with protection from light. Permeabilized cells were washed twice with dPBS and incubated with directly conjugated mAbs for 20 minutes at room temperature with protection from light. Optimal concentrations of antibodies were predetermined according to standard methods. After staining, the cells were washed, refixed by incubation in a solution comprising dPBS 1% paraformaldehyde, and stored away from light at 4° C. for flow cytometry analysis.

Five parameter flow cytometry analyses were performed with a FACSCalibur (Becton Dickinson Immunocytometry systems, San Jose, Calif.) using FITC, phycoerythrin (PE), and peridinin chlorophyl protein (PerCP) as the fluorescence parameters. Methods of cytometer set up and data acquisition have been described previously (Shivakumar et al., 1989, J Immunol.143:103–112; Desai-Mehta et al., 1996, J. Clin. Invest. 97:2063–2073; Waldrop et al., 1997, J. Clin. Invest. 99:1739–1750; Openshaw et al., 1995, J. Exp. Med 182:1357–1367; Estcourt et al., 1997, Clin. Immunol. Immunopathol. 83:60–67). For analysis of each cytokine response against each of the histone peptides, the cytometer was gated on CD4 expression and 10,000 events were acquired per analysis. A light scatter gate was also used to identify nonviable lymphocytes (Shivakumar et al., 1989, J Immunol.143:103–112; Desai-Mehta et al., 1996, J. Clin. Invest. 97:2063–2073; Waldrop et al., 1997, J. Clin. Invest. 99:1739–1750). Isotype-matched negative control reagents were used to verify the staining specificity of experimental antibodies and as a guide for setting markers to delineate "positive" and "negative" populations.

The results of the experiments presented in this Example are now described.

Response of an Anti-DNA Autoantibody-Inducing, Lupus Th Cell Clone To Histone Peptides To localize histone peptide epitopes for autoimmune T cells of human SLE, the response of CD4$^+$T cell clone DD2, was characterized. DD2 has previously been shown to induce the production of the pathogenic variety of anti-DNA autoantibodies when co-cultured with autologous B cells. In addition, clone DD2 recognizes nucleosomes, particularly its core histone, H4. (Desai-Mehta et al., 1995, J. Clin. Invest. 95:531–541). In the present Example, the DD2 clone was tested against the entire panel of nucleosomal histone peptides.

As illustrated in FIG. 12, DD2 can be stimulated by a group of histone H4 peptides located between amino acid positions 67 and 99. The other nucleosomal histone peptides did not stimulate DD2, except for one peptide, H3$_{55-69}$, which stimulated DD2 very weakly. These results were consistent with previously published autoantigenic-specificity of DD2 tested with whole autoantigens (Desai-Mehta et al., 1995, J. Clin. Invest. 95:53 1–541).

Figure 13B:
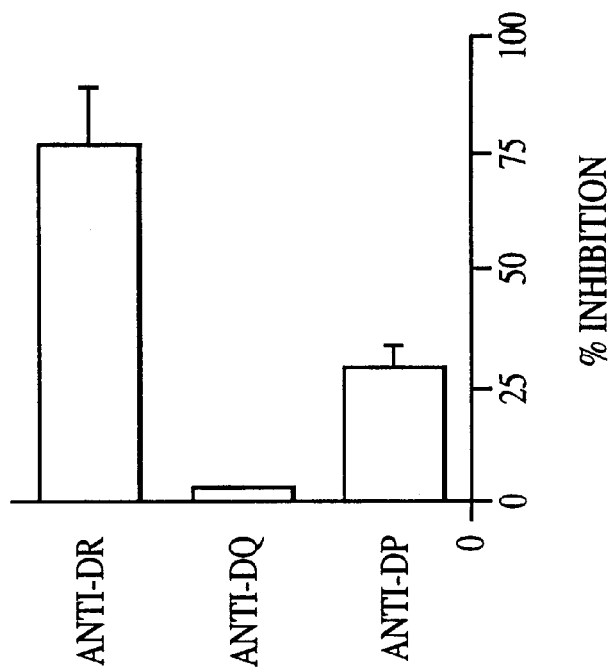
FIGS. 13A and 13B, is a pair of graphs depicting the response of SLE-associated T cells to histone peptides.
Figure 13A:
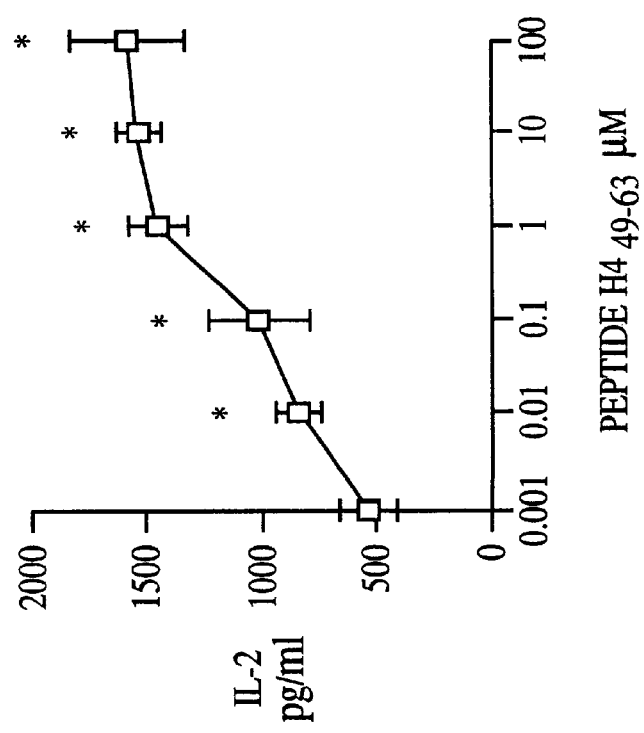
Figure 14A:
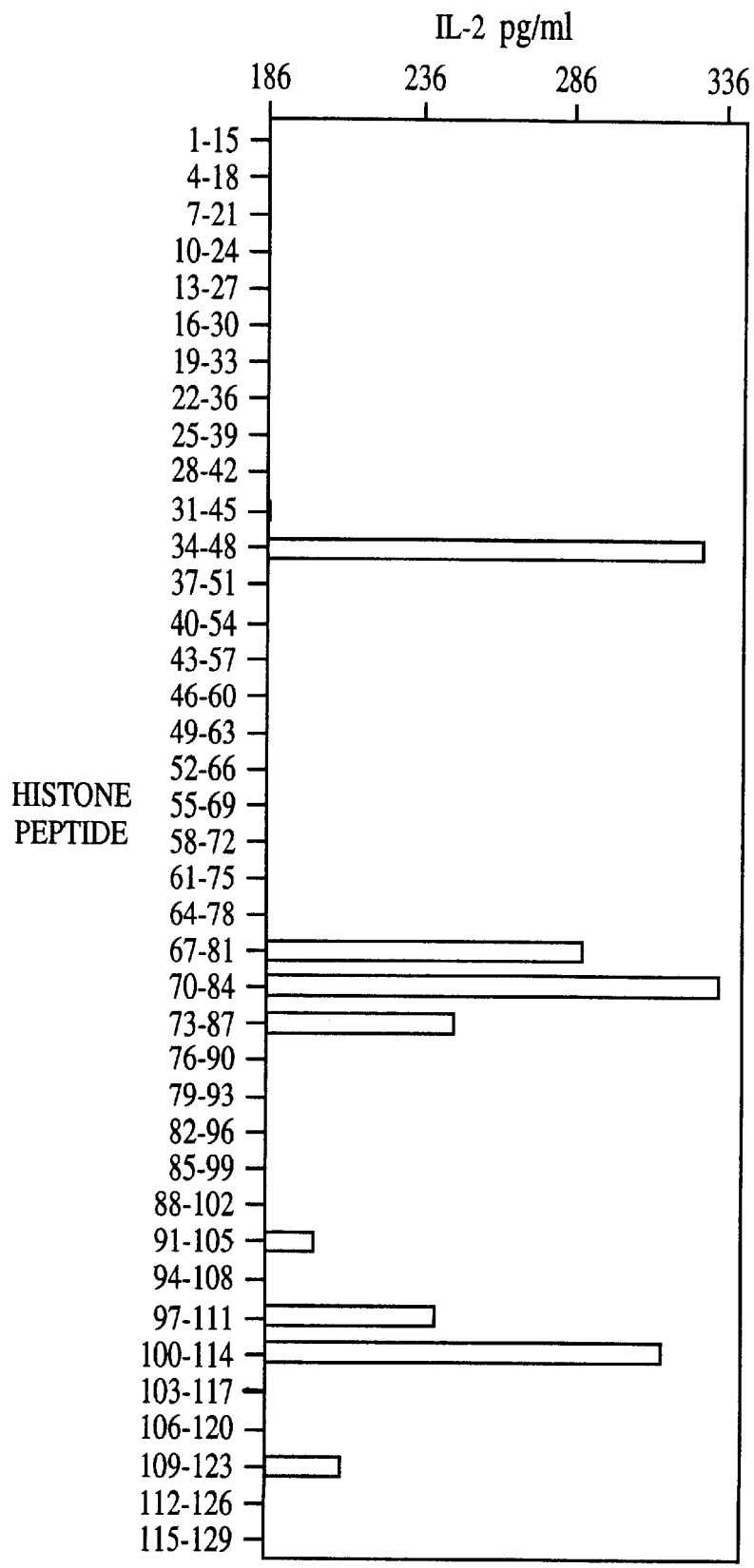
FIGS. 14A–14D, is a series of graphs which illustrate the results of a pepscan. These experiments measure IL-2 production by an SLE-associated, short-term, CD4$^+$ T cell line, L-SC, in response to histone peptides presented by APCs. The baseline value for the y-axis is set at 3 standard deviations (SD) above the mean of background values of IL-2 in picograms per milliliter of culture medium produced by T cells cultured with APC alone. Only IL-2 production responses to peptides above this 3 SD value are shown. Peptides corresponding to H2A histone protein are shown in FIG. 14A. Peptides corresponding to H2B histone protein are shown in FIG. 14B. Peptides corresponding to H3 histone protein are shown in FIG. 14C. Peptides corresponding to H4 histone protein are shown in FIG. 14D.
Figure 14B:
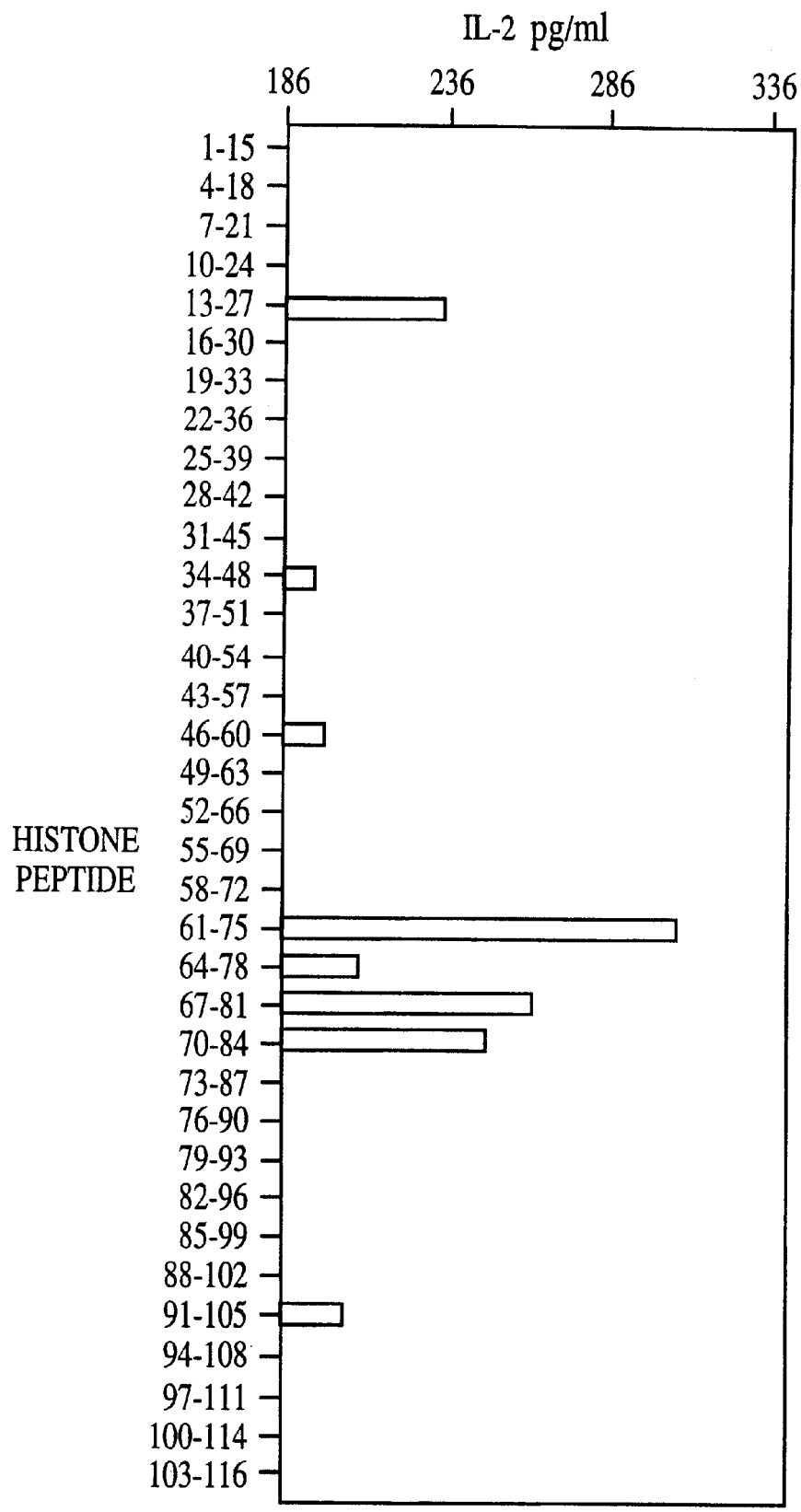
Figure 14C:
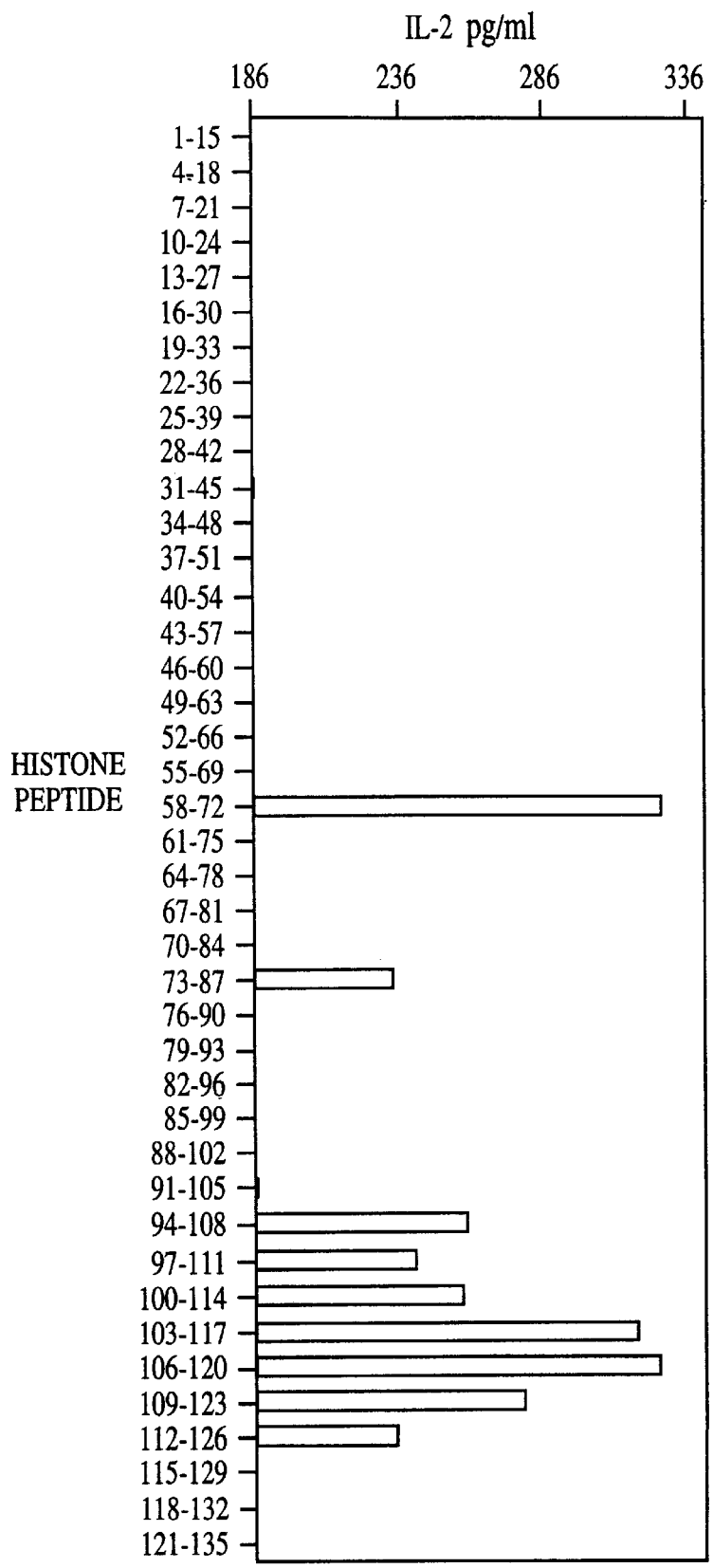
Figure 14D:
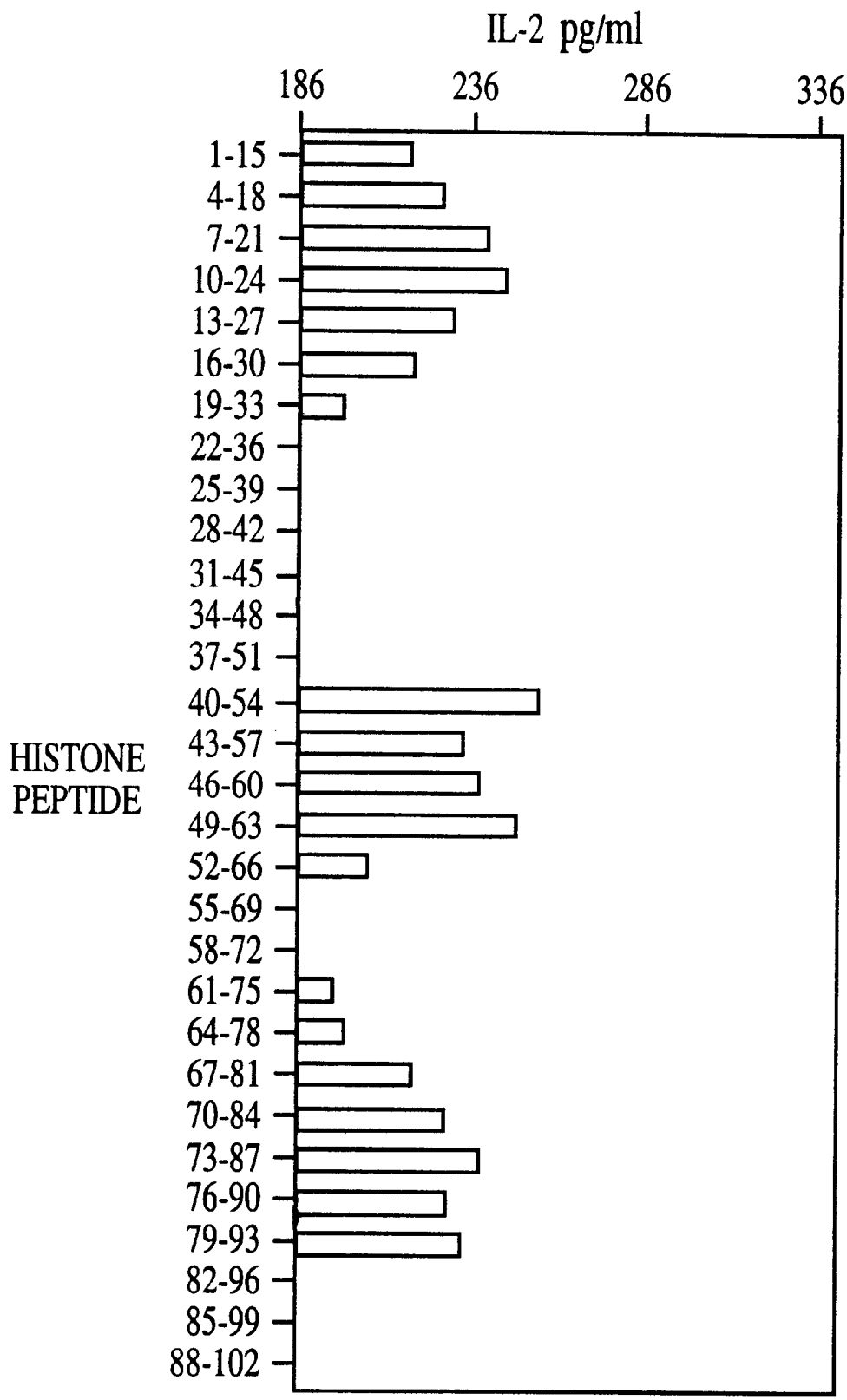
Figure 15A:
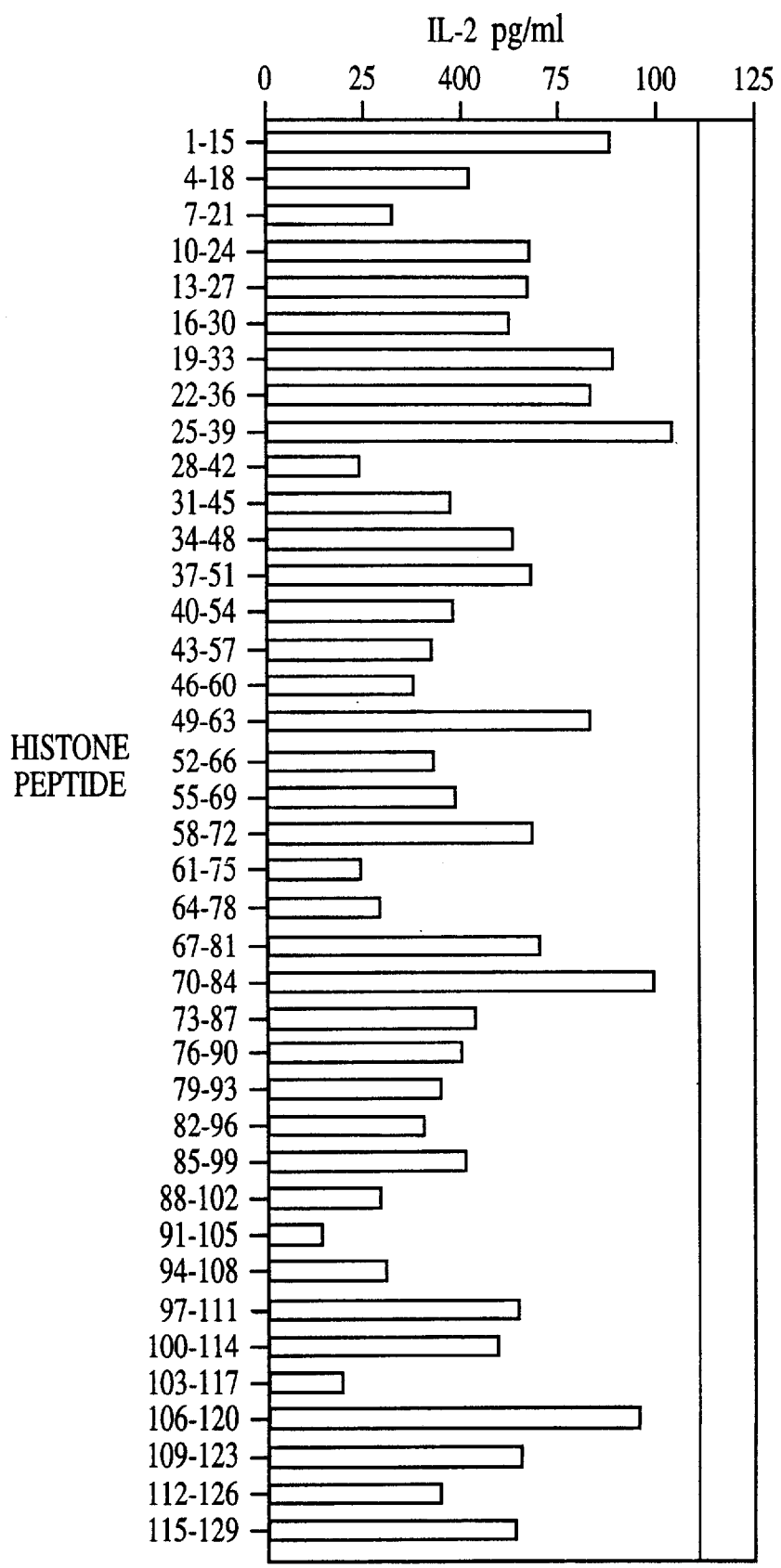
FIGS. 15A–15D, is a series of graphs depicting the results of a pepscan. This experiment measures IL-2 production by a short-term CD4$^+$ T cell line from a normal subject (N-JV) in response to histone peptides using autologous EBV-B cells obtained from the same subject as APCs. The horizontal line in each panel demarcates 3 SD above the mean of background values. Peptides corresponding to H2A histone protein are shown in FIG. 15A. Peptides corresponding to H2B histone protein are shown in FIG. 15B. Peptides corresponding to H3 histone protein are shown in FIG. 15C. Peptides corresponding to H4 histone protein are shown in FIG. 15D.
Figure 15B:
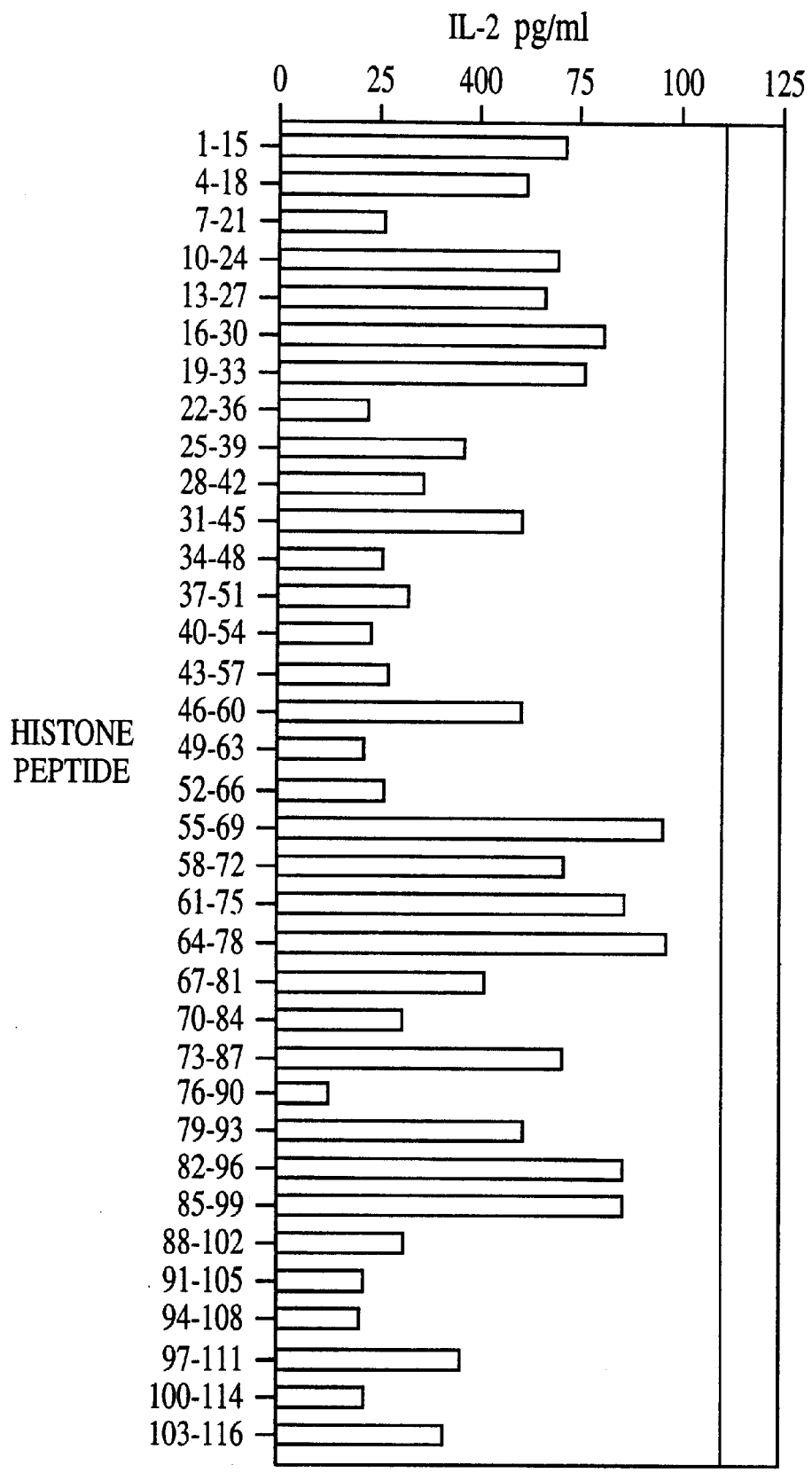
Figure 15C:
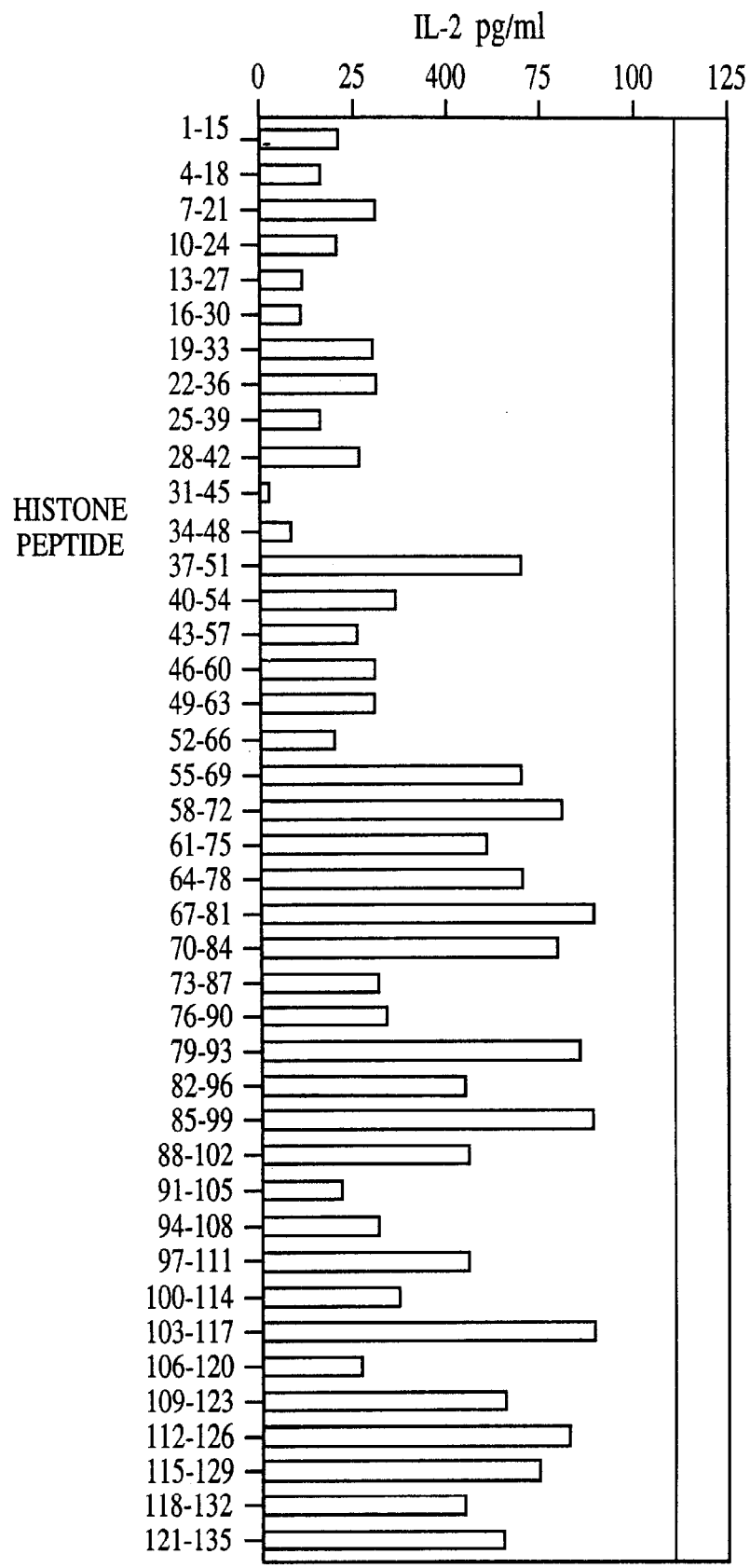
Figure 15D:
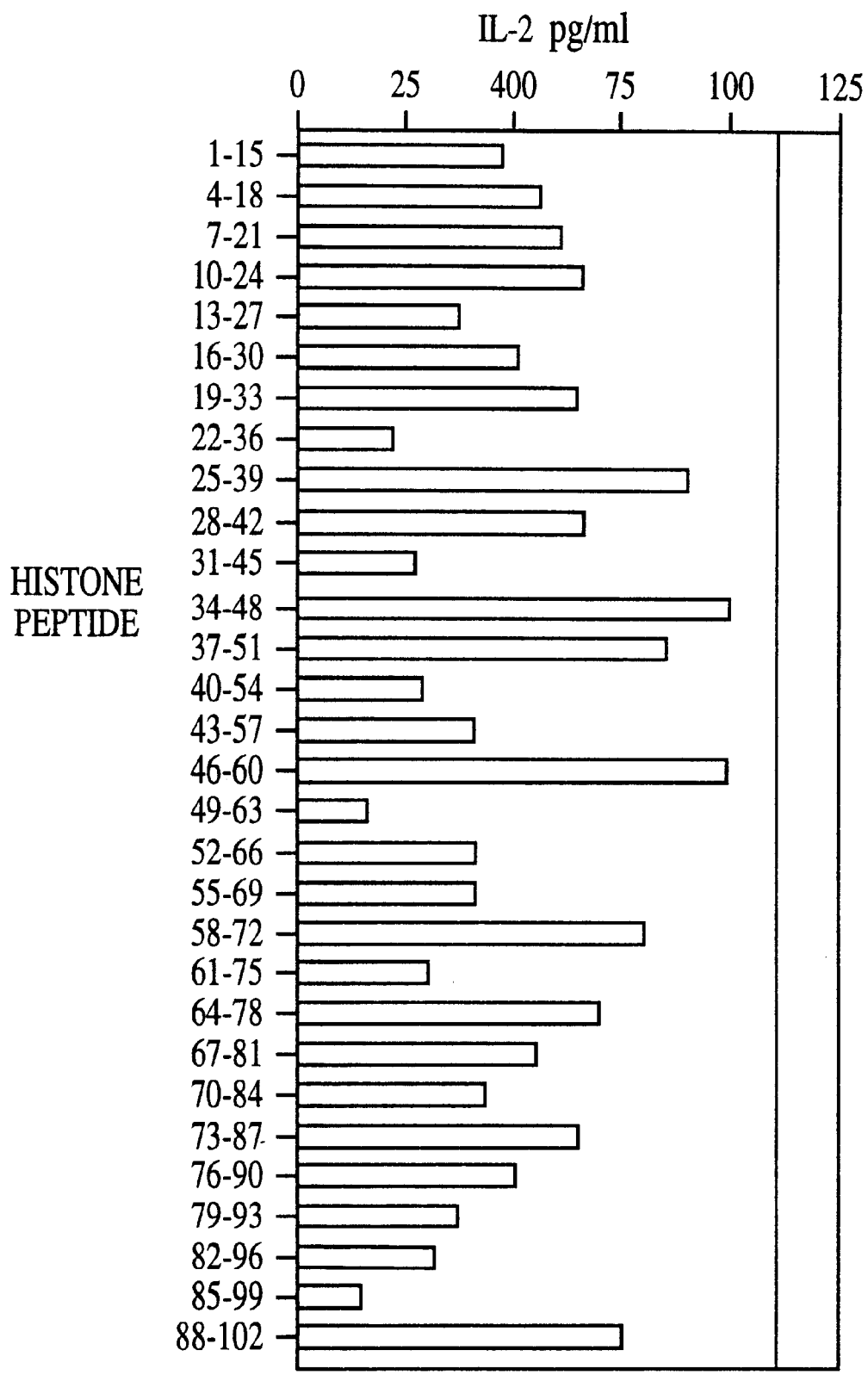
Figure 16A:
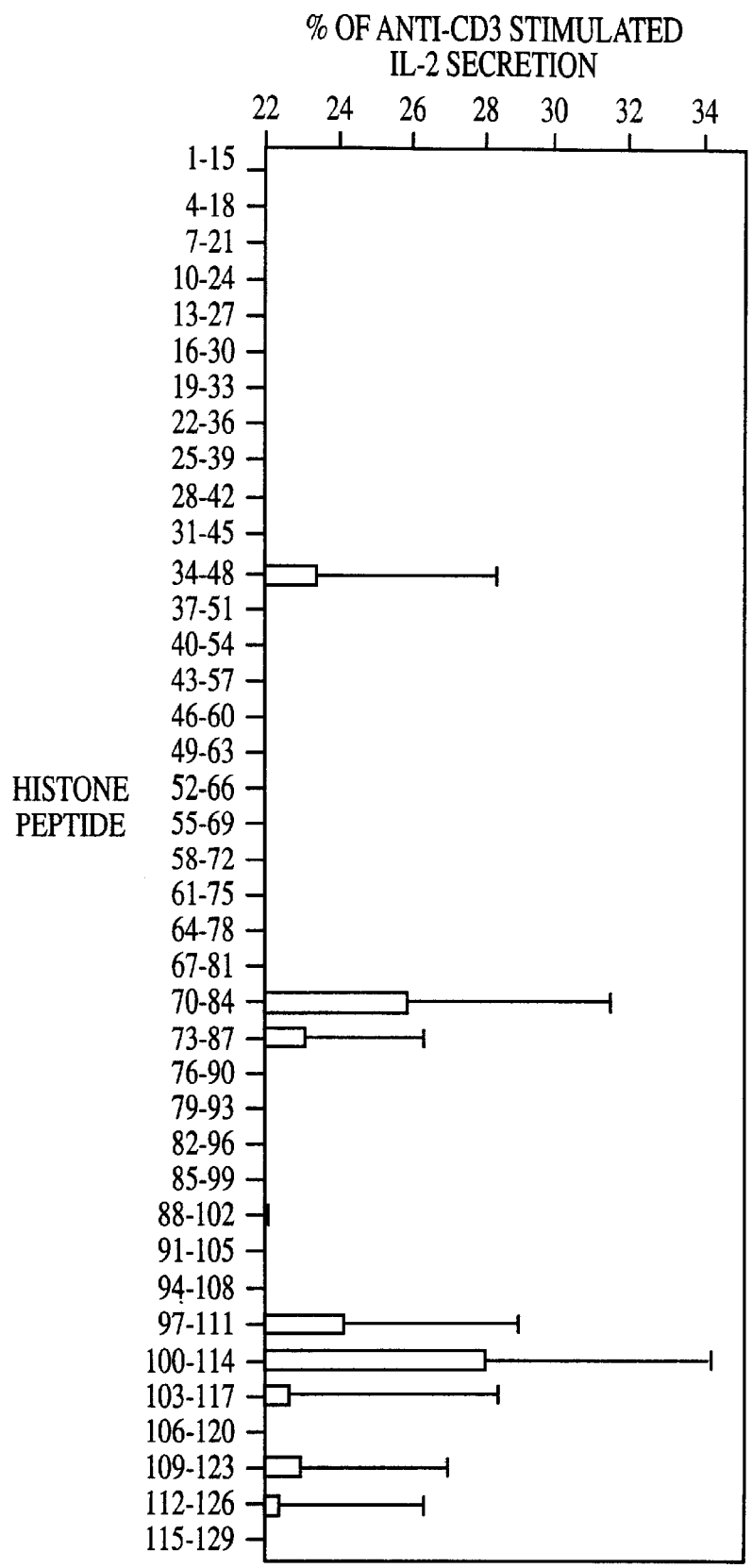
FIGS. 16A–16D, depicts the collective data of IL-2 production responses of short-term T cell lines to nucleosomal peptides in 10 patients with lupus. The results are expressed as a percentages of "maximal" responses of the respective T cell lines stimulated by anti-CD3 mAb±the standard error of the mean. Bars represent mean values from the ten lupus T cell lines, with error bars in one SEM. Values of T cells cultured with autologous EBV B-cell APCs were considered as background. The baseline for the y-axis is set at 22% which is 3 SD above the mean of background values (14.5%). A peptide was considered as stimulatory when it elicited a positive response above this baseline. For instance, the average of responses of all 10 T cell lines to H4$_{16-30}$ peptide was 23±2.6. All the stimulatory peptides shown elicited positive responses in all 10 lupus T cell lines to levels greater than 3 SD above their respective background values. Peptides corresponding to H2A histone protein are shown in FIG. 16A. Peptides corresponding to H2B histone protein are shown in FIG. 16B. Peptides corresponding to H3 histone protein are shown in FIG. 16C. Peptides corresponding to H4 histone protein are shown in FIG. 16D.
Figure 16B:
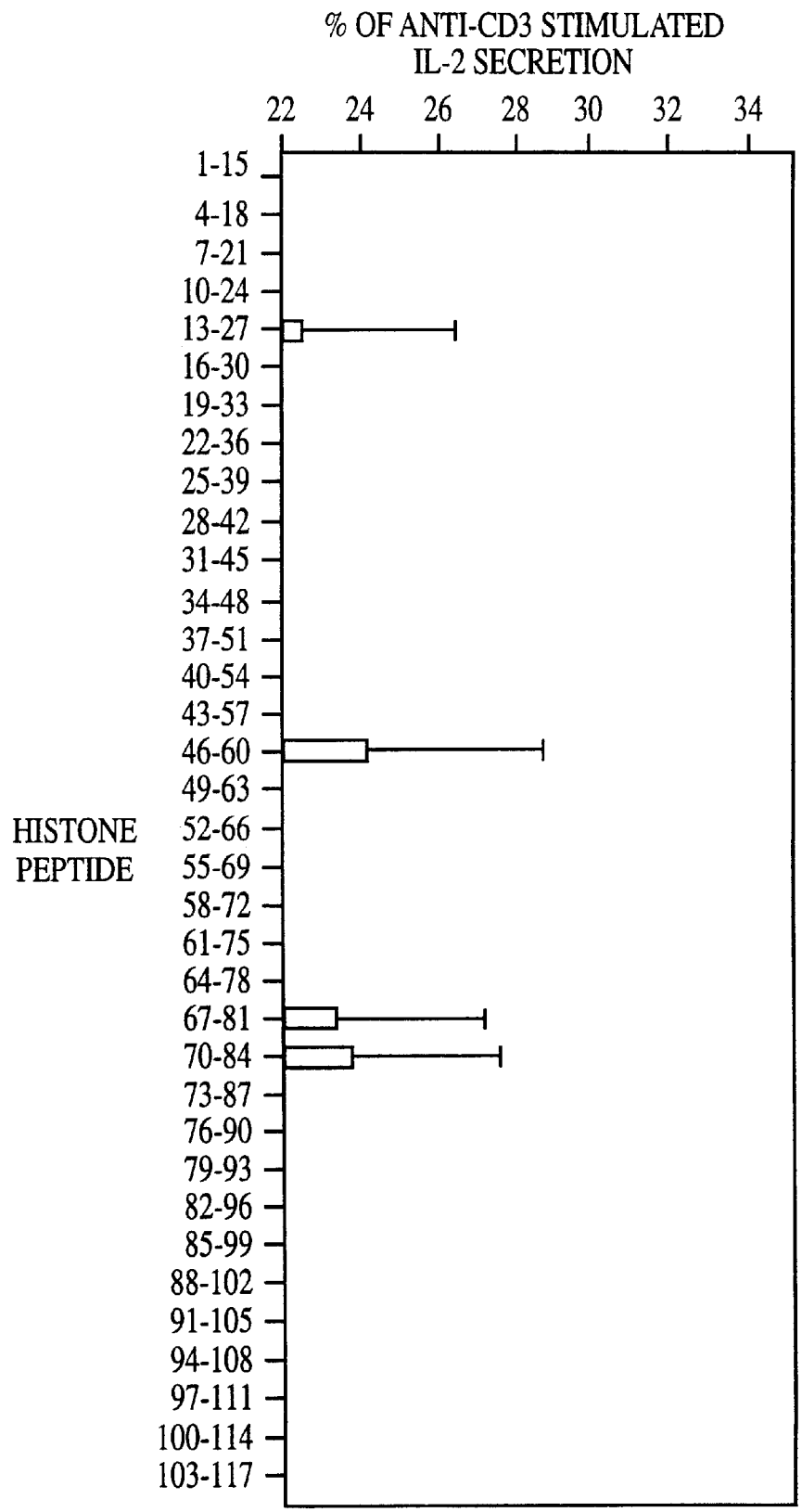
Figure 16C:
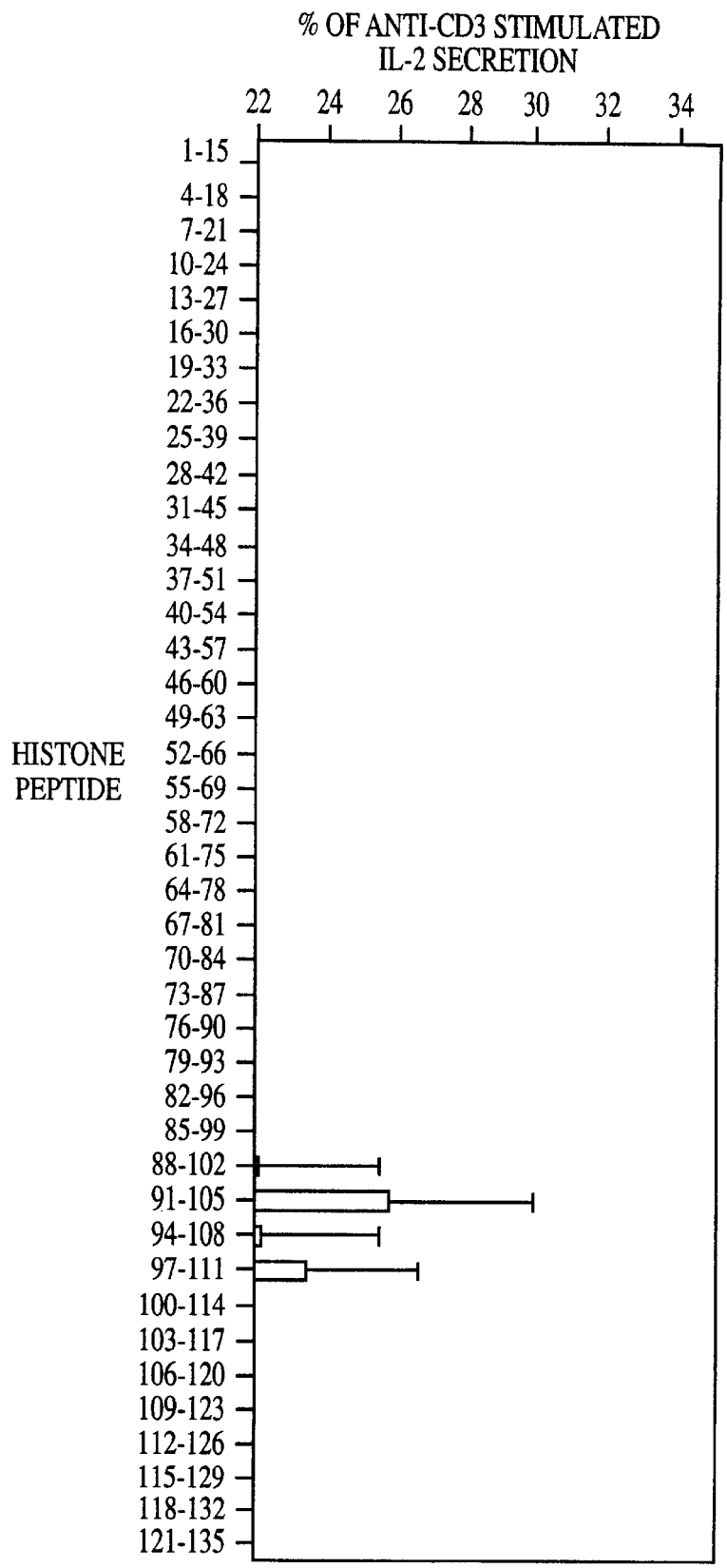
Figure 16D:
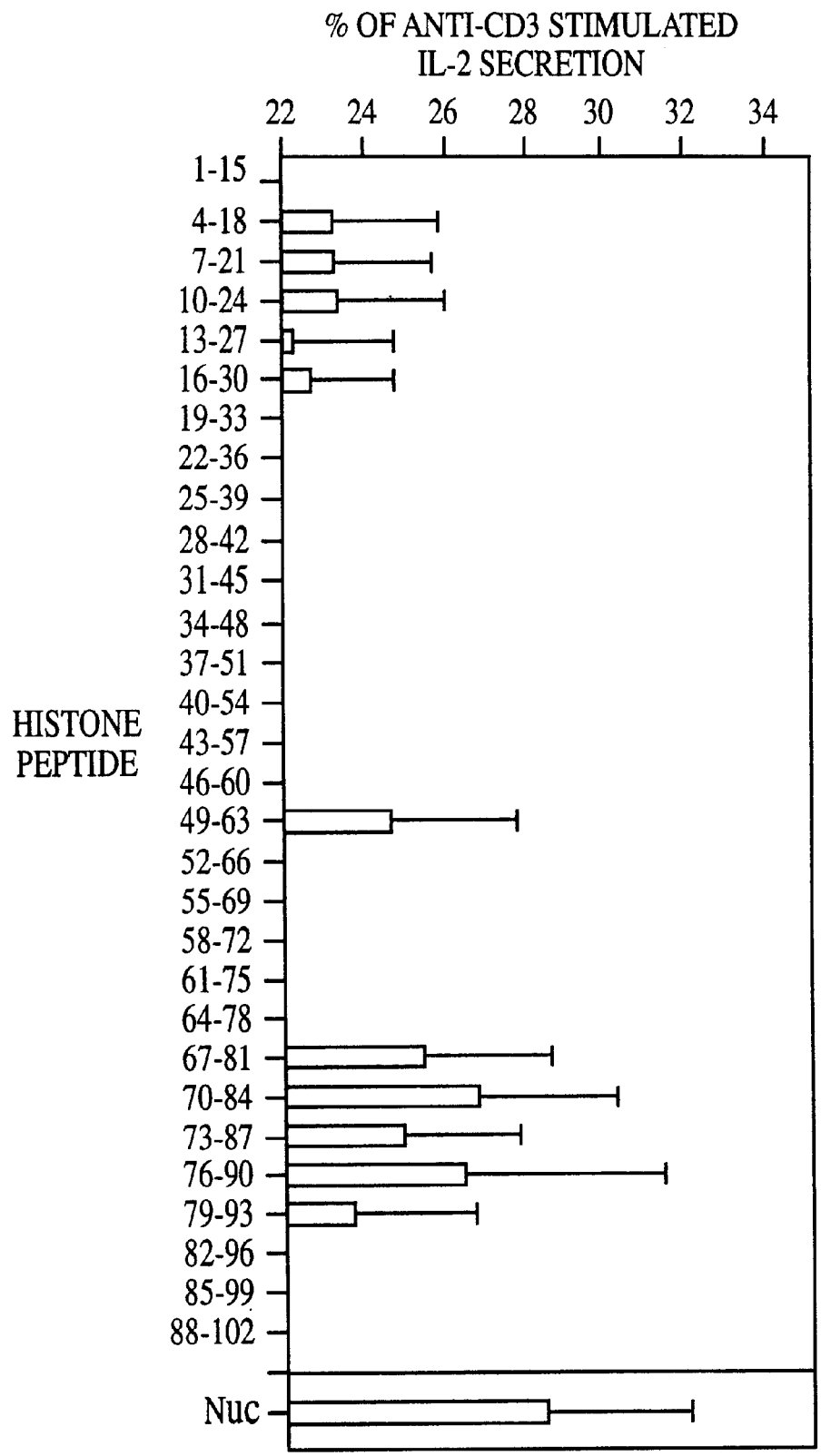

Localization Of Major Peptide Epitopes For Autoimmune T Cells by Using Short-Term, CD4+Cell Lines Derived from Lupus Patients To narrow down the regions in nucleosomal core histones that would contain the major peptide autoepitopes, short-term CD4$^+$ T lines derived from both lupus patients and healthy donors were incubated as described above, and were tested for their response to the histone peptides. Autologous EBV-B cell lines were included with these T cells as APCs. Dose response curves were determined after identifying stimulatory histone peptides (i.e. which comprise autoepitope regions) for the respective T cell lines. A representative example of a dose response is shown in FIG. 13A. Based on these studies 10 micromolar peptide concentrations were used in further experiments.

Four of the short-term lupus T cell lines were also tested for HLA-class II dependence for antigen recognition, and were found to recognize their respective peptide epitopes presented by HLA-DR molecules. A representative example is shown in FIG. 13B. These results with histone peptides are consistent with previous observations using whole nucleosomes (Desai-Mehta et al., 1995, J. Clin. Invest. 95:53 1–541).

Altogether, 10 short-term CD4+ T cell lines derived from lupus patients and 6 healthy donor T cell lines were co-cultured with synthetic peptides spanning all of the core histone proteins and autologous EBV-B cell lines. IL-2 produced by these co-cultured cells was measured. The response by a representative short-term T cell line L-SC, derived from a lupus patient, is shown in FIG. 14, and the response by short term T cell line N-JV, derived from a normal control donor, is shown in FIG. 15. All of the short-term T cell lines from normal donors exhibited very weak and insignificant responses to the synthetic histone peptides similar to those shown in FIG. 15. By contrast, the lupus T cell lines, which were also polyclonal, responded strongly to peptides corresponding to certain regions in the core histones as exemplified in FIG. 14.

Collective data of significant responses by all the short-term T cell lines derived from the ten SLE patients is shown in FIG. 16. These pepscan results localize major regions in the core histone proteins that contain autoepitopes recognized consistently and recurrently by the autoimmune T cells from different patients (i.e. SLE-associated autoepitopes). There were no discernible differences between the responses of T cell lines derived from patients with active lupus and those derived from patients in remission. Results of proliferative responses of the T cells to the nucleosomal peptides were consistent with their IL-2 production.

Based on the consensus stimulatory autoepitope regions identified by using the lupus T cell lines and clone DD2 (FIGS. 12–16), a group of 16 peptides, each comprising 15 amino acids, were selected for further testing with T cells in PBMCs from lupus patients and normal subjects. These SLE-associated autoepitope peptide sequences are listed in FIG. 17. In addition, histone peptides comprising 24 amino acids each and overlapping some of the amino acid autoepitopes were also used, and were found to be relevant to SLE-associated Th cells and B cells.

Histone Peptide Epitopes for CD4+ T Cells in PBMC of Lupus Patients

It was necessary to confirm that the histone peptide autoepitopes were also relevant to unmanipulated CD4+ T cells derived from PBMCs of SLE patients. Although the T cell lines used were short-term and not biased by any deliberate addition of histone peptides, they might still be able to undergo activation-induced cell death and selective expansion in vitro. In addition, to determine the frequency of CD4+ T cell response to a particular peptide epitope, it was found that using flow cytometry for the identification of newly synthesized, intracellular cytokines was ideal in rapidly detecting antigen-specific responses (Waldrop et al., 1997, J. Clin. Invest. 99:1739–1750; Openshaw et al., 1995, J. Exp. Med 182:1357–1367; Estcourt et al., 1997, Clin. Immunol. Immunopathol. 83:60–67).

Since a proportion of the autoimmune T cells involved in SLE are already activated in vivo, particularly in patients with active SLE, a measure of antigen-specific induction of T-cell activation markers, such as CD69, CD25 or CD79, is not suitable because of the high background levels which are generated. The intracellular cytokine assay measures only newly synthesized cytokines in response to antigen-specific stimulation, and the secretion of these cytokines is blocked by BFA. Any cytokines made by preactivated T cells are not detectable because they are secreted when BFA is not present in the cultures. Thus, nucleosomal peptide-specific responses of the autoimmune memory T cells of lupus that were not already pre-activated in vivo were measured by this assay. This assay was optimized by providing costimulatory signal via CD28, which did not cause any non-specific background stimulation as described previously (Waldrop et al., 1997, J. Clin. Invest. 99:1739–1750). Moreover, this multiparameter flow-cytometry method could be applied directly to PBMC without T cell purification.

According to the results using lupus patient T-cell lines and clone DD2 (FIGS. 12–16), the stimulatory histone peptide epitopes could be localized to include several regions of nucleosomal histone proteins. Interestingly, these histone autoepitopes which stimulate autoimmune T cells overlapped with the nephritis-inducing autoepitopes which were identified for pathogenic autoantibody-inducing Th cells of lupus-prone mice in the experiments of Example 1. Therefore, in addition to the sixteen histone peptides listed in FIG. 17, and the three longer histone peptides $H2B_{10-33}$, $H4_{16-39}$, and $H4_{71-94}$, that were also found to be disease-relevant for pathogenic T and B cells of lupus mice (Kaliyaperumal et al., 1996, J. Exp. Med 183:2459–2469) were tested again with the PBMC. As an additional background control, the $H3_{83-97}$ peptide was used, which, although it is partly within a stimulatory region in H3, it was not recognized by any of the T-cell lines or clone DD2.

Intracellular production of newly synthesized cytokines, IFN-γ, IL-2, IL-10 and IL-4, was assayed. The assay results are depicted in FIG. 18, wherein two representative cytokine staining profiles from patients R-WG and R-SC are shown. Cells which stained positive for a particular cytokine formed a discreet population; single cells producing more than one cytokine were rare in fresh PBMCs.

Figure 19A-6:
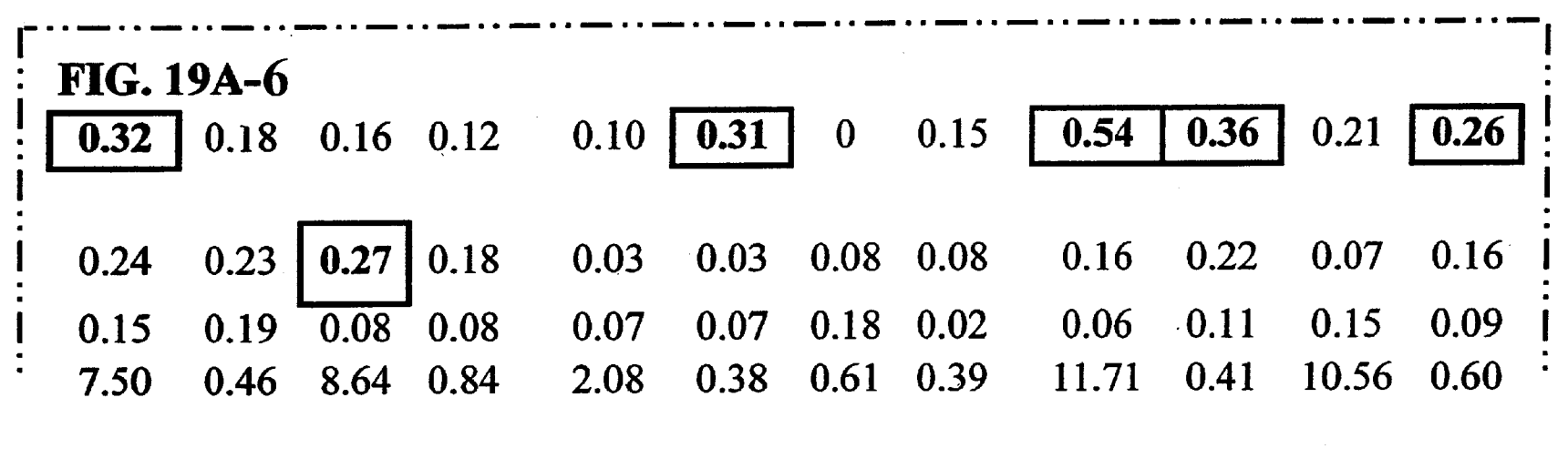
Figure 20:
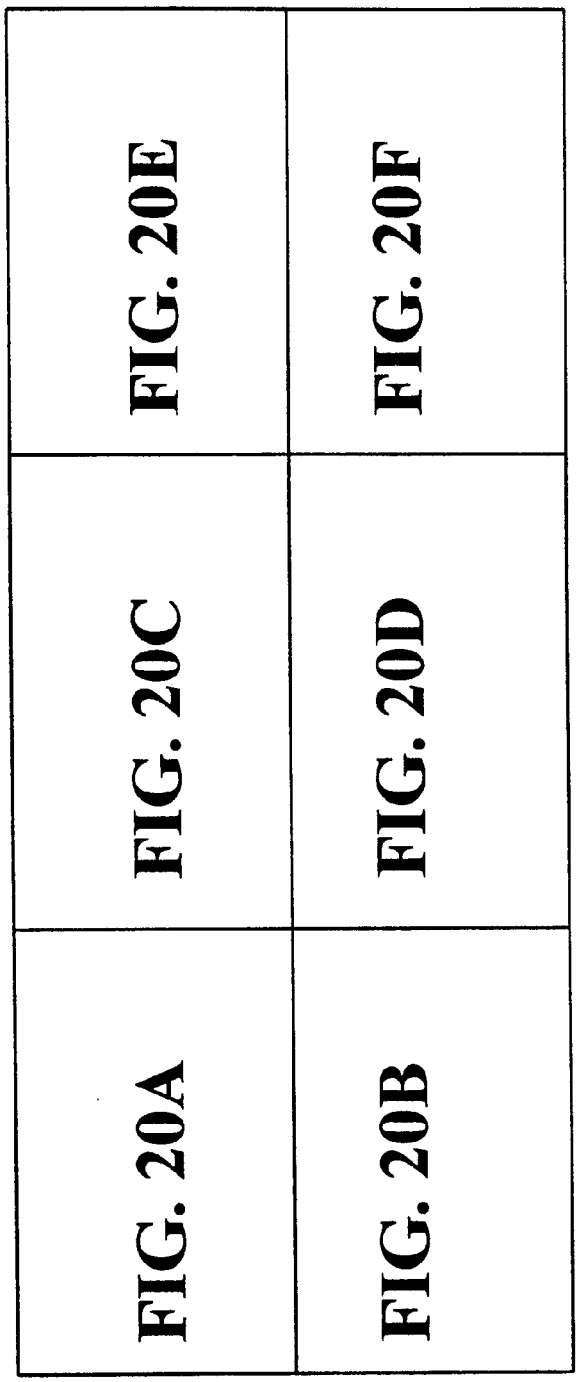
FIG. 20 is a table which lists the data from flow cytometry analysis of intracellular cytokine staining of $CD4^+$ T cells obtained from seven normal subjects. A positive response is indicated by outlined and bold numbers.

The results of assays for intracellular cytokine production by CD4+ T cells from 12 SLE patients are shown in FIG. 19. Eight patients in remission and 4 patients with active disease, designated by prefixes, R-and A-respectively, were studied. In FIG. 20, the corresponding results from 7 normal (designated N-) control subjects are depicted. The total number of CD4+ T cells in normal subjects was comparable to the total number in lupus patients in remission. In consideration of previous studies (Waldrop et al., 1997, J. Clin. Invest. 99:1739–1750; Openshaw et al., 1995, J. Exp. Med 182:1357–1367; Estcourt et al., 1997, Clin. Immunol. Immunopathol. 83:60–67), a response to a nucleosomal peptide is considered to be unequivocally positive when the frequency of positive cells was greater than 0.2% and the values were at least 2-fold higher than respective background values (i.e. cultures without peptide, designated "medium" in FIGS. 19 and 20). Repeat assays with aliquots of cells from the same sample generated almost identical results (i.e. SD of less than 5%).

Some of the nucleosomal peptides caused impressive stimulation of T cells obtained from SLE patients. In contrast, positive responses were rare in the normal subjects. IFN-γ and IL-4 production levels in response to nucleosomes or histone peptides were greater than 10 fold above background values, and corresponding IL-10 production levels were up to 20 fold higher in some of the SLE patients.

These results are highly significant, because the frequency of autoepitope-specific CD4+ T cells (i.e. positive responders) was measured in this assay (Waldrop et al., 1997, J. Clin. Invest. 99:1739–1750). Remarkably, the ability to respond to the histone peptides was still present in the patients in long-term remission, indicating that one or more genetically programmed defects may be involved. In fact, the anti-CD3 response and responses to SLE-associated autoepitopes as a whole were considerably attenuated in the PBMCs of some of the patients with active lupus (A-KJ and A-WB), possibly due to prior autoantigen-driven activation in vivo and exhaustion or desensitization. Remarkably, IL-10 production responses to certain nucleosomal peptides were, in many cases, higher than corresponding anti-CD3 responses, even in the patients in remission. In some patients, responses to certain histone peptides were stronger than to the whole nucleosome particle.

FIG. 21 provides a summary of the percentage of positive responders to selected histone peptides among the SLE patients. Although, some cytokine responses exhibited spreading to many different histone peptide autoepitopes in a patient, such as R-DS, R-JE, and A-MG, certain histone peptides turned out to be recurrent autoepitopes for the autoimmune T cells of most of the SLE patients tested. Among these SLE patients, the incidence of positive responders ranged from 50 to 100% to the following autoepitopes: whole nucleosomes, $H2B_{10-33}$, $H4_{16-39}$, $H4_{71-94}$, $H2A_{34-48}$, $H3_{91-105}$, $H3_{100-114}$, $H4_{14-28}$, and $H4_{49-63}$.

Remarkably, the recurrent autoepitopes identified here for the T cells involved in SLE, namely $H2B_{10-33}$, $H3_{95-105}$, $H4_{16-39}$, and $H4_{71-94}$, are also the major autoepitopes for nephritis-inducing T cells in lupus-prone $SNF_1$ mice (Kaliyaperumal et al., 1996, J. Exp. Med 183:2459–2469).

In the case of patients in remission in which the T cells have a phenotype comparable to normal subjects, the preferential IL-10 stimulation by some peptides over anti-CD3 in some of the patients would suggest nucleosomal autoepitope-specific modulation of cytokine production. The importance of IL-10 and other Th2 cytokines in the pathogenesis of SLE has also been well documented, but its mechanism is not known (Ishida et al., 1994, J. Exp. Med 179:305–310; Llorente et al., 1995, J. Exp. Med 18 1:839–844; Nakajima et al., 1997, J. Immunol. 158:1466–1472). Thus, SLE is not a straightforward TH1 or Th2 type disease.

The value of autoepitope mapping for the pathogenic T cells in autoimmune diseases cannot be overemphasized. The T cell receptor (TCR) repertoire of the pathogenic Th cells involved in SLE is heterogeneous, and the autoepitopes they recognize become diverse with "epitope-spreading" as the disease progresses (Craft, J., and Fatenejad, May 1997). Arthritis. Rheum. 40:1374–1382). Individual TCRs of the pathogenic autoantibody-inducing Th cells of lupus, recognize more than one histone peptide autoepitope in a promiscuous or degenerate fashion, and in the context of diverse class II molecules (Kaliyaperumal et al., 1996, J. Exp. Med 183:2459–2469; Shi et al., 1998, J. Exp. Med. 187:367–378). Peptide-dominant interactions between the lupus TCRs and MHC-nucleosomal peptide complex due to reciprocally charged residues probably overcomes the requirement for MHC-restriction, but not MHC-dependence (Shi et al., 1998, J. Exp. Med. 187:367–378). Structural motifs for these major T-cell epitopes in the primary, endogenous immunogens of lupus could be used to identify viral or bacterial mimicry peptides that have sufficient structural similarity to initiate the activation and expansion of the pathogenic Th cells of lupus, as described in other autoimmune diseases (Wucherpfennig and Strominger, 1995, Cell. 80:695–705).

Peptides corresponding to the major autoepitopes as described herein could also be used to design peptide-specific immunotherapy. Remarkably, in murine lupus, any one of the major autoepitopes identified herein could diminish pathogenic autoantibody production against multiple lupus antigens (i.e. tolerance spreading), and markedly delay the development of SLE-associated nephritis. A single histone peptide with charged residues could potentially tolerize a spectrum of Th cells whose promiscuous TCRs could recognize one or two shared residues in multiple, different peptide autoepitopes (Kaliyaperumal et al., 1996, J. Exp. Med 183:2459–2469; Shi et al., 1998, J. Exp. Med. 187:367–378). Importantly, the results described herein demonstrate that the autoepitopes involved in SLE in mice are also involved in human SLE. Moreover, the pathogenic Th cells of lupus are multipotent or promiscuous in their helper activity. According to the model of SLE-associated autoantibody production illustrated in FIG. 11, a single lupus Th clone can help either a dsDNA-specific, a ssDNA-specific, a histone-specific, an HMG specific, or a nucleosome-specific B cell because each of these B cells, by binding to its respective epitope on the whole chromatin, can take it up, process and present the relevant peptide epitope in the chromatin to the Th clone (Desai-Mehta et al., 1995, J. Clin. Invest. 95:53 1–541; Mohan et al., 1993, J. Exp. Med. 177:1367–1381) resulting in intermolecular help. Tolerization of such Th cells would obviously deprive multiple autoimmune B cells of T-cell help. Furthermore, the SLE-associated autoepitopes of autoimmune T cells fall within the regions of the histone proteins that are also targeted by SLE-associated autoantibodies (Stemmer et al., 1997, J. Mol. Biol. 273:52–60; Monestier and Kotzin, 1992, Rheum. Dis. Clin. N. Am. 18:415–436; Stemmer et al., 1996, .J. Biol. Chem. 271:21257–21261). Indeed, the overlapping of epitopes for autoimmune Th cells and autoimmune B cells of lupus makes $H4_{16-39}$ a highly efficient tolerogen for therapy of murine lupus nephritis, as shown in Example 1. Moreover, the nucleosomal autoepitopes for human lupus T-cells have multiple MHC II, DR binding motifs (FIG. 22), suggesting that they could be used widely for tolerogenic therapy despite the diversity of lupus patients' HLA-DR alleles.

The recognition of nucleosomal autoepitopes by the pathogenic T cells of murine lupus is MHC-dependent but unrestricted (Shi et al., 1998, J. Exp. Med. 187:367–378), and so far, susceptibility to lupus nephritis has not been linked to genes for any particular MHC molecule. Non-MHC genes within the MHC locus, such as, gene for TNF, or the C4A null allele, are probably directly responsible for lupus susceptibility (Vyse and Kotzin, 1998, Annu. Rev. Immunol. 16:261–292; Morel and Wakeland, 1998, Current Opin. Immunol. 10:718–725). Thus, identification of major nucleosomal peptide autoepitopes for the T cells of human lupus might be important for understanding how such autoimmune T cells arise, for tracking such T cells using peptide-MHC tetramers, and for developing antigen-specific therapy.

The experiments of this Example identify nucleosomal histone peptides corresponding to histone regions, $H2B_{10-33}$, $H4_{16-39}$ $H4_{14-28}$, $H4_{71-94}$, $H3_{91-105}$, and $H3_{100-114}$, which were recurrently recognized by CD4+ T cells from the majority of lupus patients regardless of disease stage. These same peptides are also the major epitopes for the Th cells that induce anti-DNA autoantibodies and subsequent nephritis in lupus-prone mice. Two other recurrent epitopes for human SLE-associated T cells have been localized to $H2A_{34-48}$ and $H4_{49-63}$. All the SLE-associated autoepitopes have multiple HLA-DR binding motifs and are located in the histone regions that are targeted by lupus autoantibodies, suggesting a basis for their immunodominance and potential efficacy as tolerogens. These major autoepitopes may reveal the mechanism of autoimmune T cell expansion and lead to antigen-specific therapy of human lupus.

EXAMPLE 3

A Potent SLE-Associated Autoepitope Isolated from Naturally Processed Chromatin Peptides In the experiments presented in this Example, several MHC Class II-associated peptides have been identified and tested for their ability to stimulate anti-DNA autoantibody production by established T helper (Th) cell lines and primary T helper cell isolates. These Th cells are essential for sustaining the pathogenic autoantibody-producing B cells associated with SLE (Datta et al., 1987, J. Exp. Med. 165:1252–1268; Ray et al., 1996, Proc. Natl. Acad Sci. USA. 93:2019–2024; Mohan et al., 1995, J. Immunol. 154:1470–1480).

The materials and methods presented in this Example are now described.

Mice

BALB/c, NZB, SWR, (BALB/c×SWR)$F_1$ mice were purchased from The Jackson Laboratory (Bar Harbor, Me.). Lupus-prone (SWR×NZB)$F_1$ (SNF$_1$) hybrids were bred at the animal facility of Northwestern University. Female mice were used in each of the experiments.

Preparation of Cloned Th Cell Lines and Hybridomas

Cloned Th cell clones and hybridomas used in the experiments presented in this Example were derived from SNF$_1$ mice with lupus nephritis (Adams, et al., 1991, Proc. Natl. Acad. Sci. USA 88:11271–11275; Sainis and Datta, 1988, J. Immunol. 140:2215–2224). The cloned Th cell lines were maintained in co-culture with irradiated SNF$_1$ spleen cells and complete medium comprising RPMI-1640, 20 units per milliliter of rIL-2 (Life Technologies, Inc., Grand Island, N.Y.), 10% heat inactivated FCS, 100 units per milliliter of penicillin, 100 micrograms per milliliter of streptomycin, 0.29 millimolar L-glutamine, 10 millimolar HEPES and $5\times10^{-5}$ molar □-mercaptoethanol. T cell hybridomas were maintained in complete medium. The B cell lymphoma A20, was maintained in DMEM with the same supplements as described for complete medium, and was used as an APC line (Mohan, et al., 1993, J. Exp. Med. 177:1367–1381).

Antibodies

The following monoclonal antibodies (mAb) were used: anti4-$A^d$ (HB3), anti-I-$A^{b,d,q}$ (TIB120), anti-HSA (TIB183), and anti-Thy-1.2 (TIB99), anti-CD8 (TIB211), anti-CD3 (145-2C11). All the hybridomas were obtained from the American Type Culture Collection (ATCC, Rockville, Md.). The culture supernatants were concentrated 10× by ammonium sulfate precipitation and dialysis in PBS, sterile filtered, and stored at −20° C.

ELISAs

Anti-IL-2, anti-IFN□, and anti-IL-4, capture and biotinylated antibody pairs, and the recombinant cytokine standards (rIL-2, rIL-4, rIFN□) were purchased from Pharmingen (San Diego, Calif.). Streptavidin-conjugated horseradish peroxidase (HRP) and its substrate were purchased from Sigma Chemical Co. (St. Louis, Mo.). The cytokines were quantitated according to the manufacturer.

Preparation of Chicken Chromatin Containing Polynucleosomes

The preparation of chromatin containing polynucleosomes and purification of mononucleosomes were performed as previously described (Mohan, et al., 1993, J. Exp. Med. 177:1367–1381; Yager, et al., 1989, Biochem. 28:2271–2281).

Large Scale Cell Culture and Isolation of MHC Class II Molecules

B cell hybridomas were made by fusing HAT sensitive A20 B cell line (Folsom et al., 1984, Proc. Natl. Acad. Sci. USA 81:2045–2049) with the spleen cells from SNF$_1$ mice. A high I-$A^d$ expressing and nucleosome binding hybridoma (1F2.28) was used for isolation and purification of MHC class II, either after chromatin incubation with the hybridoma cells, or without chromatin incubation with these cells (i.e. control). Hybridoma cells ($1\times10^{10}$ total) were grown in DMEM supplemented with 10% horse serum (Mouritsen, et al., 1994, Immunology 82:529–534). Fifty micrograms per milliliter of chromatin was added to these cultures approximately 18 hours before the cells were harvested by centrifugation at 1000×g and lysed in presence of a detergent solution comprising PBS, 1% NP-40, 50 millimolar iodacetamide, 10 millimolar sodium orthovanadate, and 1 millimolar phenyl methyl sulphonyl fluoride. The solution was cleared of cell debris by an additional centrifugation at 10,000×g and frozen at −70° C.

MHC Class II Purification

MHC class II (I-$A^d$) molecule was affinity purified by application of peptide-MHC complexes to a sepharose 4B column modified with a I-$A^d$ specific antibody (HB-3) and elution of the I-$A^d$ molecules as described previously (Mouritsen, et al., 1994, Immunology 82:529–534). The protein content of the eluates was determined using a micro bicinoic acid assay (Pierce, Rockford, Ill.).

Elution and Purification of Peptides from MHC Class II olecules

Eluates containing purified MHC class II molecules (700–900 micrograms per milliliter) were concentrated to about 100 microliter using a Centricon 3 filter system (Amicon, Beverly, Mass.). The volume was adjusted such that the concentration of MHC Class II molecules was 700–900 micrograms per milliliter. The affinity purification was repeated five times. The MHC bound peptide was eluted by addition of 0.1% trifluoroacetic acid (TFA) in water and incubation at 37° C. for one hour. The resulting mixture was concentrated by ultrafiltration, and the flowthrough was collected and again concentrated to 10% of its original volume. This concentrated solution was stored under nitrogen at −70° C.

Fractionation of Peptides

The initial separation of eluted peptides having a molecular weight of less than 3000 Daltons was performed on a reverse-phase (C-18) column (RP-HPLC, 1×30 cm) using a gradient of acetonitrile and a solution comprising water and 0.1% TFA over a time period of 100 minutes. The flow rate was 1 milliliter per minute. Fractions were collected at 1 minute intervals and assayed for their ability to stimulate pathogenic autoantibody-inducing, nucleosome-specific Th clones from SNF$_1$ mice. The active (i.e. stimulatory) fractions from the initial screening was further separated by using a gradient of 0.1% heptafluoroacetone and hexafluoroacetic acid. The final separation was carried out on a nanobore HPLC and assayed for stimulation of pathogenic Th cell clones. The active fractions were sequenced by electro-spray ionization mass spectrometry (ESI-MS/MS).

Synthesis of Peptides

All the peptides used in the experiments of this Example were synthesized using FMOC chemistry (Chiron Mimotopes, san Diego, Calif.). Purity of the peptides was verified by amino acid analysis by the manufacturer. Peptides corresponding to histone protein autoepitopes were used in later in vivo experiments for the evaluation of autoimmune Th cell response and lupus acceleration. These peptides were synthesized in larger quantities, purified by HPLC using a gradient of water and acetonitrile, and analyzed by mass spectrometry for purity.

Preparation of Antigen Presenting Cells (APC)

The splenic CD4+ T cells were isolated as reported previously (Mohan, et al., 1995, J. Immunol. 154:1470–1480; Mohan, et al., 1993, J. Exp. Med. 177:1367–1381) and in Example 1. Splenic B cell and macrophage (B+Mψ) APC were prepared from one month old $SNF_1$ mice by treating splenocytes with anti-Thy 1.2 (TIB99) and rabbit complement followed by irradiation (3000 rads). The A20 B lymphoma line was treated with 50 micrograms per milliliter of mitomycin-C for 30 minutes, washed five times with PBS, then incubated for 1 hr at 37° C. After two final washes in complete medium, they were used directly as APC. For peptide presentation experiments, either the A20 B cell lymphoma or the splenic B+Mψ were used as APCs.

Proliferation and Cytokine Assays

Fresh splenic, CD4+ T cells ($5 \times 10^5$/well) were co-cultured in triplicate wells at an initial concentration of $5 \times 10^5$ cells per well, with $10^6$ cells per well of either irradiated B+Mφ or mitomycin-C treated A20 APC. Varying concentrations of either control or test peptides were added and the cultures were adjusted to 200 microliters final volume of HL-1 serum-free medium (Hycor Biomedical Inc., Irvine, Calif.) cultures were incubated for 96 hours in flat bottom 96-well plates, and at 18 hours prior to harvesting the cells, 1 microcurie of 3H-Thymidine was added to each well. The incorporated radioactivity was measured by scintillation counting. The Stimulation Index (SI) was calculated by dividing the mean counts per minute (cpm) incorporated in co-cultures of T cells and APC with test peptide by the mean cpm incorporated in control peptide co-cultures. In the case of cytokine assays, experiments were carried out as described for the proliferation assays except that the culture supernatants were removed from duplicate co-culture wells after 24–46 hours of incubation and cytokine assays were performed.

Autoantibody Quantitation

IgG autoantibodies to ssDNA, dsDNA, histones, and nucleosomes were quantitated using an ELISA as described previously (Mohan, et al., 1995, J. Immunol., 154:1470–1480; Mohan, et al., 1993, J. Exp. Med. 177:1367–1381; Burlingame, et al., 1993, J. Clin. Invest. 91:1687–1696; Losman, et al., 1992, J. Immunol., 148:1561–1569). Sera were diluted 1:100 and heat-inactivated before use. Serum from normal BALB/c mice were used as negative control. Anti-DNA mAbs 564 and 205 were used to generate standard curves (Adams, et al., 1991, Proc. Natl. Acad. Sci. USA 88:11281–11275; Mohan, et al., 1995, J. Immunol., 154:1470–1480; Mohan, et al., 1993, J. Exp. Med. 177:1367–1381; Sainis and Datta, 1988, J. Immunol. 140:2215–2224). For IgG autoantibodies to ssDNA, histones and nucleosomes, 1 unit per milliliter was considered to be equivalent to the activity of one microgram per milliliter of mAb 564, which recognizes all three autoantigens (Mohan, et al., 1995, J. Immunol., 154:1470–1480; Mohan, et al., 1993, J. Exp. Med. 177:1367–1381), and for IgG anti-dsDNA, 1 unit per milliliter was equivalent to the binding of 0.6 micrograms per milliliter of the mAb 205.

Assessment of Pathogenicity of Histone Derived Peptides

Pre-nephritic $SNF_1$ females at 12 weeks of age were each injected with 100 micrograms of one of the eluted peptide fractions, EP-1, EP-2, EP-3, or a control peptide, $OVA_{323-336}$ emulsified in complete freunds adjuvant (CFA). The animals received three more injections at two weeks interval with 50 micrograms of either an eluted peptide or the control peptide absorbed on alum (Pierce Chemical Co., Rockford, Ill.). The mice were monitored weekly for proteinuria and sacrificed when persistent proteinuria defined as in Example 1, developed. Autoantibody production and grading of glomerulonepohritis were performed as described in Example 1.

The results of the experiments presented in this Example are now described.

Identification of the Naturally Processed and Presented Th Cell Epitopes

Figure 23B:
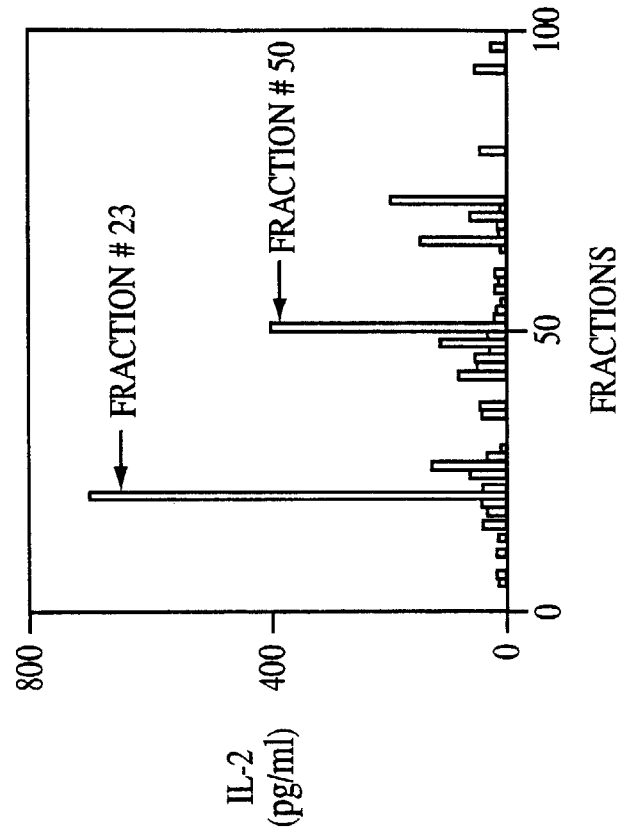
FIGS. 23A–23C, is a series of graphs illustrating the identification of naturally processed and presented histone peptide autoepitopes.
Figure 23A:
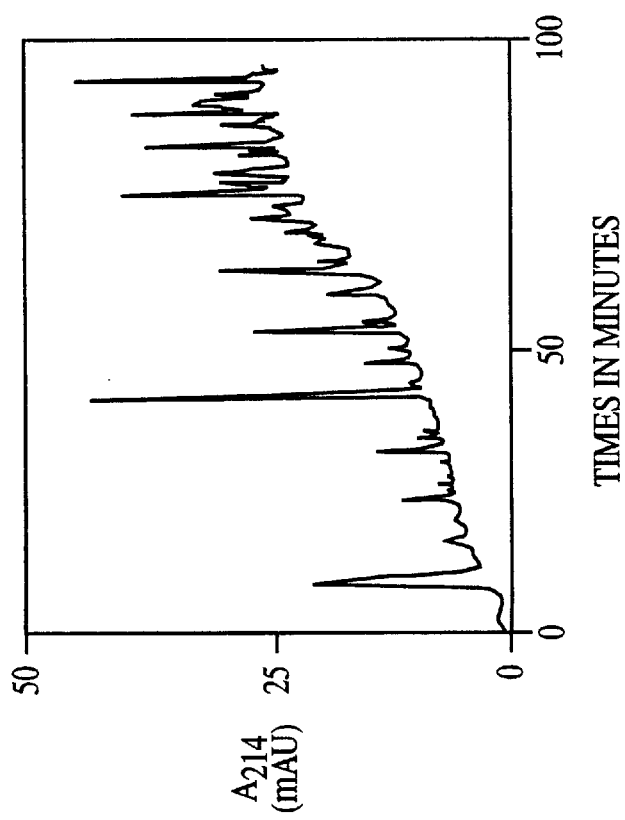

The MHC class II molecules were purified from APC cell lines derived from $SNF_1$ mice after incubating the cells with a chromatin preparation containing polynucleosomes. Peptides having a molecular weight of less than 3000 Daltons were separated on a reverse-phase (C-18) column HPLC (RP-HPLC) using a gradient of acetonitrile and water containing 0.1% TFA and assayed for stimulating ability. An example of HPLC purification of the peptide fractions is shown in FIG. 23A.

Figure 23C:
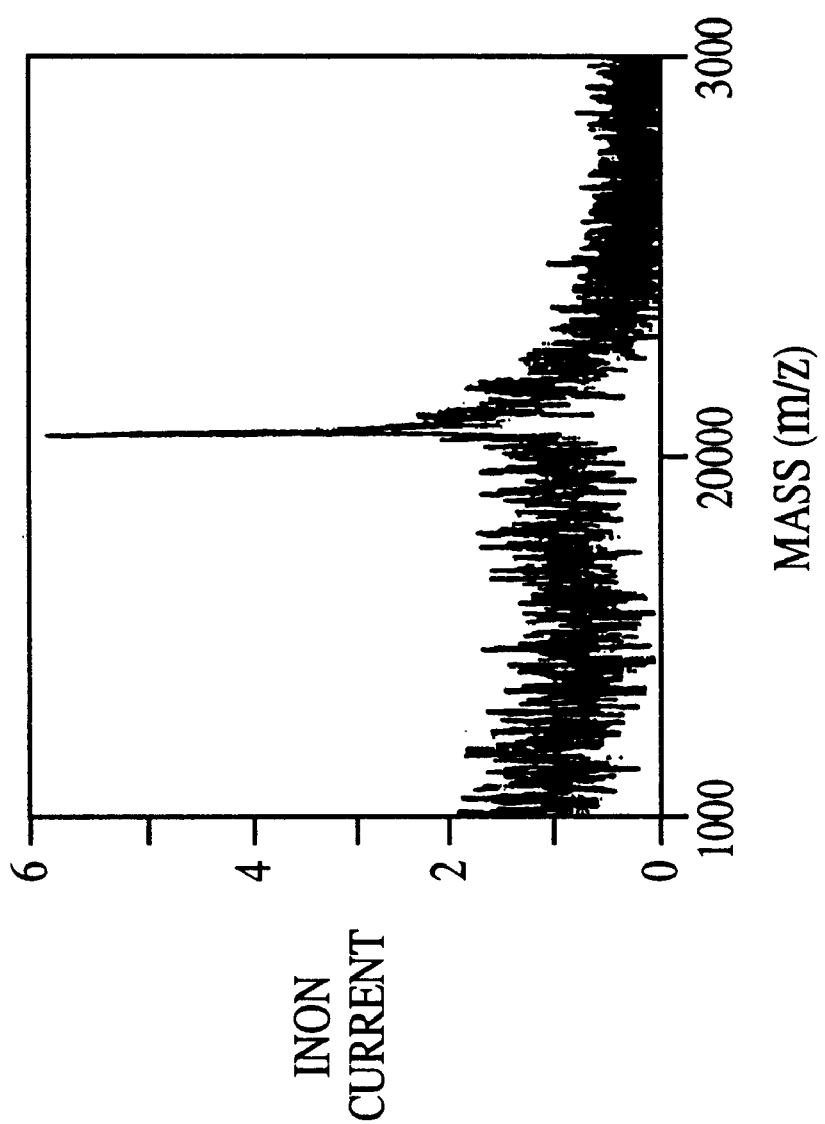
Figure 24:
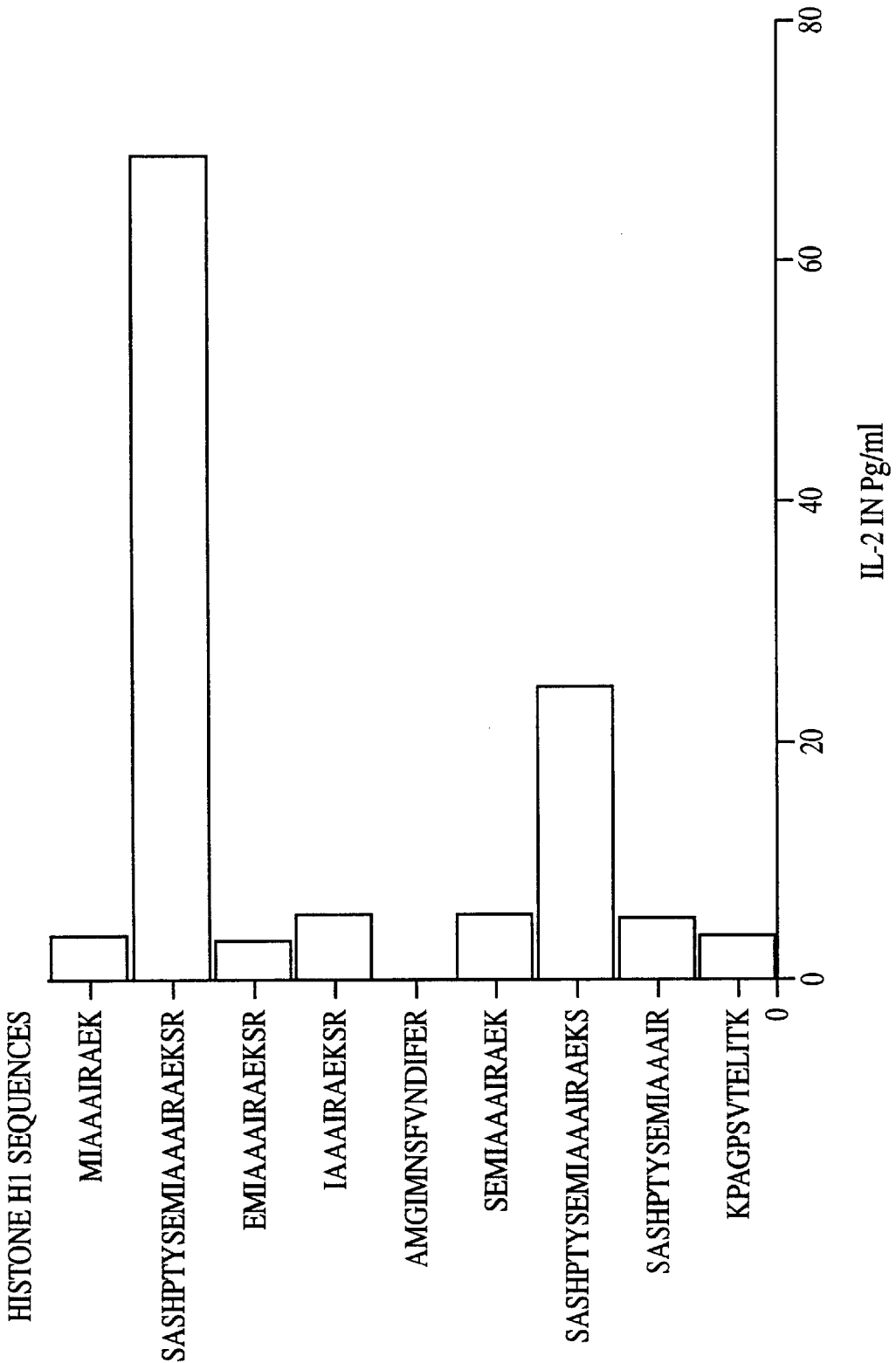
FIG. 24 is a series of graphs which illustrate the specificity of the naturally processed histone peptide epitope, EP-3 or $H1_{22-42}$. Nested sequences and unrelated sequences found in the active fractions were synthesized and retested for their ability to stimulate the nucleosome-specific Th clones derived from $SNF_1$ mice. Representative data from a Th cell clone, 3F6, is shown. In these experiments, Th cells were stimulated with various synthetic, nested histone peptide sequences by coculture with B+Mφ cells as APCs. The sequences assayed were as follows: MIAAAIRAEK (SEQ ID NO:53), SASHPTYSEMIAAAIRAEKSR (SEQ ID NO:54), EMIAAAIRAEKSR (SEQ ID NO:55), IAAAIR-AEKSR (SEQ ID NO:56), AMGIMNSFVNDIFER (SEQ ID NO:57), SEMIAAAIRAEK (SEQ ID NO:58), SASHPTY-SEMIAAAIRAEKS (SEQ ID NO:59), SASHPTYSEMI-AAAIR (SEQ ID NO:60), KPAGPSVTELITK (SEQ ID NO:61).
Figure 25A:
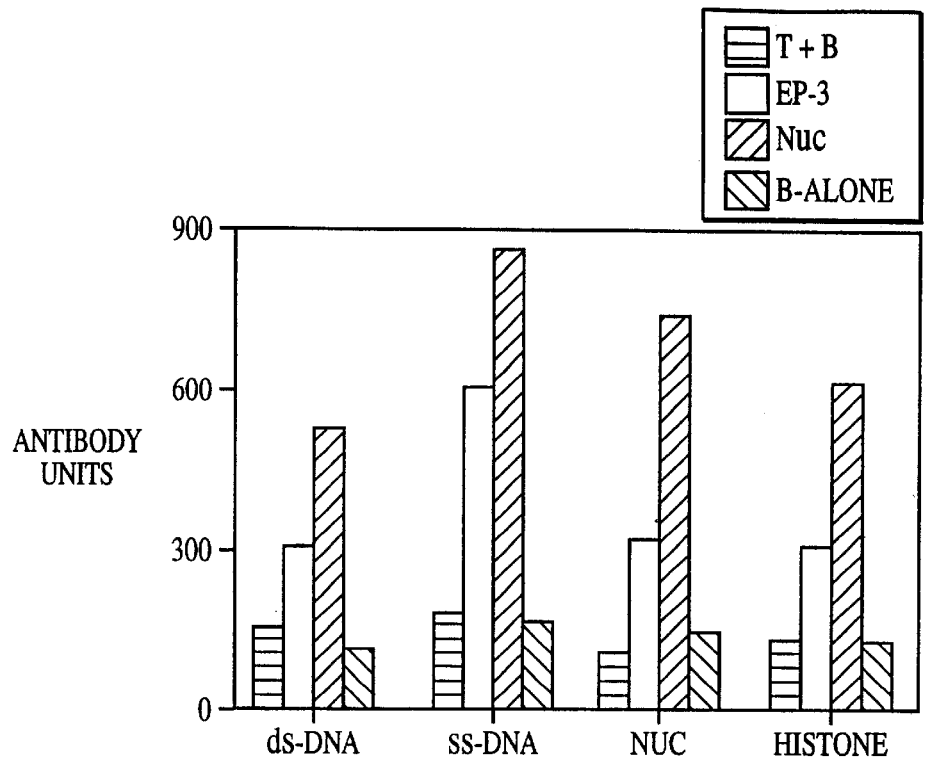
FIGS. 25A–25D, is a series of graphs depicting an assessment of the ability of selected naturally processed peptide autoepitopes to stimulate T cell help in support of SLE-associated autoantibody production by B cells obtained from lupus-prone mice. This assessment was made by performing helper assays with each of four Th cell clones in which each Th clone was cultured with B cells as APCs in either culture medium (T+B), culture medium and the naturally processed peptide, EP-3 (EP-3), or culture medium and a whole nucleosome preparation (Nuc). B cells were incubated alone as a control (B cell).
Figure 25B:
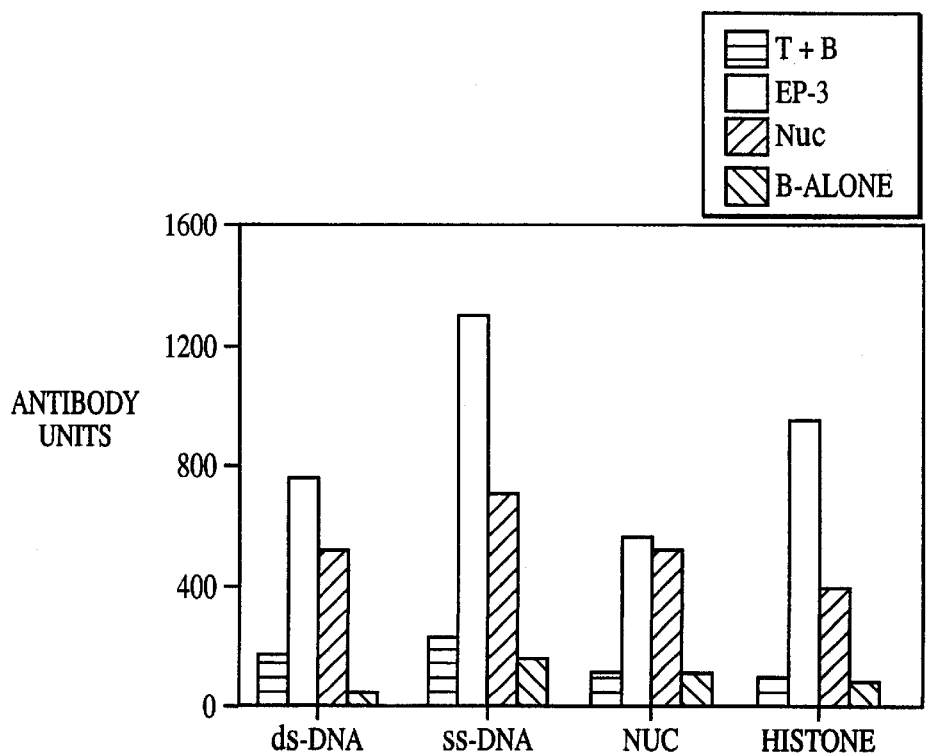
Figure 25C:
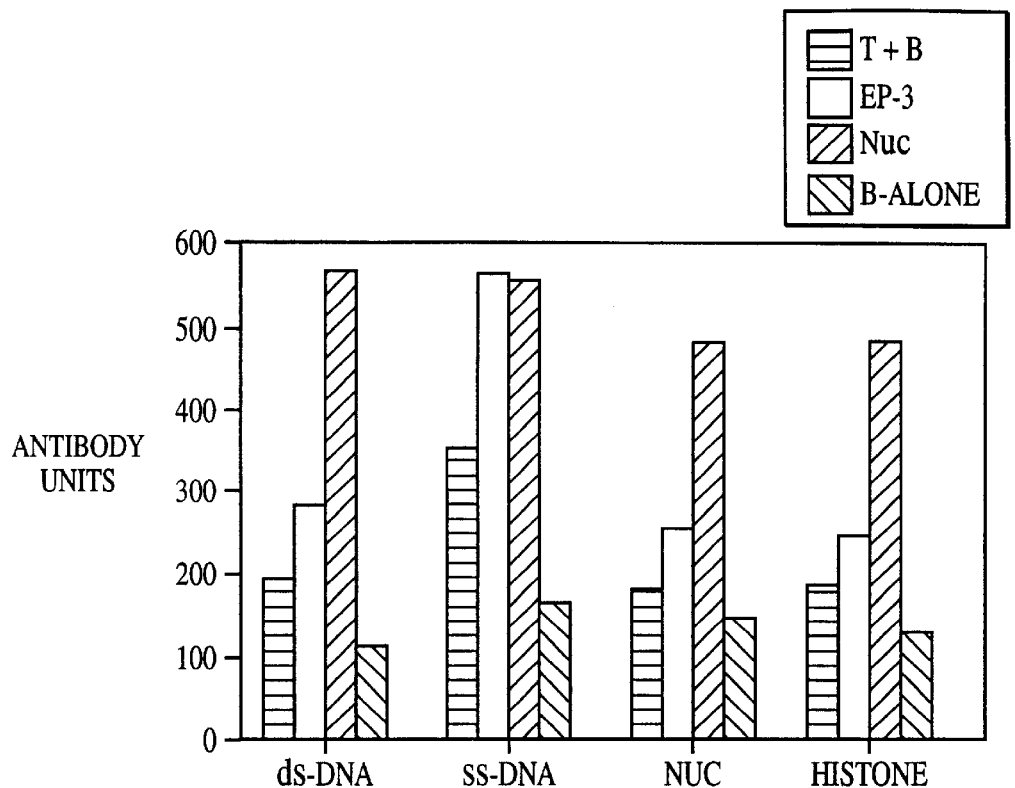
Figure 25D:
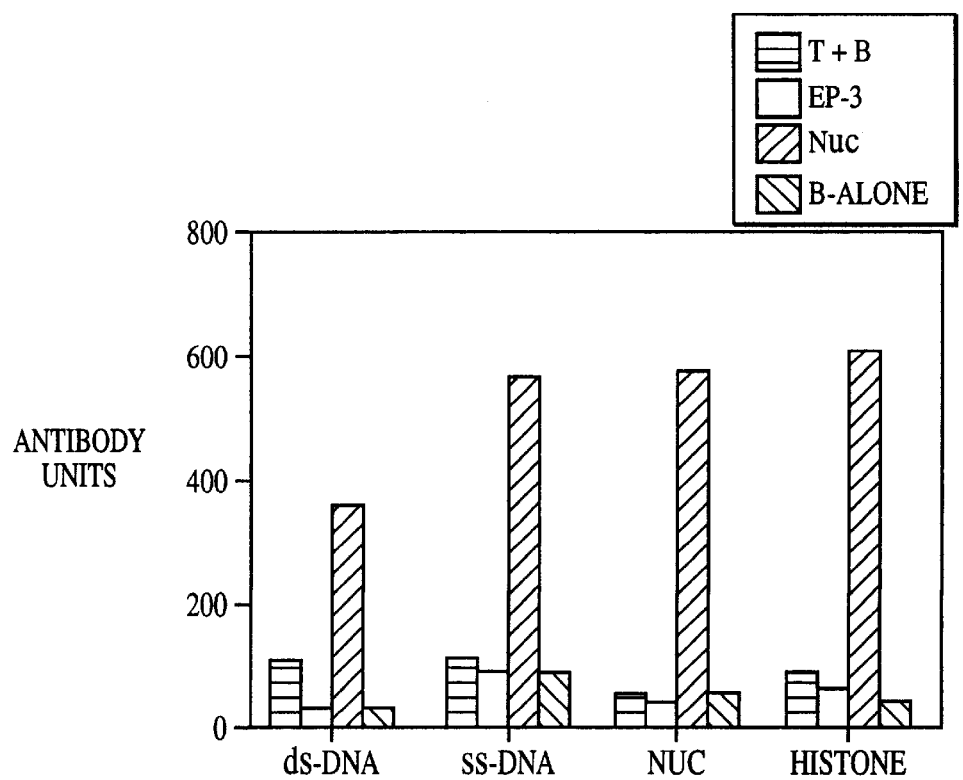

An aliquot of 50 microliters from each HPLC fraction was assayed for stimulating ability as described above. Four characterized Th clones were used as indicators of cytokine secretion (IL-2 and/or IL-4) in response to the peptide fractions, using A20 or splenic B+Mψ as APCs (Adams, et al., 1991, Proc. Natl. Acad. Sci. USA 88:11271–11275; Shi, et al., 1998, J. Exp. Med. 187:367–378). Eluate fractions from control APC cultures that were not incubated with chromatin did not stimulate the Th cell clones, as shown in FIG. 23B. Only two out of one hundred fractions tested were able to stimulate Th cell clones. These fractions were analyzed by mass spectrometry (MALDI-TOP-MS) as exemplified in FIG. 23C, which demonstrates that one fraction (#23) was homogenous, whereas another fraction (#50) revealed five peaks (not shown). The latter was further separated as described, and tested for active fractions of HPLC purified peptides.. Three naturally processed and presented, stimulatory epitopes were identified using these procedures. The sequences of the peptides are as follows: SQKEEEEGAQREKE (EP-1, SEQ ID NO: 23); DWMEEE-HGAQREKE (EP-2, SEQ ID NO: 24); and SASHPTYSE-MIAAAIRAEKSR (EP-3, or $H5_{22-42}$, SEQ ID NO: 25). The first two peptides were homologous to sequences in a transcription factor, BRN-3, which is identical in chicken, mice and humans (GenBank). A homology search demonstrated EP-2 to be identical in sequence to aa position 175–185 in BRN-3, except for one residue. EP-1 is highly homologous to EP-2, but it also matched a sequence in cytomegalovirus envelope protein at aa position 57–70. Most likely these peptides are derived from some transcription factor in the chromatin that was incubated with the APC. The third sequence (EP-3) was derived from histone H5 (aa position 22–42) in chicken nucleosome, which is homologous to histone H1 sequence of mice and humans at amino acid position 22–42 (STDHPKYSDMIVAAIQAEKNR, SEQ ID NO:26). The mouse $H1_{22-42}$ peptide was equivalent to the chicken $H5_{22-42}$ peptide in stimulating the pathogenic Th clones from $SNF_1$ lupus mice. Therefore, the mouse $H1_{22-42}$ is the autoantigenic peptide in mice and is also referred to herein as EP-3. Nested sequences and unrelated sequences that were obtained in the active fractions from the eluates were also synthesized and re-tested. As shown in FIG. 24, the unrelated sequences did not stimulate the pathogenic Th clones, thus indicating epitope specificity and authenticity of EP-3.

Eluted Peptides and Pathogenic Autoantibody Production

To test whether the naturally processed and presented peptide could facilitate augmentation of the pathogenic autoantibody production, pathogenic autoantibody-inducing Th clones 1D12, 5E9, and 3F6 that were nucleosome-specific and also responded to the EP-3 peptide or the Th clone 1G1 that was also nucleosome-specific but did not respond to EP-3, were co-cultured with freshly isolated, splenic B cells from $SNF_1$ mice in presence of EP3 ($H1_{22-42}$). After seven days of co-culture, the supernatants were assayed for IgG antibodies to the autoantigens (ds-DNA, ss-DNA, nucleosome, and histone) by ELISA. The $H1_{22-42}$ peptide stimulated the first three pathogenic Th clones and augmented their ability to help in autoantibody production,. The non-responder Th clone was not stimulated to augment help by this peptide, but was stimulated by the whole nucleosome. The $H1_{22-42}$ peptide augmented autoantibody-inducing help of responder Th clones 5E9 and 3F6, almost as much as the whole nucleosome. In the case of clone 1D12, augmentation of autoantibody-inducing help by $H1_{22-42}$ peptide was 1.5 to 2.5 times higher than that with nucleosome. The results of these experiments are depicted in FIG. 25.

Acceleration of SLE

Figure 26:
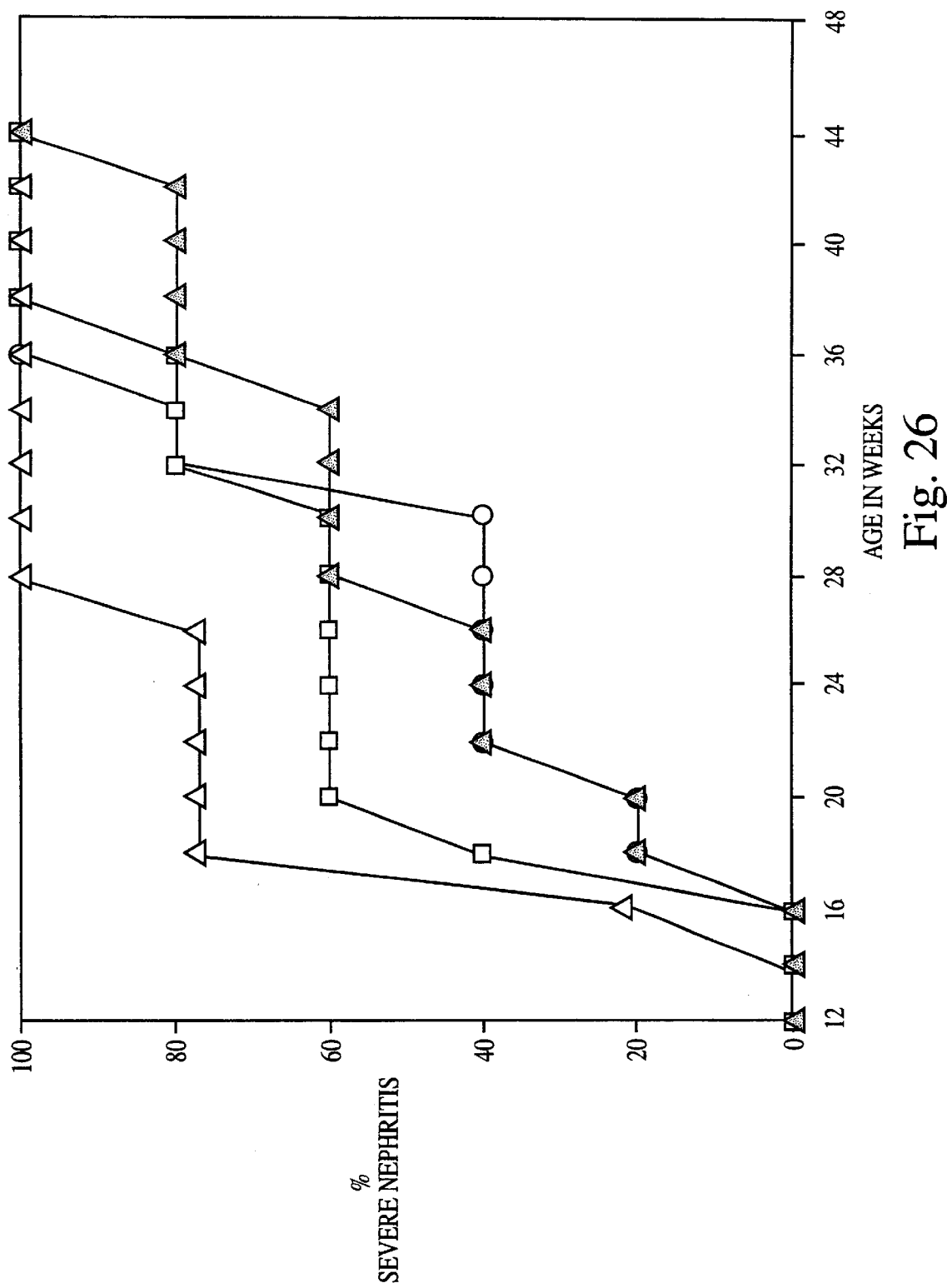
FIG. 26 is a graph depicting the acceleration of SLE-associated nephritis following immunization with naturally processed peptide autoepitopes in adjuvant.

Twelve week old prenephritic $SNF_1$ mice that were immunized with an eluted peptide, EP-2 or EP-3, in adjuvant (CFA) developed severe nephritis earlier than age matched $SNF_1$ mice injected with CFA alone or control OVA peptide in CFA. Eighty percent of the mice injected with $H1_{22-42}$ (i.e. EP-3) succumbed to severe lupus nephritis within four weeks of the first injection. Indeed, some of the $H1_{22-42}$ immunized animals developed severe nephritis in 2–3 weeks, just after the first booster immunization. By 28 weeks of age, all the EP-3 immunized mice developed severe nephritis. Eluted peptide (EP-2) also accelerated SLE in the initial phase; 60% of the mice developed disease by 20 weeks of age. But later on, the incidence of severe nephritis in this group of mice was similar to that of the control group. By contrast, EP-1 immunization did not result in any increase in the rate of disease relative to the control group. The results of these experiments are shown in FIG. 26.

The experiments presented in this Example identify peptide epitopes that are preferentially associated with MHC class II molecules and presented as autoantigens after being naturally processed by antigen presenting cells (APCs). Peptides were eluted in fractions of MHC class II molecules from APC lines that were incubated in the presence of crude chromatin. The eluted peptide fractions were purified by reverse phase HPLC (RP-HPLC) and tested for the ability to stimulate autoimmune SLE-associated T cell lines. The stimulatory peptide fractions were analyzed by Matric-assisted Laser Desorption Time of Flight Mass Spectrometry (MALDI-TOF-MS). Amino acid sequences of purified peptides in fractions which were stimulatory were then deduced by electro-spray ionization mass spectrometry (ESI-MS/MS) at the Harvard microchemical facility. The peptide sequences thus identified were synthesized, and the synthetic peptides were tested again for stimulating pathogenic, SLE-associated Th cells from $SNF_1$ mice. These naturally processed peptide autoepitope sequences include the following: EP-1 (SEQ ID NO: 23); EP-2 (SEQ ID NO: 24); and EP-3, chicken $H5_{22-42}$ (SEQ ID NO:25), or $H1_{22-42}$ (SEQ ID NO: 26). The APC line was incubated with chicken chromatin in order to distinguish the peptides derived from the chromatin processing from any endogenous nucleosomal peptides derived from dying cells in the cultures. The first two naturally-processed peptide sequences that stimulate the autoimmune T cells are homologous to sequences in transcription factor BRN-3 whose sequence is identical in chicken, mice and humans. The third sequence is homologous to histone H1 sequence at amino acid positions 22–42, which is identical in mouse and human (STDHPKYSDMI VAAIQAEKNR, $H1_{22-42}$). The $H1_{22-42}$ peptide is an extremely potent immunogen when injected with adjuvant, and it could simultaneously trigger the expansion of autoimmune Th cells, as well as autoimmune B cells of lupus. These results also indicate the potential efficacy of this dominant peptide epitope for designing tolerogens for inhibiting both autoimmune T and B cell populations in lupus. Identification of these major peptide epitopes should provide a basis for: (1), elucidating the endogeneous mechanisms of emergence and expansion of autoimmune T cells in SLE, and also for identifying molecular mimics in the environment that could precipitate the disease in susceptible individuals; (2), tracking the presence of the disease-causing Th cells for diagnostic and prognostic purposes, because such peptide-specific T cells appear long before serologic manifestations of lupus in murine models, and (3), developing autoantigenic peptide-specific therapy of lupus in humans.

The experiments presented in this Example demonstrate that histone peptides corresponding to the HI histone protein can be used to (a) develop antigen-specific therapy of SLE. Tolerization of autoimmune T cells and B cells of lupus with $H1_{22-42}$ epitope given as soluble peptide orally (oral tolerance), subcutaneously, or intravenously; (b) develop altered peptide ligands for the same purpose, after mapping T cell receptor and MHC contact residues in the peptide epitope; and (c) develop tetramers of the nucleosomal $H1_{22-42}$ peptide linked to I-$A^d$ in mice, or to HLA-DR in humans, to surface stain and track the autoimmune T cells of lupus for diagnostic and prognostic purposes. The autoimmune T cells can be present without any detectable anti-DNA autoantibodies in serum, and thus can predict the development of lupus nephritis many years in advance of emerging symptoms of the disease.

The identification of histone peptides which correspond to major SLE-associated autoepitopes as described in the above Examples 1–3 is important for developing an antigen-specific therapy to combat the disease. The following are possible as a result of the disclosure of Examples 1–3:

(a) Development of antigen-specific therapies to treat SLE which involve tolerizing autoimmune T cells and B cells involved in lupus with nucleosomal peptides given as soluble peptides orally (i.e. oral tolerance), intranasally, subcutaneously, or intravenously, or by any other route for inducing tolerance. Development of altered peptide ligands for the same purpose, following mapping of the T cell receptor and MHC contact residues in the nucleosomal peptide epitopes.

(b) Development of tetramers of HLA-DR and nucleosomal peptides to stain the surface of autoimmune T cells involved in SLE for diagnostic and prognostic purposes. Some autoimmune T cells could be present in serum without any detectable SLE-associated autoantibodies. Thus staining is useful for predicting the development of SLE-associated nephritis many years in advance of emerging symptoms of the disease.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating an animal having systemic lupus erythematosus (SLE) and a SLE-associated manifestation of nephritis, autoantibodies, and inflammation associated with autoantibodies, said method comprising administering to said animal an isolated peptide comprising a portion of a nucleosome histone protein wherein said peptide consists of an amino acid sequence selected from the group consisting of SEQ ID NOs: 1–5, 7, 9–10, 14, 18–19, and 22–26, and further wherein said isolated peptide is capable of specifically binding with a T cell receptor present on a cell, and further wherein said isolated peptide is capable of promoting immunological tolerance in an animal, thereby treating said SLE and said SLE-associated manifestation.

2. The method of claim 1, wherein said isolated peptide is administered in an amount which is from at least about 10 micrograms per kilogram of animal to at least about 1 gram per kilogram of animal.

3. The method of claim 2, wherein said amount is from at least about 100 micrograms per kilogram of animal to about 600 micrograms per kilogram of animal.

4. A method of treating a SLE-associated manifestation of nephritis in an animal having systemic lupus erythematosus, said method comprising administering to said animal an isolated peptide comprising a portion of a nucleosome histone protein, wherein said peptide consists of an amino acid sequence selected from the group consisting of SEQ ID NOs: 1–5, 7, 9–10, 14, 18–19, and 22–26, and further wherein said isolated peptide is capable of specifically binding with a T cell receptor present on a cell, and further wherein said isolated peptide is capable of promoting immunological tolerance in an animal, and wherein said peptide is administered in an amount sufficient to promote immunologic tolerance in said animal, thereby alleviating said nephritis in said animal.

5. A method of reducing the production of SLE-associated autoantibodies in an animal, said method comprising administering to said animal an isolated peptide comprising a portion of a nucleosome histone protein, wherein said peptide consists of an amino acid sequence selected from the group consisting of SEQ ID NOs: 1–5, 7, 9–10, 14, 18–19, and 22–26, and further wherein said isolated peptide is capable of specifically binding with a T cell receptor present on a cell, and further wherein said isolated peptide is capable of promoting immunological tolerance in an animal, and wherein said peptide is administered in an amount sufficient to promote immunologic tolerance in said animal, thereby reducing the production of SLE-associated autoantibodies in said animal.

6. A method of treating SLE-associated inflammation in an animal, which inflammation is caused by the production of autoantibodies in said animal, said method comprising administering to said animal an isolated peptide comprising a portion of a nucleosome histone protein, wherein said peptide consists of an amino acid sequence selected from the group consisting of SEQ ID NOs: 1–5, 7, 9–10, 14, 18–19, and 22–26, and further wherein said isolated peptide is capable of specifically binding with a T cell receptor present on a cell, and further wherein said isolated peptide is capable of promoting immunological tolerance in an animal, and wherein said peptide is administered in an amount sufficient to promote immunological tolerance in said animal, thereby inhibiting the production of SLE-associated autoantibodies in said animal and alleviating inflammation in said animal.

7. The method of claim 6, wherein said isolated peptide is administered in an amount which is from at least about 10 micrograms per kilogram of animal to at least about 1 gram per kilogram of animal.

8. The method of claim 7, wherein said amount is from at least about 100 micrograms per kilogram of animal to about 600 micrograms per kilogram of animal.

* * * * *